US011732781B2

(12) United States Patent
Lefeber et al.

(10) Patent No.: US 11,732,781 B2
(45) Date of Patent: Aug. 22, 2023

(54) GEARWHEEL TRANSMISSION WITH HIGH TRANSMISSION RATIO AND WITH IMPROVED EFFICIENCY AND/OR INCREASED CAPACITY FOR TRANSMITTING TORQUE

(71) Applicant: VRIJE UNIVERSITEIT BRUSSEL, Elsene (BE)

(72) Inventors: Dirk Lefeber, Sint-Agatha-Rode (BE); Pablo Lopez Garcia, Ixelles (BE); Stein Crispel, Saintes (BE)

(73) Assignee: VRIJE UNIVERSITEIT BRUSSEL, Elsene (BE)

( * ) Notice: Subject to any disclaimer, the term of this patent is extended or adjusted under 35 U.S.C. 154(b) by 0 days.

(21) Appl. No.: 17/625,502

(22) PCT Filed: Jul. 8, 2020

(86) PCT No.: PCT/IB2020/056422
§ 371 (c)(1),
(2) Date: Jan. 7, 2022

(87) PCT Pub. No.: WO2021/005528
PCT Pub. Date: Jan. 14, 2021

(65) Prior Publication Data
US 2022/0299090 A1 Sep. 22, 2022

(30) Foreign Application Priority Data
Jul. 8, 2019 (GB) ..................................... 1909745

(51) Int. Cl.
*F16H 3/64* (2006.01)
*B25J 9/10* (2006.01)
(Continued)

(52) U.S. Cl.
CPC ................ *F16H 3/64* (2013.01); *B25J 9/102* (2013.01); *F16H 57/08* (2013.01); *A61F 2/64* (2013.01);
(Continued)

(58) Field of Classification Search
CPC ........................................................ F16H 3/64
See application file for complete search history.

(56) References Cited

U.S. PATENT DOCUMENTS 10,495,190 B2 * 12/2019 Okamoto ................ F16H 3/663
2018/0335116 A1 11/2018 Isono

FOREIGN PATENT DOCUMENTS

DE 10-2011-080002 A1 1/2013
DE 10-2013-215878 B3 1/2015
(Continued)

OTHER PUBLICATIONS

International Search Report and Written Opinion issued by the European Patent Office acting as International Searching Authority for International Patent Application No. PCT/IB2020/056422 dated Oct. 7, 2020 (14 pages total).

*Primary Examiner* — Derek D Knight
(74) *Attorney, Agent, or Firm* — Dinsmore & Shohl LLP

(57) ABSTRACT

Gearwheel transmission comprising a first stage and a second stage, the second stage being a differential gearing comprising a planetary gear train system which is executed in a quasi duplicated form, wherein a first component is forming a torque resisting means, wherein a second component is interconnected or interacting with an output shaft, the overall transmission efficiency in the first stage being higher than in the second stage and/or the overall capacity for transmitting torque in the second stage being higher than in the first stage.

18 Claims, 28 Drawing Sheets

(51) Int. Cl.
*F16H 57/08* (2006.01)
*A61F 2/64* (2006.01)
*A61F 2/66* (2006.01)
*A61F 2/68* (2006.01)

(52) U.S. Cl.
CPC . *A61F 2/66* (2013.01); *A61F 2/68* (2013.01); *A61F 2002/6614* (2013.01); *A61F 2002/6836* (2013.01)

(56) References Cited

FOREIGN PATENT DOCUMENTS

DE  10-2013-216802 A1  2/2015
WO  98/22733 A1  5/1998

* cited by examiner

GEARWHEEL TRANSMISSION WITH HIGH TRANSMISSION RATIO AND WITH IMPROVED EFFICIENCY AND/OR INCREASED CAPACITY FOR TRANSMITTING TORQUE

The present invention relates to a gearwheel transmission with high transmission ratio and with improved efficiency and/or increased capacity for transmitting torque.

The present invention also relates to an infinitely variable transmission (IVT), which comprises such a gearwheel transmission in accordance with the invention, as well as to a prosthesis or orthosis or a robotic machine, which comprises a gearwheel transmission or an IVT in accordance with the invention.

From the above it is clear that a gearwheel transmission of the invention is typically applied in medical devices such as a prosthesis or orthosis or in robotic machines.

Nevertheless, it is not excluded from the invention to apply such a gearwheel transmission of the invention in other fields, such as in the automotive industry or in vehicles in general, in wind turbines, in all kinds of machines or devices, regardless of their size.

A gearwheel transmission in accordance with the invention is especially useful in applications wherein the conditions are rather extreme, i.e. in conditions wherein very high transmission ratios are required, only limited space is available, relatively high torques should be exerted at the output side of the gearwheel transmission, relatively high speeds are applied at the input side of the gearwheel transmission and energy consumption should be restricted as much as possible.

This is for example typically the case in prostheses, such as a foot or knee prosthesis, or in joints of: robotic machines, wherein mechanisms are applied for supporting the movement of the concerned joint.

As a consequence, in a gearwheel transmission in accordance with the invention high transmission ratios are combined with compactness, high efficiency of the transmission and an increased capacity for transmitting torque.

A gearwheel transmission in accordance with the invention has for example typically a transmission ratio of at least 1:100 and more likely a transmission ratio of at least 1:200 and still more preferable of at least 1:500 or even higher.

Some gearwheel transmissions are already known according to the state of the art, which can reach such high transmission ratios, but these known gearwheel transmissions do not perform well as far as the other above-mentioned requirements are concerned.

The main reason for this rather bad performance is probably that such known gearwheel transmissions were designed for completely different applications wherein the requirements were different or less strict, so that the designers did focus on creating a gearwheel transmission with a high transmission ratio rather than looking into all the other afore-mentioned aspects and characteristics of the desired gearwheel transmission which are important in nowadays applications, such as in wind turbines, prostheses and robotic joints.

Other aspects that become more and more important are the cost of manufacturing, the sustainability of products, reduction of energy consumption, protection of the environment in general, which results in increasingly higher demanding standards, not considered at all or to a lesser extent in prior art designs.

Seen from a nowadays perspective, a first disadvantage of the known gearwheel transmissions with high transmission ratio is that they have generally a structure which is rather extensive or wherein many components interact in a low performing way with one another introducing many restrictions on the design of the different components (for example restrictions concerning their assembly), which makes a compact execution impossible.

Furthermore, the efficiency of the known gearwheel transmissions with high transmission ratio is rather low.

There are many reasons why this is the case.

A first reason is again that the chosen structure itself of the known gearwheel transmissions introduces a lot of losses.

In some cases for example gearwheels are doubled for stability reasons, causing very high friction losses.

In other cases gearwheels, for example typically planetary gearwheels, are simultaneously interacting with other gearwheels which are operating at very different rotational speeds and different torques, for example typically with a sun gear as well as with a ring wheel.

As a consequence, the execution of such a concerned gearwheel cannot be optimized for all the operational conditions it is involved in, with as a result a rather low efficiency performance.

Another very important reason why there are high energy losses, the importance of which is not understood or overlooked according to the state of the art, is actually the consequence of a combination of factors, which will hereafter be represented simultaneously by means of a single, newly defined parameter.

This parameter is newly introduced in this application and will according to the invention be indicated by the "rolling work".

The rolling work is hereby defined according to the invention as being the distance one gearwheel rolls on another gearwheel, measured at the pitch circle of the gearwheel, multiplied with the interacting force at that pitch circle.

This interacting force is proportional to the friction force and as such the rolling work is a measure for the interaction losses of the concerned gear train.

This rolling work is intrinsic and therefore depends on the structure of the gearwheel transmission.

Indeed, imagine a first gearwheel transmission and a second gearwheel transmission which have the same transmission ratio.

The first gearwheel transmission however has a structure in which gearwheels have to roll a considerably longer distance over one another in order to obtain this ratio than in the second gearwheel transmission.

As a result, the rolling work in the first gearwheel transmission will highly likely be greater than in the second gearwheel transmission.

This rolling work concept introduces a new perspective or a new focus on important factors causing energy losses in gearwheel transmissions, which combination of causes is not taken into consideration at all or the importance of which is overlooked according to the present state of the art.

A second reason why the known gearwheel transmissions with high transmission ratio have a rather low energy efficiency, is due to the fact that, according to the present state of the art, the role or function which different elements, parts or substructures play in the overall gearwheel transmission is overlooked and that the gearwheel transmission is seen as a rather homogeneous, unified mechanism.

As a consequence, different elements, parts or substructures of the known gearwheel transmissions with high transmission ratios are simply not recognized and therefore execution parameters of such elements, parts or substructures are not adapted to their concerned operational conditions in order to increase the overall efficiency, resulting in the mentioned rather low efficiency performance.

The present invention aims at a gearwheel transmission with high transmission ratio which does not show one or more of the above disadvantages and possibly also other disadvantages.

In particular, it is an aim of the invention to provide a gearwheel transmission with high transmission ratio having an improved efficiency and an increased capacity for transmitting torque compared to the known gearwheel transmissions with a similar high transmission ratio.

Another aim of the invention is to provide such gearwheel transmission that has a structure which allows to optimize the performance of any implied pair of gearwheels, without affecting at the same time the performance of any or as few as possible other gearwheels.

Still another aim of the invention is to design a gearwheel transmission with high transmission ratio having a very compact and lightweight structure so that it can therefore be easily built in in small spaces such as in prostheses or joints of robotic machines.

Another aim of the invention is to provide a gearwheel transmission with high transmission ratio wherein friction losses, rolling work and dynamic losses are eliminated as much as possible, so to obtain a highly energy efficient transmission.

Furthermore, it is an aim of the invention to deliver a gearwheel transmission with high transmission ratio which is easily locked and which has good back-drivable properties.

It is also an aim of the invention to provide a gearwheel transmission with high transmission ratio which is especially adapted for configurations wherein relatively high speed-low torque conditions are present at the input side, while relatively low speed-high torque conditions are needed at the output side of the gearwheel transmission.

To this aim, the invention relates to a gearwheel transmission with high transmission ratio and improved efficiency and/or increased capacity for transmitting torque, comprising a first stage and a second stage, which are interconnected and/or are interacting with one another for transmission of torque and rotational speed from a first stage input shaft to a second stage output shaft and/or vice versa, the gearwheel transmission provided in a housing, wherein the first stage comprises at least a first stage entry gearwheel which is mounted fixedly on the first stage input shaft and which is interacting for the transmission of rotational speed and torque with one or more first stage output elements, in a direct manner, or indirectly through an interconnection mechanism comprising one or more interconnection gearwheels; and wherein the second stage comprises a second stage planetary type gearwheel assembly, wherein the second stage is a differential gearing comprising a planetary gear train system which is executed in a quasi duplicated form composed of an input side and an output side, comprising respectively a first set and a second set of planetary gearing, which are mutually quasi identical but slightly different from one another, which interact respectively with first and second interacting gearing of respectively the input side and the output side and which sets are supported in a rotatable manner either each on their own separated planet carrier or together on a common planet carrier, each set of planetary gearing being composed of a number of planetary gearing elements which are disposed circumferentially on their supporting planet carrier, the first set and the second set of planetary gearing being linked to form a linking mechanism for transmission of torque and/or speed between the input side and the output side; wherein at least the gearwheels of the first stage and the second stage are executed according to a set of execution parameters which influence transmission efficiency and/or capacity for transmitting torque and wherein certain gearwheels of the gearwheel transmission are executed with at least some of their execution parameters set to different parameter values, in such a way that the overall transmission efficiency considered in the first stage as a whole is higher than the overall transmission efficiency considered in the second stage as a whole and/or the overall capacity for transmitting torque considered in the second stage as a whole is higher than the overall capacity for transmitting torque considered in the first stage as a whole; and, wherein a first component, a sun wheel or a ring wheel of the second stage or a planet carrier of the gearwheel transmission, is forming a torque resisting or torque controlling means in that it is permanently blocked or impeded in a controllable way; and, wherein a second component, i.e. respectively a rotatable sun wheel or a rotatable ring wheel of the second stage or a rotatable planet carrier of the gearwheel transmission is interconnected or interacting with the output shaft.

Such a gearwheel transmission in accordance with the invention has a lot of advantages, since it is composed of specific building blocks, i.e. a first and a second stage, which provide the right functionality at the right place in the gearwheel transmission.

The second stage plays herein a very important role and is executed in a quasi duplicated form comprising an input side and an output side, respectively with a first set and a second set of nearly identical planetary gearing which are linked to one another forming a linking mechanism for transmission of torque and speed.

Such a kind of quasi duplicated planetary gear train is very interesting, since it allows to transform a relatively high speed/low torque rotation provided at the first stage input shaft into a very low speed/high torque rotation at the second stage output shaft and vice versa.

Transformation of a high speed/low torque input into a low speed/high torque output is interesting in applications such as in prostheses.

Indeed, it is only possible to integrate a very small driving actuator in such a prosthesis, the actuator providing a very fast rotation at minimal torque and this fast movement at low force can be transformed with a gearwheel transmission of the invention into a relatively slow rotation for rotating a rather heavy part of a human body.

An example of the opposite is a rather slowly driving powerful engine connected at the second stage output shaft for driving an electric generator which is connected at the first stage input shaft and which generates electric energy at a relatively high rotation speed and lower torque.

Of course these are just a few examples and a gearwheel transmission of the invention can be applied in many other applications, for example in other applications already discussed above, but also in still other applications.

The way this is realised with a gearwheel transmission of the invention is easily understandable as follows.

It is clear that the second stage has a very symmetric structure due to the quasi duplicated form of its planetary gear train system.

As a consequence, when a component at the input side of the second stage is blocked or severely impeded so that its speed is zero or nearly zero, this will obviously result in a similar speed at the symmetric equivalent component of the output side of the second stage.

The purpose of the first component of the gearwheel transmission, which is forming a torque resisting or torque controlling means, is to provide this blocking or impeding of a component of the second stage or to set the amount of torque on that component.

The second component of the gearwheel transmission which is connected to the second stage output shaft can be considered as the (more or less symmetric) complement of the first component, which is forming the torque resisting means or torque controlling means.

So, the torque resisting means or torque con rolling means determines to a large extent how the second stage output shaft is driven by the first stage input shaft or vice versa.

The first stage can be considered as a kind of pre-gearing by which the first stage input shaft is connected to the second stage.

This first stage ensures that the rotational speed at the first stage input shaft is brought within a range suitable for being fed to the second stage, usually by decreasing the rotational speed provided at the first stage input shaft.

Of course, this way of seeing things relates to the case wherein the first stage input shaft is used to drive the gearwheel transmission and the second stage output shaft, but also the opposite is possible, for example when a slowly turning wind turbine connected to the second stage output shaft is driving a fast rotating generator which is connected at the first stage input shaft.

In this last example wherein the second stage output shaft is driving the gearwheel transmission, the first stage can be considered as a post-gearing which increases the rotational speed and lowers the torque from the second stage towards the first stage input shaft.

The side that drives the gearwheel transmission and the side that is driven by the gearwheel transmission can also be invert d during use of the gearwheel transmission.

Apart from its very interesting mechanical structure, a gearwheel transmission in accordance with the invention has still another very interesting characteristic in that the first stage and the second stage are executed in different ways, in particular in such a way that the overall transmission efficiency considered in the first stage as a whole is higher than the overall transmission efficiency considered in the second stage as a whole and/or the overall capacity for transmitting torque considered in the second stage as a whole is higher than the overall capacity for transmitting torque considered in the first stage as a whole.

This means that a certain degree of optimization in the execution of both stages has been applied, when compared to one another, in function of the tasks to be performed by each stage.

In the first stage this optimization is towards higher overall transmission efficiency, since components are rotating at relatively high speeds and low torques.

In the second stage this optimization is towards higher overall capacity for transmitting torque, since components are rotating at relatively low speeds and high torques and forces are exerted on the components.

It is clear that all the aforementioned characteristics combined result in a very performant gearwheel transmission, which can be executed in a very compact manner and that a very high reliability of the gearwheel transmission is ensured.

In a possible execution of a gearwheel transmission in accordance with the invention, the gearwheel transmission comprises an intermediate planet carrier, which is mounted in a rotatable manner in the housing and which is separated from the first stage input shaft as well as from the second stage output shaft and wherein intermediate carrier planetary gearwheel shafts are provided on said intermediate planet carrier for supporting planet wheels of the second stage and possibly also of the first stage in a rotatable manner.

As mentioned, the second stage is provided with a planetary gear train system having a first set and a second set of planetary gearing, which sets are supported in a rotatable manner either each on their own separated planet carrier or together on a common planet carrier.

In some embodiments of a gearwheel transmission in accordance with the invention said common planet carrier or one of the separated planet carriers also bears planetary gearwheels of the first stage.

In that case such a planet carrier can be seen as a part of the second stage which is also supporting gearwheels of the first stage.

On the other hand, from another point of view this planet carrier can be seen as a part of the first stage which is also supporting gearwheels of the second stage.

A third way to look at it, is that the concerned planet carrier is an intermediate planet carrier which is not a part of the first stage nor of the second stage and which is supporting gearwheels of those stages.

In a preferred embodiment of a gearwheel transmission in accordance with the invention the first stage and the second stage are interconnected in such a way that the one or more first stage output elements is or are fixedly interconnected with one or more second stage input elements according to one of the following cases:
  a single first stage output element is fixedly connected to a single second stage input element which meshes with one or more planetary gearing elements of a first set of planetary gearing of the second stage;
  a single first stage output element is fixedly connected to a single second stage input element which meshes with one or more planetary gearing elements of a second set of planetary gearing of the second stage;
  one or more first stage output elements are fixedly interconnected with corresponding one or more second stage input elements formed by planetary gearing elements of a first set and a second set of planetary gearing of the second stage which are interconnected or which form compound planetary gearwheels; or,
  a single first stage output element which is fixedly connected to a planet carrier of the gearwheel transmission.

So, the first stage and the second stage of such an embodiment of a gearwheel transmission in accordance with the invention are linked to one another by fixed interconnection of some elements of the respective stages.

Torque transmission between elements which are fixedly interconnected is of course most efficient and as a consequence, in this case, also the torque transmission between the two concerned stages.

The fixed interconnections can also be very easily realised in the most varying ways.

In a preferred embodiment of a gearwheel transmission in accordance with the invention the first and the second interacting gearing of the second stage taken together are one of the following:
a) a pair of separate ring wheels;
b) a pair of separate sun wheels; or,
c) a pair of compound gearwheels which is composed by a compound sun wheel and a compound ring wheel.

As mentioned above, the second stage comprises a planetary gear train system which is executed in a quasi duplicated form composed of an input side and an output side, comprising respectively a first set and a second set of planetary gearing, which interact respectively with first and second interacting gearing of respectively the input side and the output side.

According to the invention the interacting gearing is preferable in line with one of the above-mentioned options a)-c), each option having a certain advantage compared to the other options, and possibly also a certain disadvantage when compared to the other options.

In an embodiment in line with option a) the first set and the second set of planetary gearing of the second stage interact respectively with first and second interacting gearing, which are separate ring wheels.

An advantage of using ring wheels is that they are very suitable for transmitting high torques, due to their large diameters.

On the other hand, the big size of the ring wheels complicates the integration of the gearwheel transmission in cramped spaces.

In an embodiment in line with option b) the first set and the second set of planetary gearing of the second stage, interact respectively with first and second interacting gearing, which are now separate sun wheels.

It is clear that such a configuration with interacting gearing in the form of sun wheels is less suitable for transmitting high torques.

On the other hand, such a gearwheel configuration can more easily be integrated when the available space is limited.

According to the invention in the cases of the above-mentioned options a) and b) a linking mechanism is preferably realised between the input side and the output side of the planetary gear train system with quasi duplicated form of the second stage by a fixed interconnection of corresponding, constitutive components of the first and second sets of planetary gearing which form compound planetary linkage gearwheels which are supported on a single common planet carrier.

So, in short, in these cases the first set and the second set of planetary gearing of the second stage are fixedly interconnected while each of the sets are meshing with a separate gearwheel, each with a separate ring wheel in the case of option a) and each with a separate sun wheel in the case of option b).

By the fixed interconnection of the planetary gearwheels of the input and output side of the second stage a very robust configuration is obtained.

If furthermore in the case of option a) said ring wheels form the first and second components of the second stage, i.e. one of the ring wheels is fixedly connected to a housing so to form a torque resisting means or torque controlling means, while the other ring wheel is fixedly connected to the second stage output shaft, then, according to the invention, the second stage forms a so-called ring differential gearing.

Such a gearwheel transmission wherein the second stage forms a so-called ring differential gearing is very advantageous in that it can provide a very high transmission ratio and high torque can be delivered at the second stage output shaft, while its rotational speed is kept very low, if furthermore in the case of option b) said sun wheels form the first and second components of the second stage, then this second stage forms, according to the invention, a so-called sun differential gearing.

A gearwheel transmission of the invention wherein the second stage forms a so-called sun differential gearing is advantageous in the sense that it can be executed in a more compact way.

In general, the obtained overall transmission ratio will however be more limited and also the torque delivered at the second stage will be less high compared to a configuration with a second stage formed as a ring differential gearing.

A third configuration of the second stage can be composed corresponding to the above-mentioned option c) wherein the interacting gearing taken together form a pair of compound gearwheels which is composed by a compound sun wheel and a compound ring wheel and wherein a linking mechanism is formed by this pair of compound gearwheels, while the first and second set of planetary gearing of respectively the input side and the output side are separate from one another and each respectively supported on their own, separated planet carriers.

If in such a configuration the separated planet carriers furthermore form the first and second components of the second stage, i.e. one planet carrier is blocked or forms a torque resisting or torque controlling means and the other planet carrier is fixedly connected to the second stage output shaft, then this second stage forms, according to the invention, a so-called carrier differential gearing.

One of the compound sun wheel and the compound ring wheel which form together the linking mechanism between the input side and the output side of the second stage is preferably used for driving the second stage.

It is obvious that such a second stage which forms a carrier differential gearing comprises more components than the other described types, but on the other hand, by keeping the planet carriers and both sets of planetary gearwheels separated from one another, also new possibilities are created.

First of all, one of the planet carriers is playing the role of torque resisting means, preferably by being fixedly connected to a housing or ground.

This can be advantageous compared to a configuration wherein a common rotating planet carrier is used for supporting sets of fixedly connected planetary gearwheels, since such a common planet carrier usually forms a quite heavy component in order to cope with the forces exerted on it.

Furthermore, since the first and second set of planetary gearing of the second are kept separated from one another, the respective gearwheels can turn at different rotational speeds.

In a specific configuration of a gearwheel transmission in accordance with the invention the second stage forms a ring differential gearing as follows.

In this configuration the second stage comprises a second stage compound planetary type gearwheel assembly, comprising a second stage fixed ring wheel which is fixedly connected to the housing, a second stage rotatable ring wheel which is rotating simultaneously with the second stage output shaft, as well as second stage compound planetary gearwheels which each are supported on a corresponding primary, intermediate carrier planetary gearwheel shaft, each first planetary gearwheel of such a second stage compound planetary gearwheel meshing with the second stage fixed ring wheel and each second planetary gearwheel of such a second stage compound planetary gearwheel meshing with the second stage rotatable ring wheel, wherein the first planetary gearwheels of the second stage compound planetary gearwheel form the planetary gearing elements of a first set of planetary gearing of the second stage and wherein the second planetary gearwheels of the second stage compound planetary gearwheels form the planetary gearing elements of a second set of planetary gearing of the second stage.

Even more specifically the invention also relates to a gearwheel transmission with high transmission ratio and improved efficiency and/or increased capacity for transmitting torque, comprising a first stage and a second stage, which are interconnected and/or are interacting with one another for transmission of torque and rotational speed from a first stage input shaft to a second stage output shaft and/or vice versa, the gearwheel transmission provided in a housing and furthermore comprising an intermediate planet carrier, which is mounted in a rotatable manner in the housing and which is separated from the first stage input shaft as well as from the second stage output shaft and wherein intermediate carrier planetary gearwheel shafts are provided on said intermediate planet carrier, characterised in that the first stage comprises at least a first stage entry gearwheel which is mounted fixedly on the first stage input shaft and which is interacting for the transmission of rotational speed and torque with one or more first stage output elements, in a direct manner or indirectly through an interconnection mechanism comprising one or more interconnection gearwheels; and wherein the second stage comprises a second stage compound planetary type gearwheel assembly, comprising a second stage fixed ring wheel which is fixedly connected to the housing, a second stage rotatable ring wheel which is rotating simultaneously with the second stage output shaft, as well as second stage compound planetary gearwheels which each are supported on a corresponding primary, intermediate carrier planetary gearwheel shaft, each first planetary gearwheel of such a second stage compound planetary gearwheel intermeshing with the second stage fixed ring wheel and each second planetary gearwheel of such a second stage compound planetary gearwheel intermeshing with the second stage rotatable ring wheel, wherein the one or more first stage output elements is or are fixedly interconnected with one or more second stage input elements according to one of the following cases:
  a single first stage output element is fixedly connected to a single second stage input element which intermeshes with one or more of the first planetary gearwheels of the second stage compound planetary gearwheels;
  a single first stage output element is Fixedly connected to a single second stage input element which intermeshes with one or more of the second planetary gearwheels of the second stage compound planetary gearwheels;
  one or more first stage output elements are fixedly interconnected with corresponding one or more second stage input elements formed by the compound planetary gearwheels; or,
  a single first stage output element is fixedly connected to the intermediate planet carrier; and,
  wherein at least the gearwheels of the first stage and the second stage are executed according to a set of execution parameters which influence transmission efficiency and/or capacity for transmitting torque and wherein certain gearwheels of the gearwheel transmission are executed with at least some of their execution parameters set to different parameter values, in such a way that the overall transmission efficiency considered in the first stage as a whole is higher than the overall transmission efficiency considered in the second stage as a whole and/or the overall capacity for transmitting torque considered in the second stage as a whole is higher than the overall capacity for transmitting torque considered in the first stage as a whole.

Such an embodiment of a gearwheel transmission in accordance with the invention, but also other embodiments in general described above are very advantageous in that they have a very effective structure for attaining very high transmission ratios in a very compact space.

In particular, the gearwheel transmission has two stages which are not only different for as far as the arrangement of the components they comprise is concerned, but each stage is optimized by adapting the way these components are executed, so to optimize their suitability for the function they have to fulfill in each stage.

Hereby, things are arranged so that the overall transmission efficiency considered in the first stage as a whole is higher than the overall transmission efficiency considered in the second stage as a whole.

Additionally or as an alternative, the overall capacity for transmitting torque considered in the second stage as a whole is higher than the overall capacity for transmitting torque considered in the first stage as a whole.

So, gearwheels of the gearwheel transmission are executed in such a way that they can attain a good performance which is adapted in accordance with their position in the gearwheel transmission, resulting in an overall performance of the gearwheel transmission which is certainly higher than the overall performance in gearwheel transmissions known according to the state of the art.

Hereto, the concerned gearwheels are executed with some execution parameters being set to certain parameter values in order to increase the performance in the corresponding situation in the gearwheel transmission.

By an execution parameter is meant a parameter which defines the way the gearwheel is executed, such as its module, surface roughness, tooth geometry, thickness, accuracy, used material, profile shift, . . . .

Changing the way a concerned gearwheel is executed by setting one or more of its execution parameters to a certain value, does not essentially change the transmission ratio of the gearwheel transmission (except possibly on a very little scale, such as when a profile shift is applied), and it does essentially not change the actual functioning of the gearwheel transmission other than by changing its efficiency or its capacity for transmitting torque or the like.

In a rather restricted way, a stage in the gearwheel transmission can be defined as being a part of the gearwheel transmission which can be axially positioned near to a consecutive stage and whereby torque and speed is transmitted from one stage to another through interconnection of components of each stage which are axially spaced from one another.

A stage of the gearwheel transmission can also be defined in a somewhat larger way by being a part of the gearwheel transmission which is interconnected or interacts with another stage or part of the gearwheel transmission and which parts or stages can be axially positioned near each other or which can surround one another or be surrounded entirely or partially in an axial direction or in a radial direction or even in an axial direction and a radial direction at the same time.

In order to define which components of the gearwheel transmission are part of the first stage and which components of the gearwheel transmission are part of the second stage, in this text a clear division between the first stage and the second stage is made by stating that the interconnection between the stages is only by four possible ways.

In the first two possible interconnection configurations, a single first stage output element is fixedly connected to a single second stage input element which intermeshes with one or more of the first, or in the other case one or more of the second, planetary gearwheels of the second stage compound planetary gearwheels.

In another interconnection configuration the first stage and the second stage are interconnected at one or more first stage output elements which are fixedly interconnected with corresponding one or more second stage input elements formed by the compound planetary gearwheels.

In still another interconnection configuration, a single first stage output element is fixedly connected to the intermediate planet carrier or another planet carrier in order to interconnect the first and the second stage.

As a consequence, the output of the first stage can be one first stage output element as well as multiple first stage output elements, dependent on the required conditions.

Similarly, the input of the second stage can be one second stage input element as well as multiple second stage input elements.

What's more, the one or more first stage output elements are interconnected with the one or more second stage input elements, or, what is in many cases equivalent, be made together as one monolithic part.

In more general terms, but not as such claimed in present claim 1, the one or more first stage output elements could also interact with the one or more second stage input elements, for example by intermeshing or by an interaction such as between a planet carrier and one or more gearwheels.

In a typical embodiment, some gearwheels of a gearwheel transmission in accordance with the invention which are positioned nearer to the second stage output shaft are executed such that they can take a higher torque load compared to other gearwheels of the gearwheel transmission which are positioned not so near to the second stage output shaft, for example by being executed in a stronger or heavier material or with a rougher surface or by applying a profile shift which brings the concerned gearwheels closer to one another causing a tighter mutual interaction.

Furthermore or as an alternative, some gearwheels of the gearwheel transmission which are positioned more near to the first stage input shaft are executed such that they induce less energy losses and increase transmission efficiency compared to other gearwheels of the gearwheel transmission which are positioned not so near to the first stage input shaft, for example by being executed in a less heavy material or by being executed with more smoothly surfaces, etc.

A procedure that can be used in order to check whether or not a gearwheel transmission is a gearwheel transmission in accordance with the invention can for example consist of the following steps.

First check whether or not it comprises the required components in each stage.

If this is the case, then verify whether or not one of the four above-mentioned conditions for interconnection between the two stages is fulfilled.

Finally, measure or calculate the overall efficiency and the overall capacity for transmitting torque in both stages of the gearwheel transmission and observe whether or not the overall efficiency is higher in the first stage than in the second stage and whether or not the overall capacity for transmitting torque is higher in the second stage compared to the overall capacity for transmitting torque in the first stage.

If one of these two conditions is fulfilled or if both are fulfilled, then the gearwheel transmission is a gearwheel transmission in accordance with the invention.

It is clear that a comparison is made between the first stage and the second stage as far as their overall efficiency and capacity for transmitting torque is concerned.

By focusing the attention during design to the most important aspect in each stage, i.e. by optimizing the first stage towards increased overall efficiency and the second stage towards increased overall capacity for transmitting torque, a gearwheel transmission is however obtained with an overall performance which is higher than the performance of the existing gearwheel transmissions of a similar type, since such optimization does not exist in these known gearwheel transmissions.

Furthermore, any possible arrangement within each stage itself is allowed according to the invention, so that there are no further restrictions on how components are executed within each stage.

In a possible embodiment of a gearwheel transmission in accordance with the invention however the gearwheel transmission is such that at least the gearwheels of the first stage and the second stage are executed according to a set of execution parameters which influence transmission efficiency and/or capacity for transmitting torque and wherein certain gearwheels of the gearwheel transmission are executed with at least some of their execution parameters set, to different parameter values, in such a way that following a torque transmission path through the gearwheel transmission from the first stage input shaft towards the second stage output shaft the difference in execution is such that the capacity for transmitting torque of consecutive gearwheels along the path is the same or increasing, and when following a torque transmission path through the gearwheel transmission from the second stage output shaft towards the first stage input shaft the difference in execution is such that the efficiency of transmission realized by consecutive gearwheels along the path is the same or increasing.

A great advantage of such an embodiment of a gearwheel transmission in accordance with the invention is that it has a structure which can be divided into two main parts, a first stage and a second stage, which are structurally different for performing different tasks, while at least some gearwheels of the gearwheel transmission are executed in a different way, so that they are specially adapted in order to have an improved performance in their specific conditions.

Contrary to what is the case in these type of gearwheel transmissions known in the art, in such an embodiment of a gearwheel transmission of the invention the components of the gearwheel transmission are executed in such a way that a trend can be clearly found, i.e. following a torque transmission path from the first stage input shaft towards the second stage output shaft, capacity for transmitting torque is (non-strictly) increasing, while following that torque transmission path in the opposite direction transmission efficiency is (non-strictly) increasing.

This trend can consist of only one step, for example when components of the first stage are differently executed with execution parameters set to different parameter values than components of the second stage.

The trend can also consist of multiple steps, within each of the stages and/or overlapping the stages.

Hereby, a torque transmission path is a path through the gearwheel transmission through which forces are transmitted from one gearwheel to another in order to realize the overall transmission of torque.

Typically, the structure of the first stage is such that high rotational speed of the first stage input shaft is reduced into a relatively lower rotational speed at the output of the first stage and this in rather low torque conditions.

At least some of the elements and preferably all of the elements involved in this first stage are therefore according to the invention preferably executed such that as less as possible energy is lost, such as due to friction losses and rolling work losses, in these relatively high speed-low torque conditions, for example by using relatively lightweight materials, applying relatively smaller contact ratios, relatively smaller modules, smoother surfaces and good lubrication and so on.

The structure of the second stage with a compound planetary stage and a fixed ring wheel as well as a rotating ring wheel allows for a tremendous additional reduction of the rotational speed and this in relatively high torque conditions.

At least some of these elements acid preferably all the elements involved in this second stage are therefore according to the invention preferably executed such that essentially torque is transmitted in an effective way in these relatively low speed-high torque conditions, for example by using relatively stronger materials, applying relatively higher contact ratios, relatively bigger modules, rougher and more hardened surfaces and so on.

It is this combination of a well-chosen structure composed of two stages with their particularities for reducing the rotational speed and increasing torque, and an adapted execution of the gearwheels of the gearwheel transmission as far as their performance is concerned, that makes it possible to obtain a gearwheel transmission with high transmission ratio which is very energy efficient, compact, lightweight and which has an increased capacity for transmitting torque.

A procedure that can be used in order to check whether or not a gearwheel transmission is a gearwheel transmission in line with the above-mentioned conditions of having an increasing transmission efficiency along a torque transmission path towards the first stage input shaft and an increasing capacity for transmitting torque along a torque transmission path towards the second stage output shaft can for example consist of the following steps.

First check whether or not it comprises the required components in each stage.

If this is the case, then choose a torque transmission path through the gearwheel transmission from the first stage input shaft towards the second stage output shaft and verify whether or not the gearwheels of a pair of consecutive gearwheels are executed with one or more execution parameters set to different parameter values, i.e. execution parameters that influence the transmission efficiency or the capacity for transmitting torque of the concerned stage.

When there is such a difference, then let us call the gearwheel of said differently executed pair of consecutive gearwheels which is positioned in the chosen torque transmission path closest to the first stage input shaft, the first differently executed gearwheel, and the other gearwheel of that pair the second differently executed gearwheel.

Then compare a gearwheel transmission wherein the difference in execution is eliminated, in particular by executing the second differently executed gearwheel with its execution parameters set to the same parameter values as the first differently executed gearwheel, with the gearwheel transmission as it is actually executed and check whether or not by introducing the difference in execution in this case the capacity for transmitting torque is increased.

Repeat this procedure for each pair of differently executed consecutive gearwheels along the chosen torque transmission path and check whether the required condition is fulfilled in each case.

Similarly, choose a torque transmission path through the gearwheel transmission from the second stage output shaft towards the first stage input shaft.

Then compare a gearwheel transmission wherein the difference in execution is eliminated, in particular by executing the first differently executed gearwheel with its execution parameters set to the same parameter values as the second differently executed gearwheel, with the gearwheel transmission as it is actually executed and check whether or not by introducing the difference in execution, in this case if the transmission efficiency is increased.

Repeat also this procedure for each pair of differently executed consecutive gearwheels along the chosen torque transmission path and check whether the required condition is fulfilled in each case.

If all the afore-mentioned checks appear to be positive the concerned gearwheel transmission is considered to be a gearwheel transmission in accordance with the invention of a type having the characteristics of the here discussed embodiment.

Obviously, in many gearwheel transmissions more than one pair of differently executed gearwheels will be found.

This means the same tests should be repeated for each consecutive pair of differently executed gearwheels along the torque transmission paths in both directions and the gearwheel transmission will only be a gearwheel transmission in accordance with the invention if all these tests have a positive result.

Luckily, in many examples, pairs of interacting gearwheels of the gearwheel transmission will typically be executed in such a way that the execution parameters of each gearwheel of such a pair of interacting gearwheels are set to the same respective parameter values.

In that case the number of checks to be executed is obviously very much reduced.

In another procedure, it suffices to measure or calculate firstly the transmission efficiency in parts of the gearwheel transmission along a chosen torque transmission path towards the first stage input shaft and to verify whether or not the transmission efficiency is (non-strictly) increasing in that sense.

Additionally, in such a procedure one should observe the capacity for transmitting torque in the different parts of the gearwheel transmission along a chosen torque transmission path towards the second stage output shaft and verify whether or not there the capacity for transmitting torque is (non-strictly) increasing in the corresponding sense.

This subject matter corresponding to this possible embodiment is at present claimed in claim 2, dependent on claim 1, but it could be used as an alternative way to formulate the invention in general terms (as a new claim 1 not dependent on present claim 1), by indicating how components within the gearwheel transmission can be executed, i.e. by using the subject matter of present claim 2 as an alternative for the last paragraph of present claim 1.

In a preferred embodiment of a gearwheel transmission in accordance with the invention the gearwheel transmission comprises more precisely at least the following elements or characteristics:

an intermediate planet carrier which is concentric with the second stage output shaft and which is mounted in a rotatable manner for a rotating movement around the second stage output shaft;

a number of circumferentially spaced apart intermediate carrier planetary gearwheel shafts mounted fixedly or in a rotatable manner on the intermediate planet carrier;

primary, intermediate carrier planetary gearwheel shafts, which each provide support for a series of fixedly interconnected, stepped second stage planetary gearwheels forming a second stage compound planetary gearwheel, either in a rotatable manner or by being fixedly interconnected with the concerned series of second stage planetary gearwheels;

a second stage fixed ring wheel which is concentric with the second stage output shaft and which is fixedly connected to the housing of the gearwheel transmission and which is intermeshing with a first group of circumferentially spaced apart second stage planetary gearwheels composed by the first planetary gearwheel of each afore-mentioned series of second stage planetary gearwheels; and, a second stage rotatable ring wheel which is concentric with the second stage output shaft, which is mounted in a rotatable manner in the housing, which is fixedly connected to the second stage output shaft and which is intermeshing with a second group of circumferentially spaced apart second stage planetary gearwheels composed by the second planetary gearwheel of each afore-mentioned series of second stage planetary gearwheels.

The particularities of these elements of the gearwheel transmission will become clear during the discussion of the drawings.

In another preferred embodiment of a gearwheel transmission in accordance with the invention the first stage is a high speed-low torque stage and the second stage is a low speed-high torque stage, compared relatively to one another, the first stage comprising first stage gearwheels interacting with one another for transmitting rotational speed of and torque delivered at the first stage input shaft into a decreased rotational speed of and an increased torque at one or more first stage output elements, the second stage comprising second stage gearwheels interacting with one another for transmitting rotational speed of and torque at one or more second stage input elements into rotational speed of and torque at a second stage output shaft.

Such an embodiment of a gearwheel transmission in accordance with the invention is advantageous in that it is clearly specified that the first stage should be relatively high speed-low torque and the second stage relatively low speed-high torque in order to obtain a high performance of the gearwheel transmission.

In the above-mentioned examples the first stage is considered as an input stage, which operates at relatively high speeds-low torques, while the second stage is an output stage, which operates at relatively, low speeds and higher torques.

This is typically the case in applications such as in gearwheel transmissions for prostheses or in robotics, wherein a small actuator delivers high speed rotational speed at the first stage input shaft in order to exert relatively high torque at the second stage output shaft, for example in order to move a pair of limbs with respect to one another.

In these examples rotational speed and torque delivered at the first stage input shaft is transmitted into a lower speed and higher torque at the second stage output shaft, so the first stare is driving the second stage.

Of course, in other applications, the second stage can play the role of input stage, while the first stage is then the output stare, which is driven by the second stage.

In that case, relatively low rotational speed and high torque delivered at the second stage output shaft can be transmitted into relatively high speed rotational movement and relatively low torque at the first stage input shaft.

This is for example typically interesting in applications such as in a wind turbine.

Indeed, in that case the relatively slow rotational movement of the wind turbine blades should be delivered at the second stage output shaft, and this rotational movement is transformed in the gearwheel transmission into a relatively high speed rotational movement at the first stage input shaft, which shaft should in that case be connected to the input shaft of an electric generator.

In still other applications, the role of input stage and output stage can be inverted during operation, for example in an electric car, the electric engine riving power during acceleration of the car to the first stage input shaft for driving wheels which are connected to the second stage output shaft, while during deceleration of the car energy of the wheels can be delivered form the second stage output shaft to the first stage input shaft, so to store this energy back into a battery.

In short, the meaning of "input" and "output" in this text should be understood as used for describing the relationship between components of the gearwheel transmission from a point of view wherein the first stage is driving the second stage.

In reality however, the "input" can drive the "output", but in other applications or even in the same application the "output" can drive "the input" as well.

In a preferred embodiment of a gearwheel transmission in accordance with the invention the first stage output elements are formed by a group of circumferentially spaced apart first stage output planetary gearwheels which are each interconnected with or form a monolithic part with a corresponding planetary gearwheel of a group of circumferentially spaced apart second stage planetary gearwheels, which represent second stage input elements, so to form hybrid compound planetary gearwheels comprising a series of three planetary gearwheels, composed of a pair of second stage planetary gearwheels and a first stage planetary gearwheel.

Such an embodiment of a gearwheel transmission in accordance with the invention is very advantageous in that it allows for a very compact design.

Hereby, each group of circumferentially spaced apart but axially aligned planetary gearwheels of the compound planetary type gearwheel assembly preferably in meshes with only one other gearwheel.

Each planetary gearwheel of such a group of spaced apart but axially aligned planetary gearwheels essentially operates at the same rotational speed and torque.

As a consequence, the way of execution of each afore-mentioned group of planetary gearwheels and the corresponding intermeshing gearwheel can be adapted to the concerned operational conditions of torque and rotational speed, so to optimize the performance of the concerned pairs of gearwheels and this without influencing the performance of other pairs of gearwheels of the neighbouring groups of planetary gearwheels of the compound planetary type gearwheel assembly.

This results clearly in a highly performant gearwheel transmission.

In another preferred embodiment of a gearwheel transmission in accordance with the invention the first stage output element is a single first stage output element which is formed by a first stage output planet carrier and which is interconnected with a second stage input element, which is a single second stage input element.

In a particular embodiment of a gearwheel transmission in accordance with the invention the single second stage input element is a second stage input sun wheel of the second stage compound planetary type gearwheel assembly, wherein this second stage input sun wheel is intermeshing with each planetary gearwheel of a group of circumferentially spaced apart second stage planetary gearwheels composed by a planetary gearwheel of each second stage compound planetary gearwheel.

This embodiment of a gearwheel transmission in accordance with the invention has the advantage that it can be made still more compact than the former embodiment, when the afore-mentioned group of circumferentially spaced apart second stage planetary gearwheels are simultaneously intermeshing with the second stage input sun wheel and with the second stage fixed ring wheel.

However in that case, the freedom to adapt the execution of gearwheels in function of the operational conditions is obviously less great.

This means that in such an embodiment there is somewhat less freedom in order to reduce energy losses by choosing the right way of execution or to choose other execution parameters.

In still another embodiment of a gearwheel transmission in accordance with the invention the first stage gearwheels or other elements of the first stage and second stage gearwheels or other elements of the second stage are each executed in accordance with a set of mechanical design parameters, wherein one or more of these first stage gearwheels or other elements of the first stage and one or more second stage gearwheels or other elements of the second stage are executed in such a way that one or more of their execution parameters have parameter values which are different in the first stage compared to the corresponding parameter values in the second stage, wherein in particular first parameter values of certain execution parameters of this set for the first stage and second parameter values of the corresponding execution parameters of this set for the second stage differ from one another in such a way that the first parameter values increase efficiency in a high speed-low torque mechanical gearing, while the second parameter values increase robustness, strength and/or capacity for transmitting torque in a low speed-high torque mechanical gearing, compared relatively to one another.

By an execution parameter is understood a parameter which defines the mode of execution of the concerned gearwheel, which does influence its performance in the entire gearwheel transmission, but which for example does essentially not modify the role of the concerned gearwheel in the entire gearwheel transmission.

Preferably, in a gearwheel transmission in accordance with the invention the afore-mentioned set of execution parameters comprises one or more of the following execution parameters which influence the efficiency or the capacity for transmitting torque of the concerned components:

a module;
a quality level;
an accuracy;
a profile-shift;
a contact ratio;
a tooth geometry;
a filet profile;
a roughness;
a material; and/or,
a surface hardness.

More in particular, in a gearwheel transmission according to the invention wherein a first pair of gearwheels of the gearwheel transmission is executed with a first module, a first quality level, a first accuracy, a first profile-shift, a first contact ratio, a first roughness, a first tooth geometry, a first material and a first surface hardness, and wherein a second pair of gearwheels of the gearwheel transmission, which, on a torque transmission path through the gearwheel transmission from the first stage input shaft towards the second stage output shaft is positioned closer to the second stage output shaft than the first pair of gearwheels, is executed with a second module, a second quality level, a second profile-shift, a second contact ratio, a second roughness, a second tooth geometry, a second material and a second surface hardness, preferably one or more of the following conditions is or are fulfilled:

the first module is smaller than the second module;
the first quality level is higher than the second quality level;
the first accuracy is higher than the second accuracy;
the level and distribution of the first profile shift are optimized for efficiency and the level and distribution of the second profile shift are optimized for robustness;
the first contact ratio is smaller than the second contact ratio;
the first tooth geometry is optimized for efficiency and the second tooth geometry is optimized for increasing capacity for transmitting torque;
the contact roughness in the first stage is smaller than the contact roughness in the second stage;
the first material is lighter and/or has a lower strength than the second material; and,
the first surface hardness is smaller than the second surface hardness.

It is clear that in the afore-mentioned embodiments the execution parameters are set in different parts of the gearwheel transmission, so to obtain a high-performant overall structure.

According to another preferred principle of the invention the gearwheel transmission is structured in such a way that each gearwheel of the gearwheel transmission intermeshes with one or more intermeshing gearwheels, whereby the intermeshing gearwheels of the concerned gearwheel all operate at the same or essentially the same rotational speed and torque and wherein the pair or pairs of intermeshing gearwheels formed by the concerned gearwheel and each of its intermeshing gearwheels are executed according to certain execution parameters one or more parameter values of which differing from the parameter values of corresponding execution parameters of other pairs of gearwheels of the gearwheel transmission which operate at relatively higher or lower rotational speeds and torques and wherein the difference is towards relatively increased efficiency for the concerned gearwheel pair or pairs when its or their corresponding operational rotational speed is higher and torque is lower compared to other pairs of gearwheels of the gearwheel transmission which operate at relatively lower rotational speeds and higher torques and wherein the difference is towards increased capacity for transmitting torque in the opposite case, i.e. in the case other pairs of gearwheels of the gearwheel transmission operate at relatively higher rotational speeds and lower torques.

Clearly, by applying this principle embodiment of a gearwheel transmission in accordance with the invention are obtained in which the different parts are specially executed so to perform very well, resulting in a high overall performance of the gearwheel transmission.

Looked from another perspective, most of the embodiments of a gearwheel transmission in accordance with the invention can also be described in very general terms as follows.

From this perspective, the invention is concerning a gearwheel transmission with high transmission ratio and improved efficiency and/or increased capacity for transmitting torque, comprising a first stage and a second stage, which are interconnected and/or are interacting with one another for transmission of torque and rotational speed from a first stage input shaft to a second stage output shaft and/or vice versa, the gearwheel transmission provided in a housing and furthermore comprising an intermediate planet carrier, which is mounted in a rotatable manner in the housing and which is separated from the first stage input shaft as well as from the second stage output shaft and wherein intermediate carrier planetary gearwheel shafts are provided on said intermediate planet carrier, wherein the first stage comprises at least a first stage entry gearwheel which is mounted fixedly on the first stage input shaft and which is interacting for the transmission of rotational speed and torque with one or more first stage output elements, in a direct manner, or indirectly through an interconnection mechanism comprising one or more interconnection gearwheels; and wherein the second stage comprises a second stage compound planetary type gearwheel assembly, comprising a second stage fixed ring wheel which is fixedly connected to the housing, a second stage rotatable ring wheel which is rotating simultaneously with the second stage output shaft, as well as second stage compound planetary gearwheels which each are supported on a corresponding primary, intermediate carrier planetary gearwheel shaft, each first planetary gearwheel of such a second stage compound planetary gearwheel intermeshing with the second stage fixed ring wheel and each second planetary gearwheel of such a second stage compound planetary gearwheel intermeshing with the second stage rotatable ring wheel.

It is clear that from this perspective, for expressing the invention inmost general terms, only the components by which such a gearwheel transmission in accordance with the invention is composed, are taken into consideration, while the way these components are executed in accordance with certain execution parameters is this time not taken into consideration.

In a particular case of a gearwheel transmission in accordance with the invention still a very general concept is taken as the starting point, but the first stage is restricted to the cases wherein the first stage entry gearwheel is interacting for the transmission of rotational speed and torque with one or more first stage output elements indirectly through an interconnection mechanism comprising one or more interconnection gearwheels.

Of course, even when starting from these general perspectives, other characteristics of a gearwheel transmission in accordance with the invention (such as certain execution parameters or specific components), as described in other parts of this text, should be taken into consideration in order to get a more precise description of each embodiment.

With the intention of better showing the characteristics of the invention, hereafter, as an example without restrictive character whatsoever, some preferred embodiments of a gearwheel transmission according to the present invention, are described, with reference to the accompanying illustrations, wherein.

Figure 12:
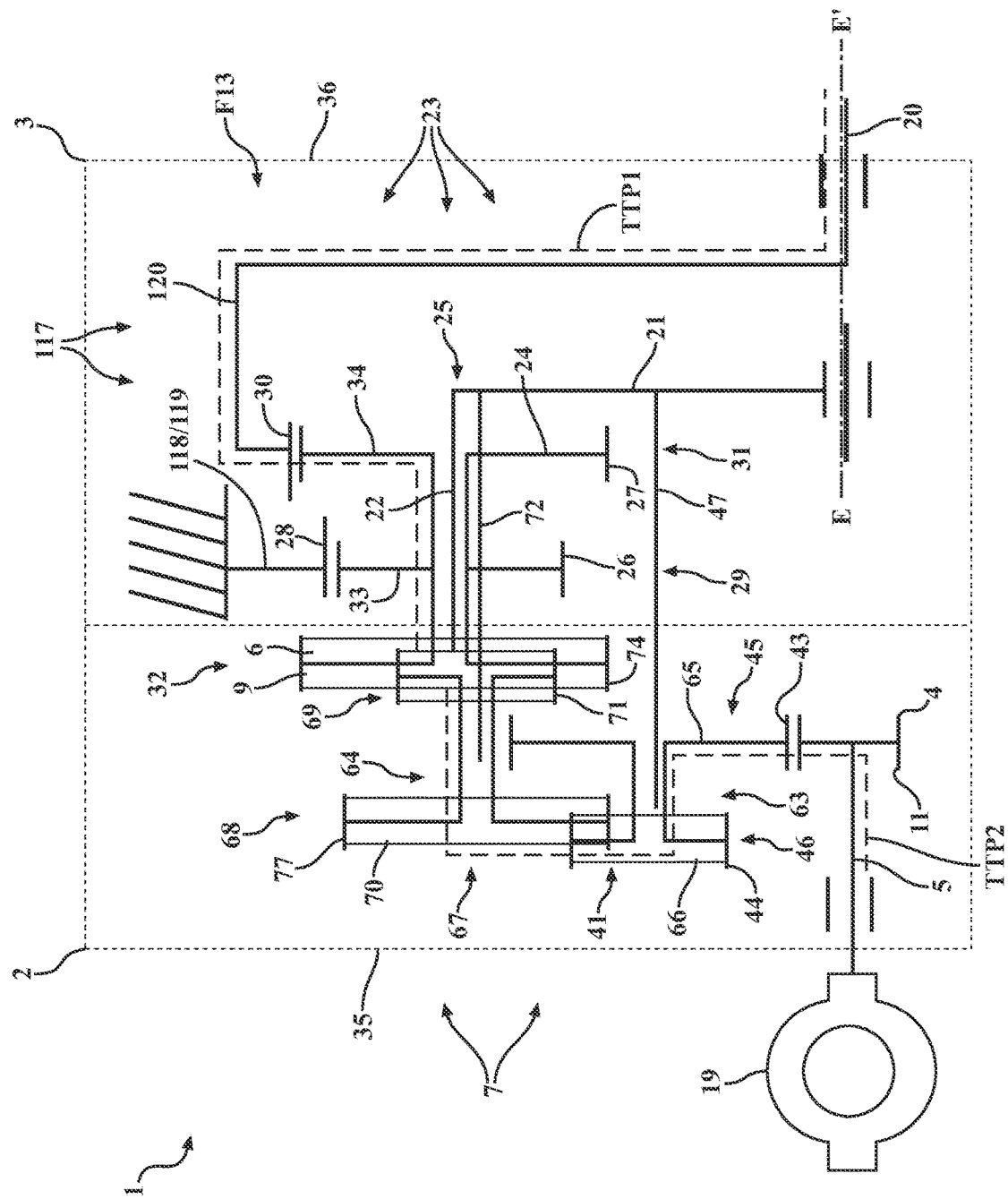
Figure 13:
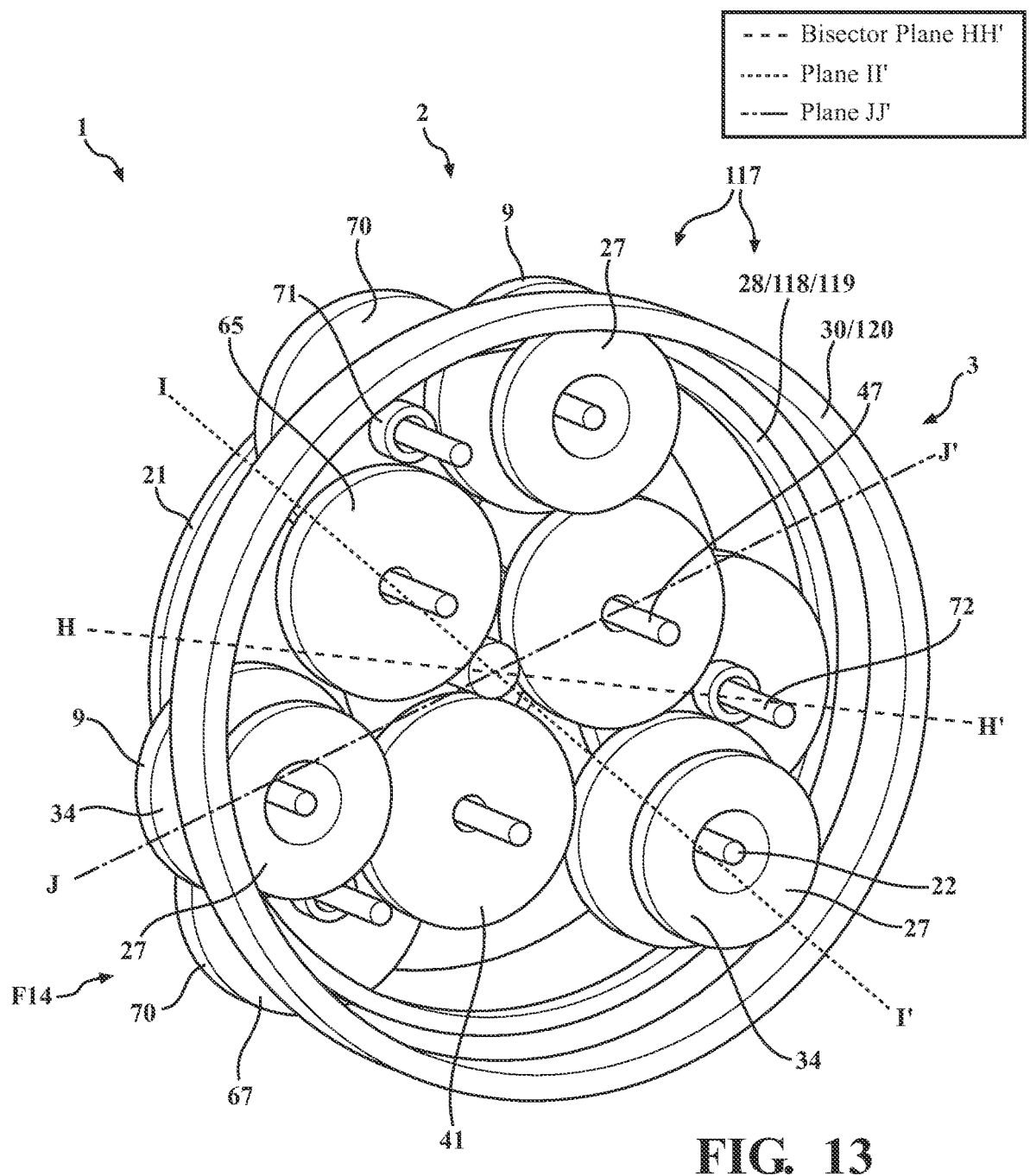
Figure 14:
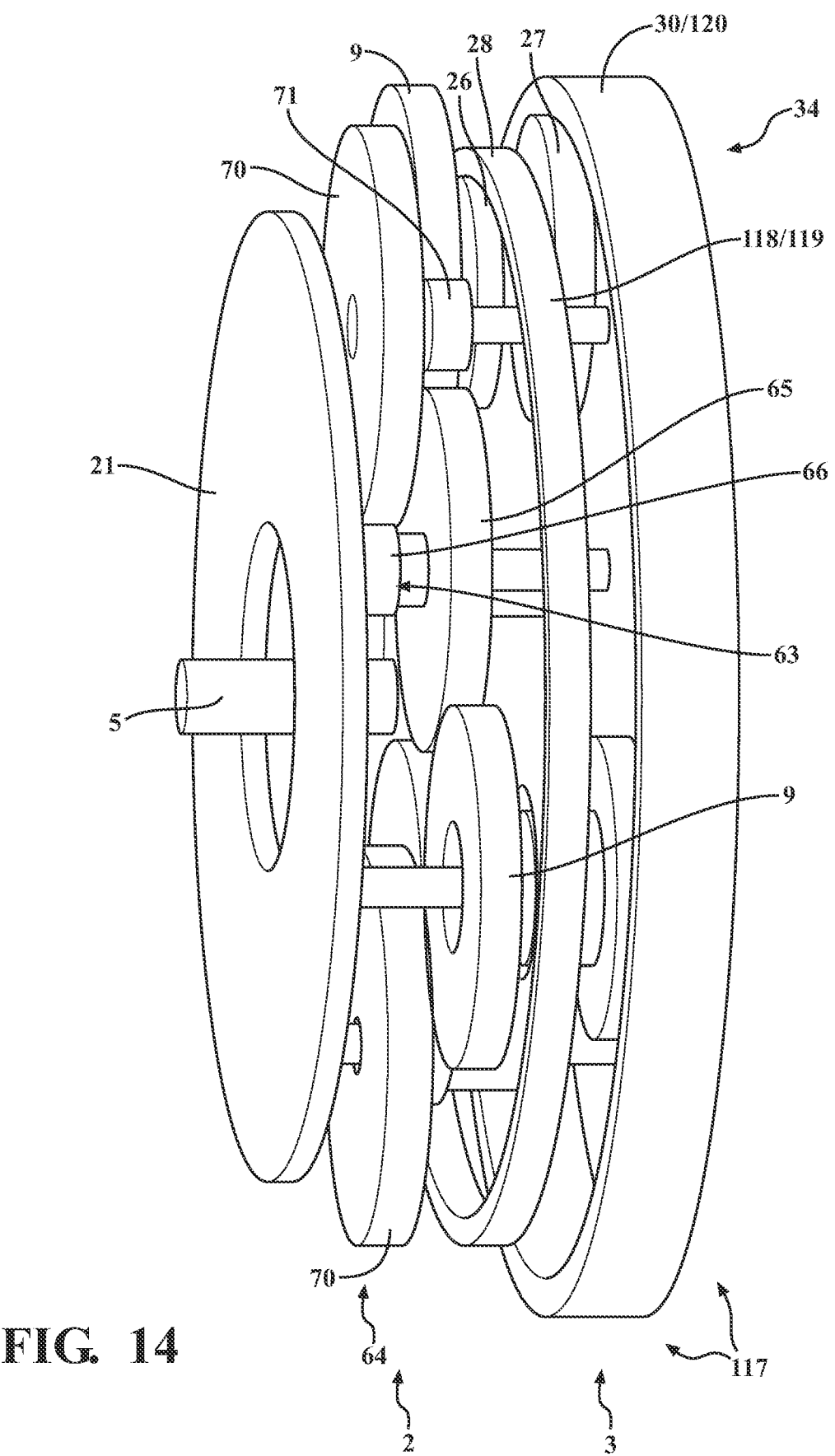
Figure 15:
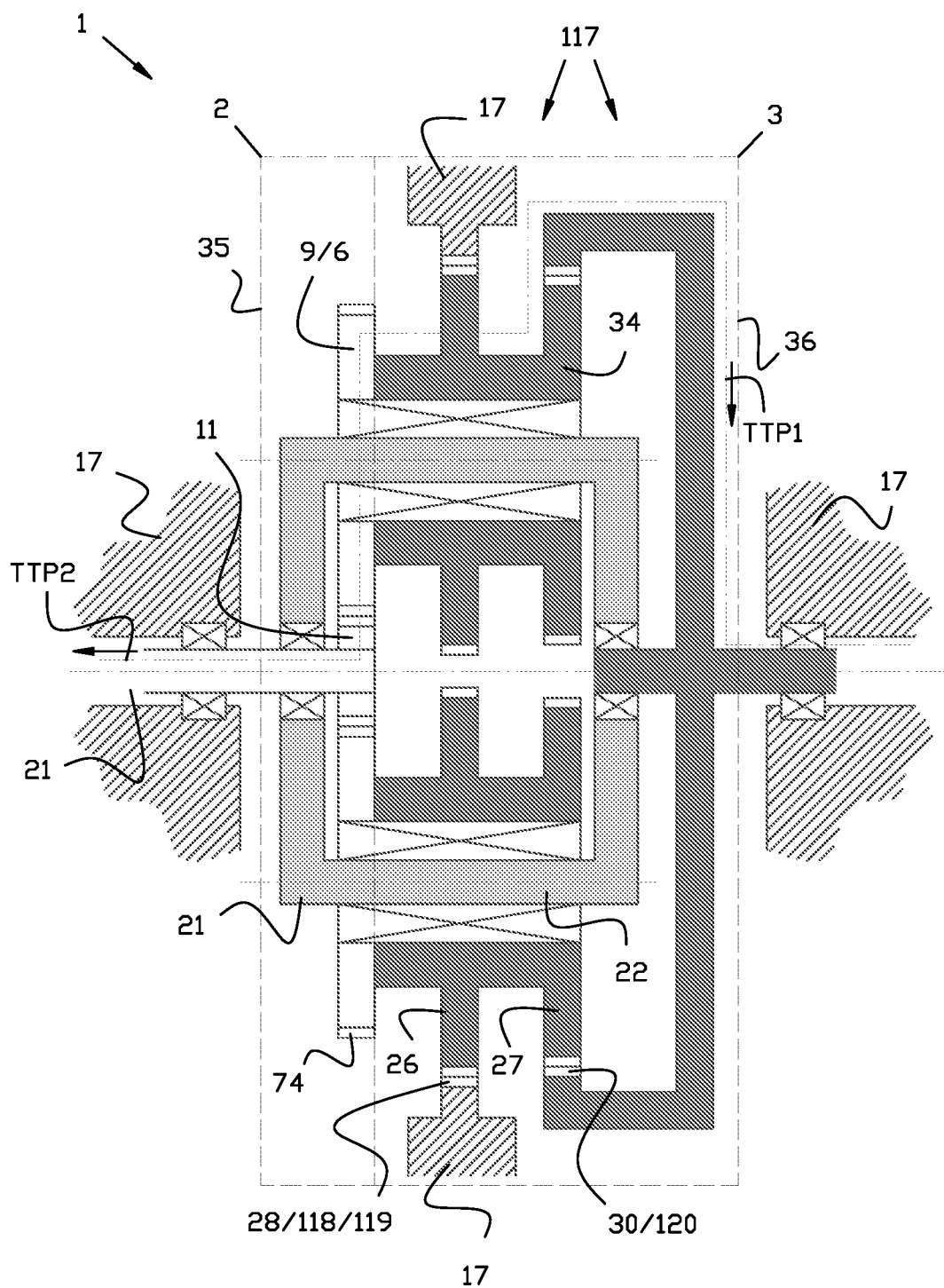
Figure 16:
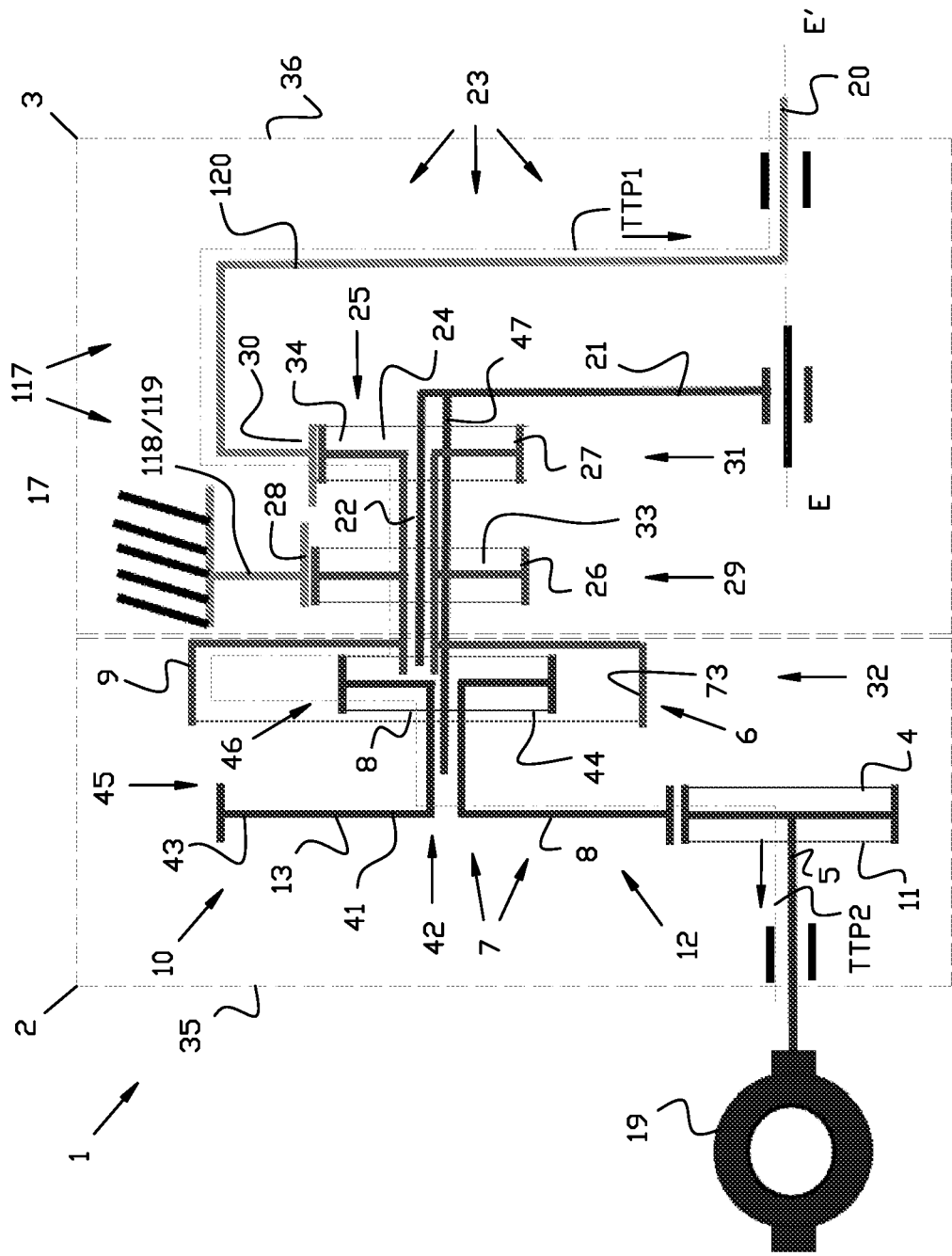
Figure 17:
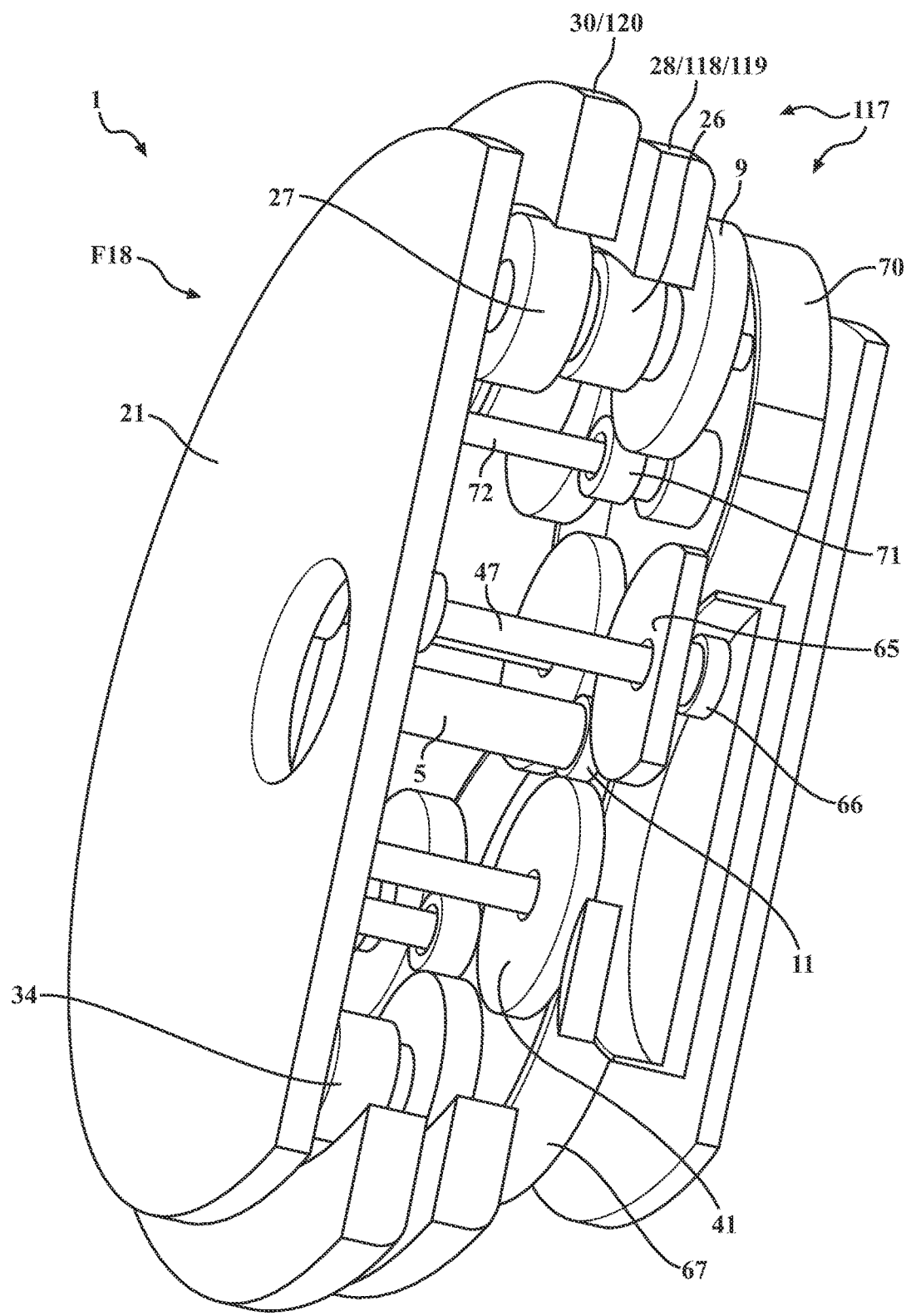
Figure 18:
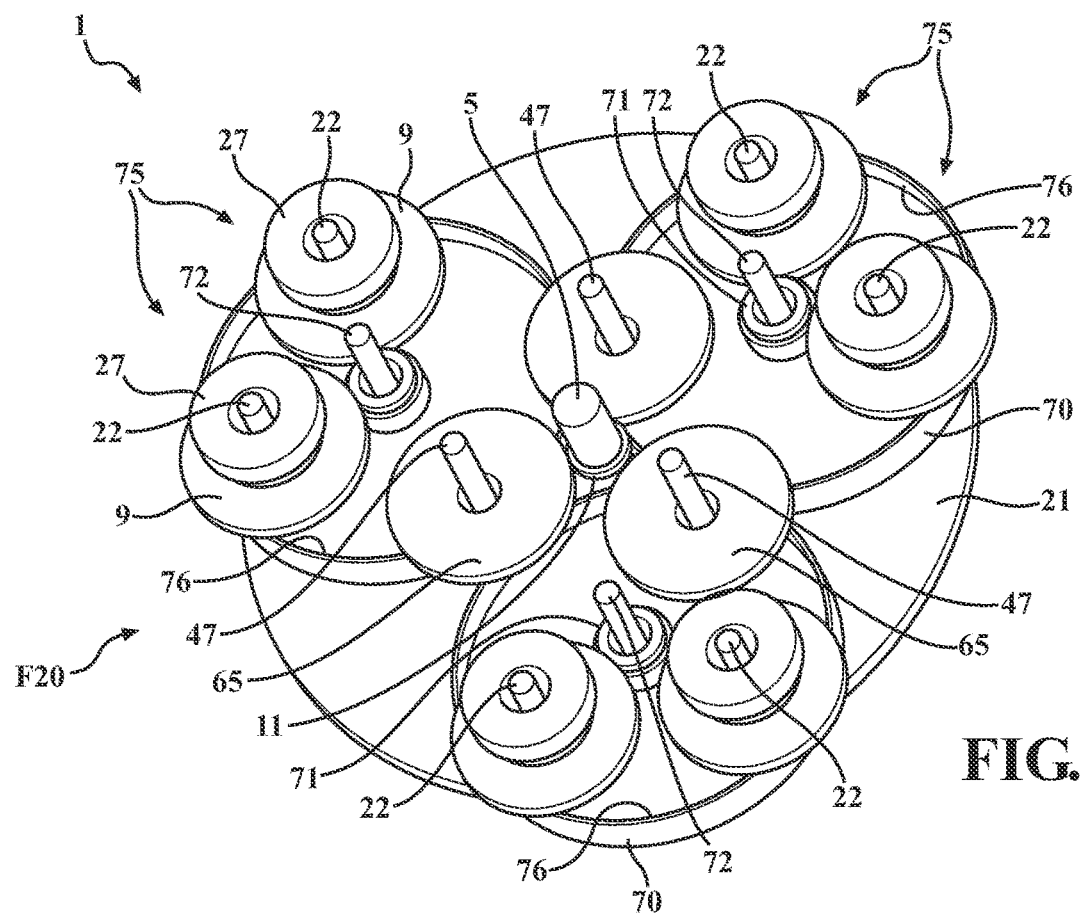
Figure 19:
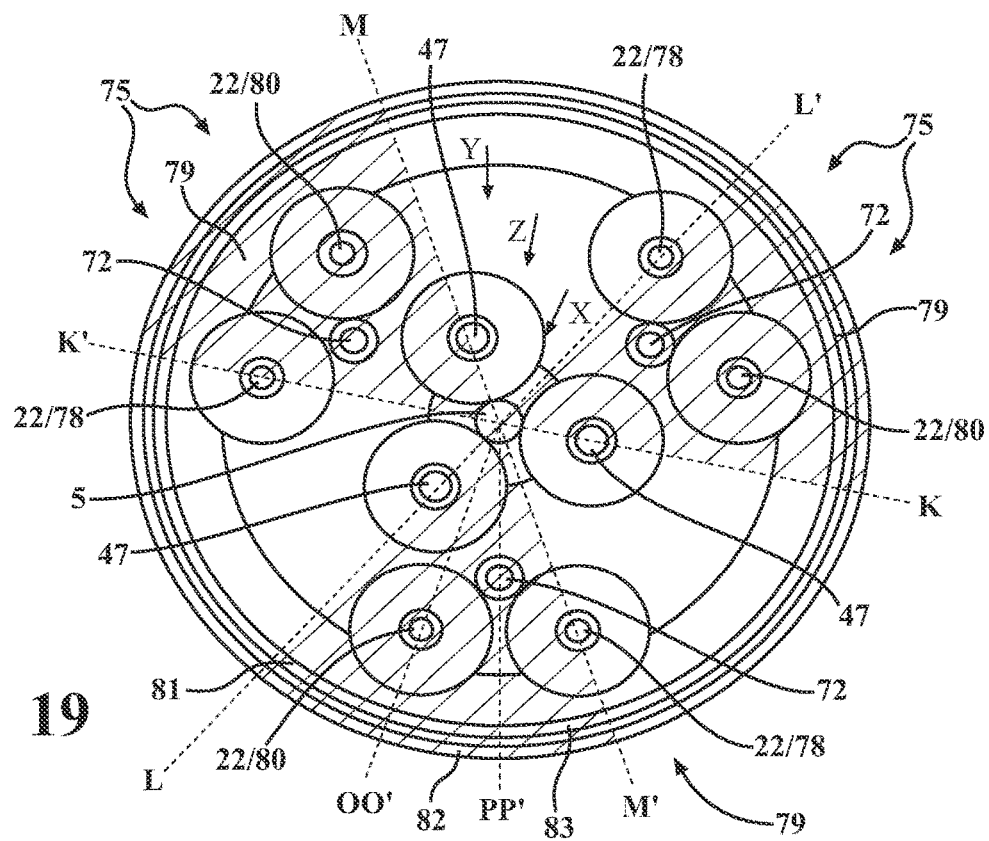
Figure 20:
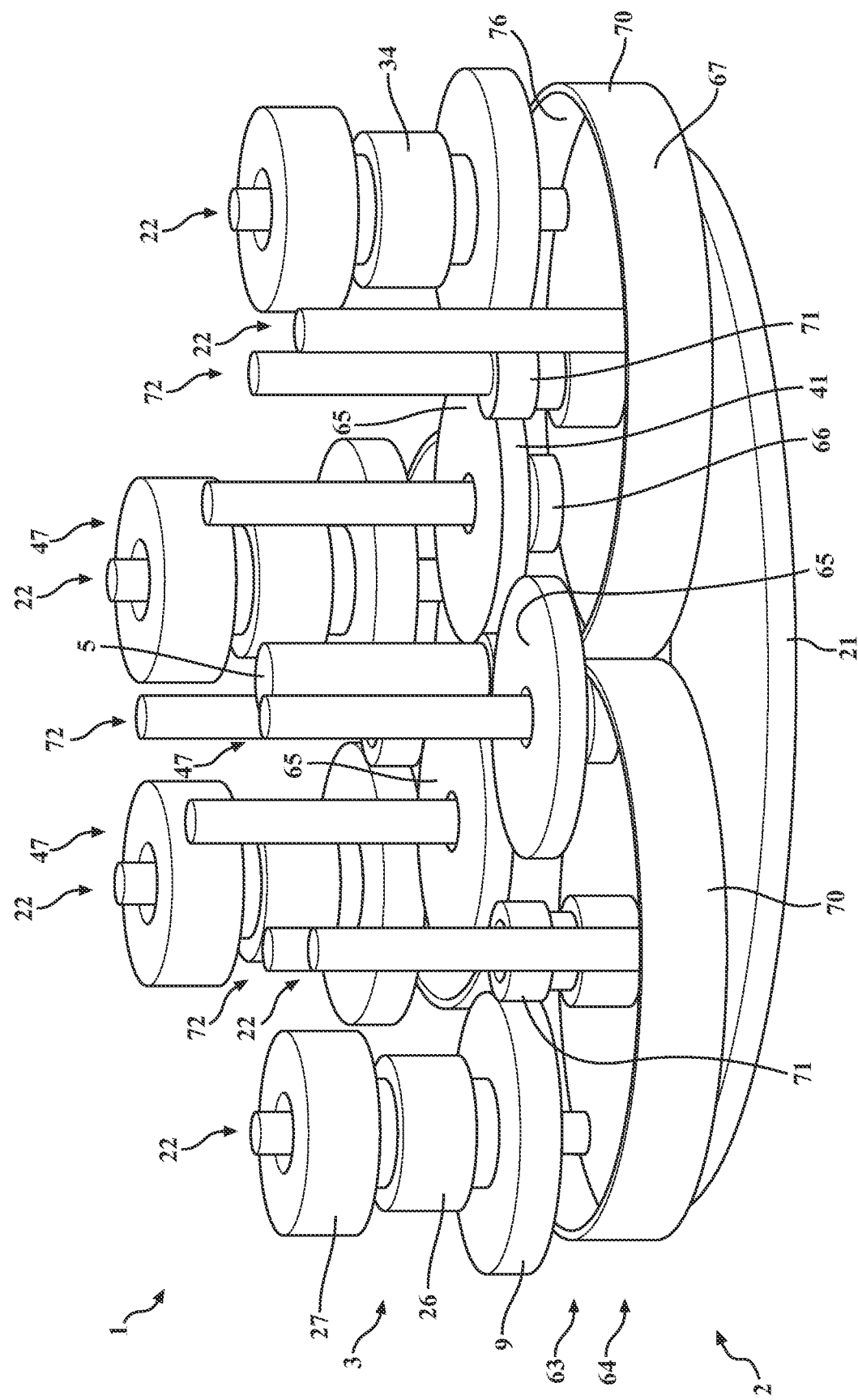
Figure 21:
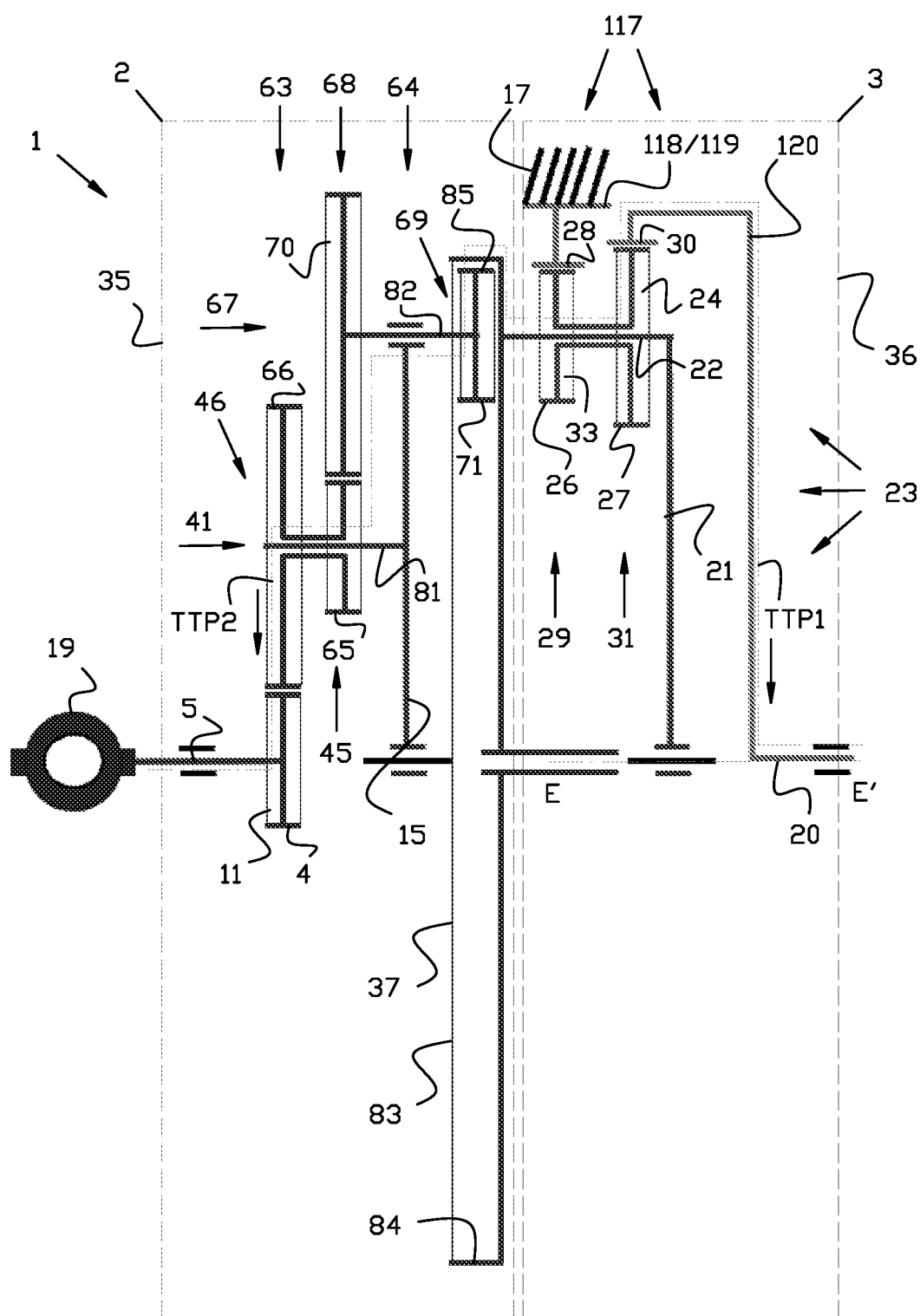
Figure 22:
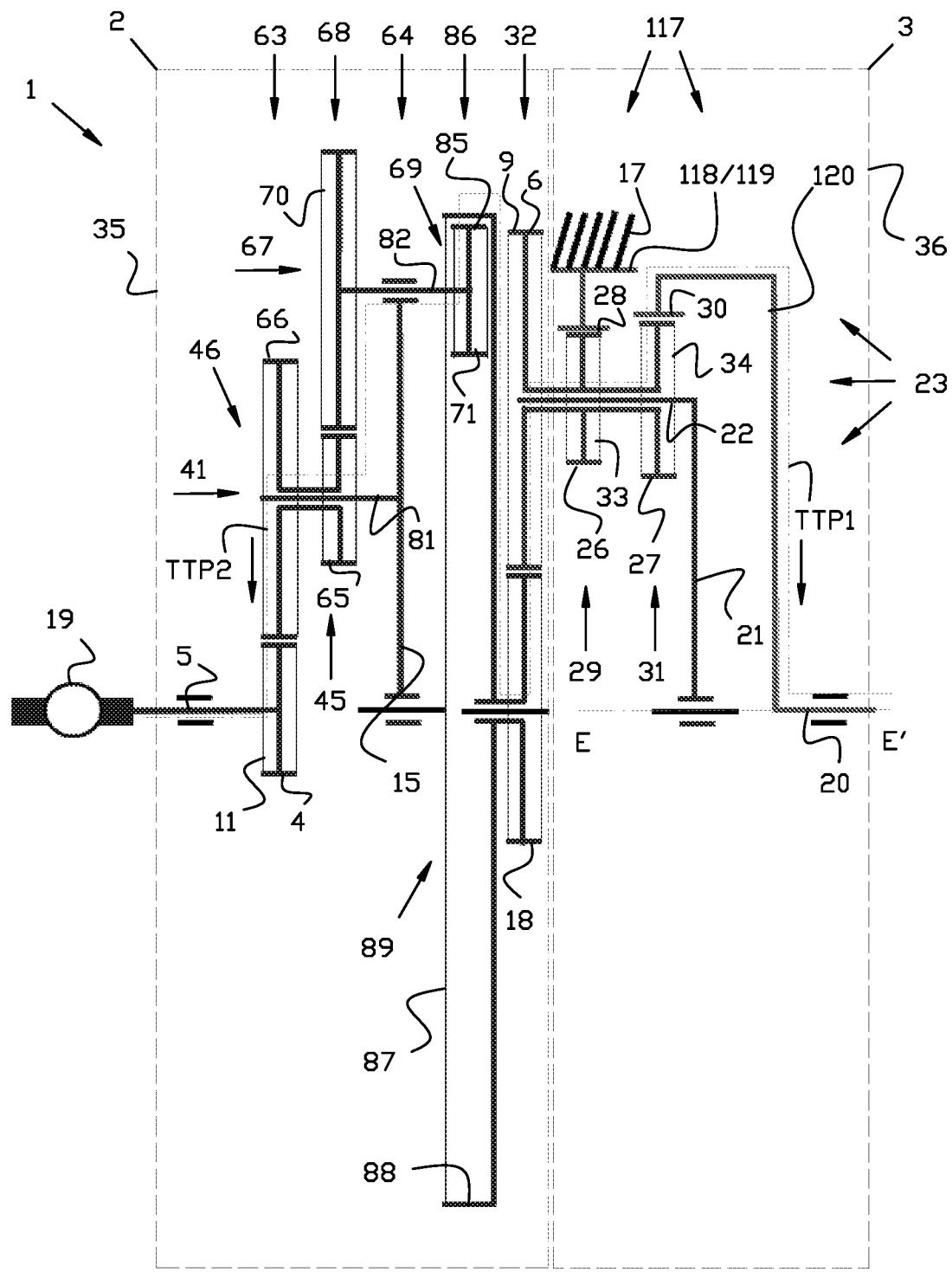
Figure 23:
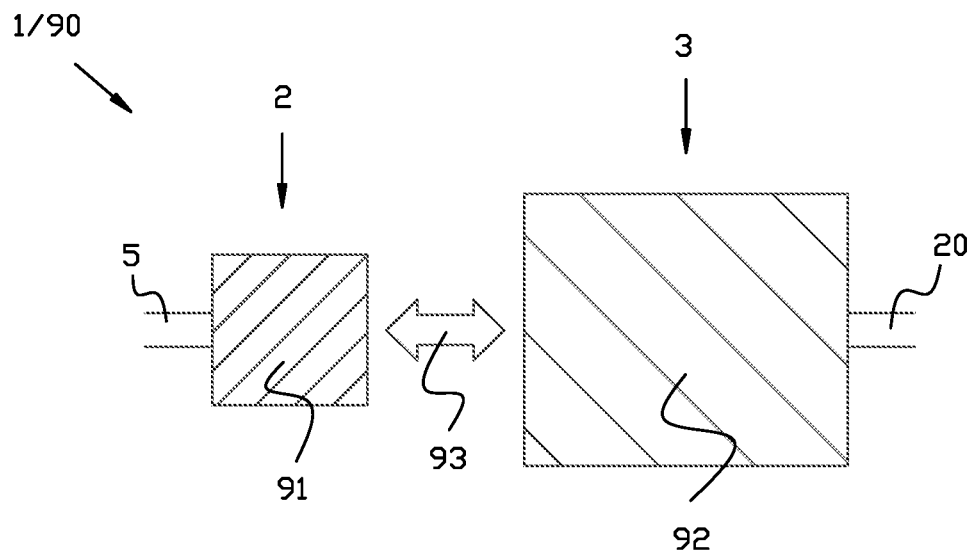
Figure 24:
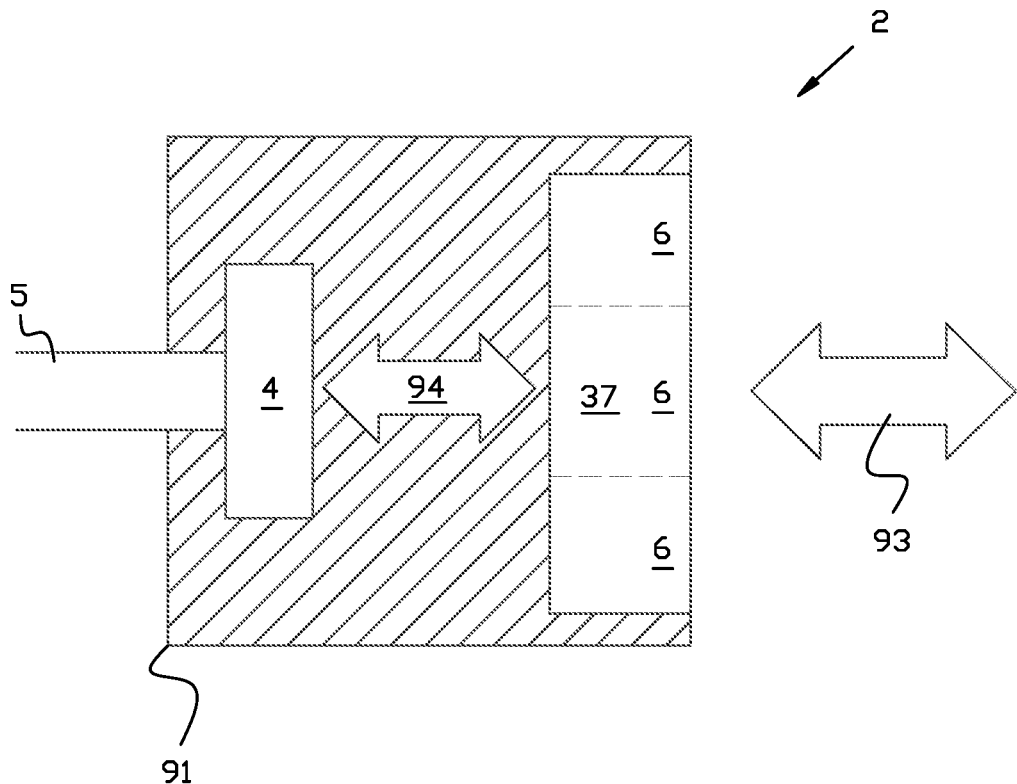
Figure 25:
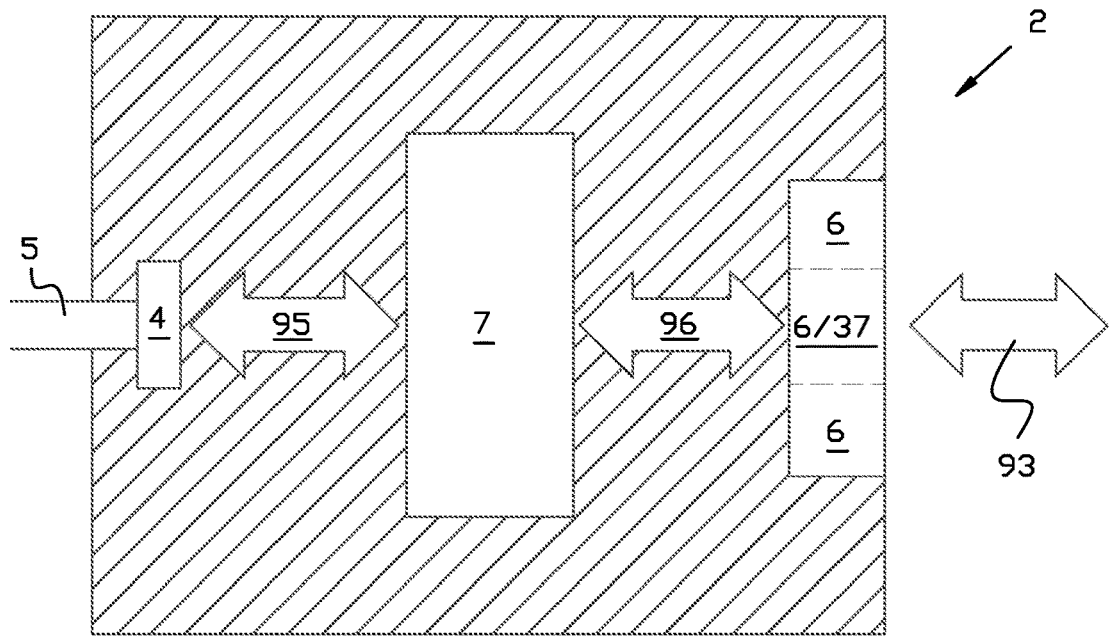
Figure 26:
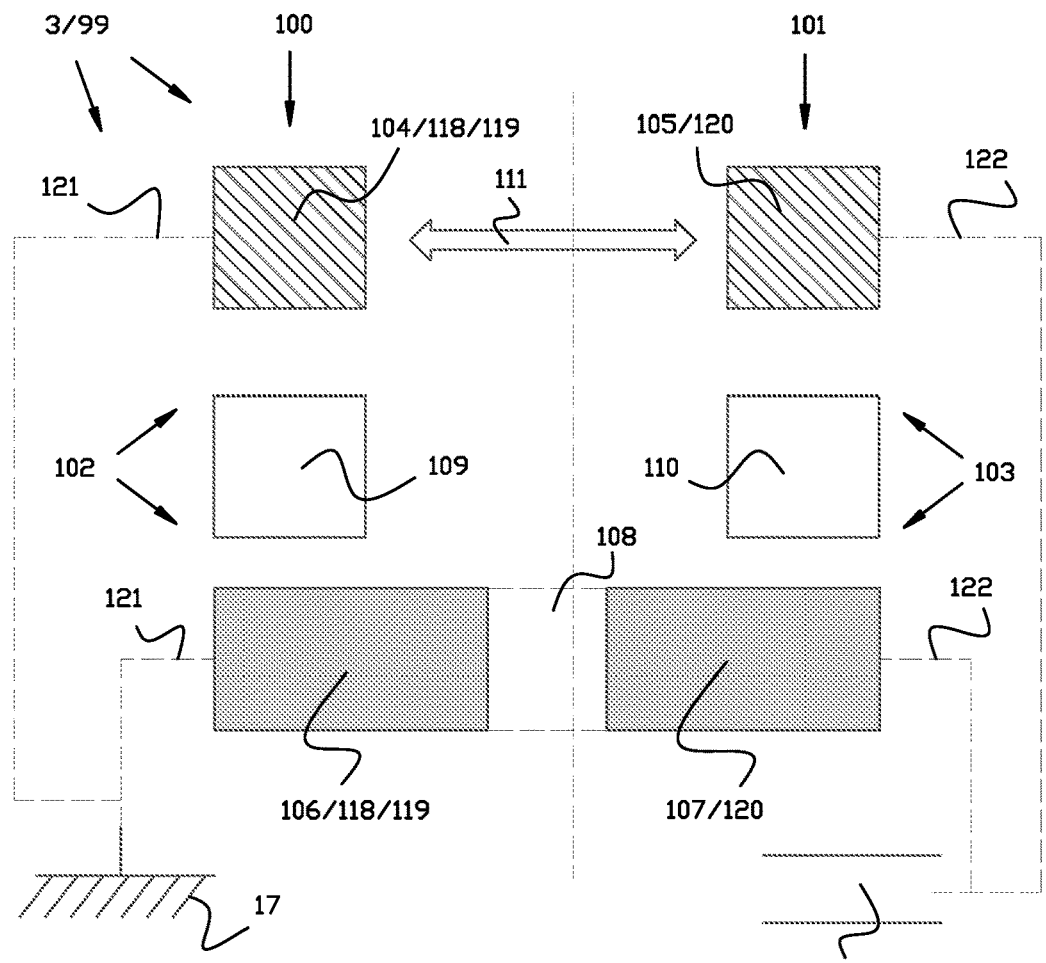
Figure 27:
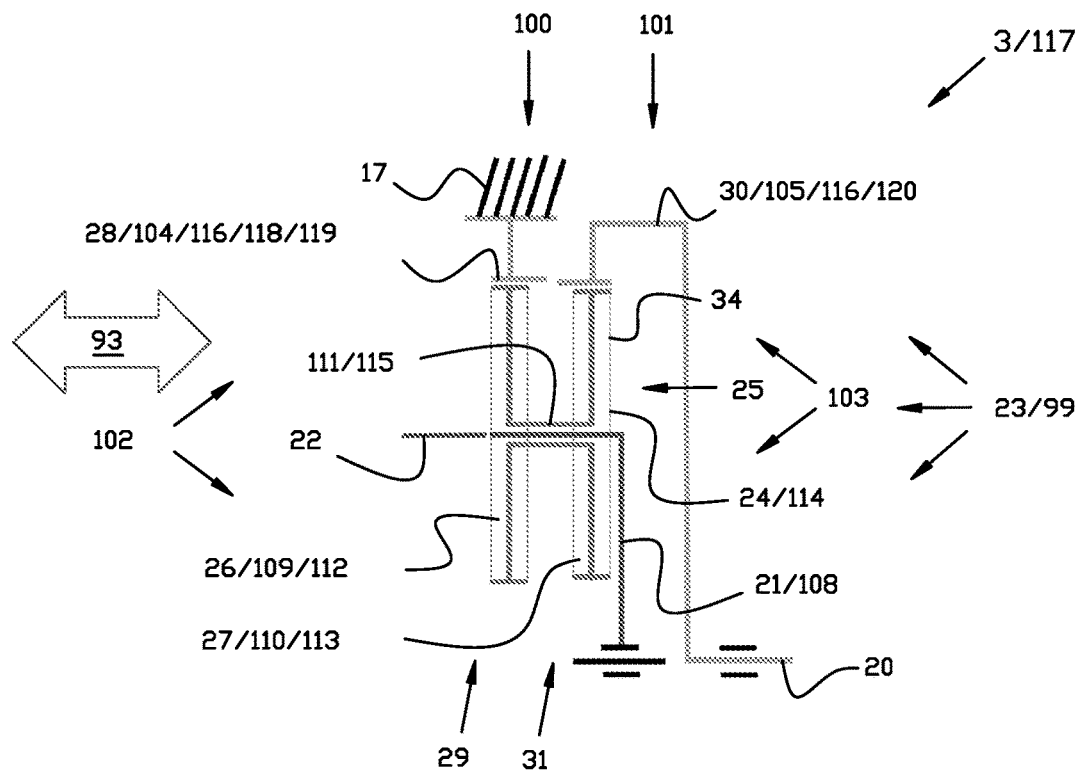
Figure 28:
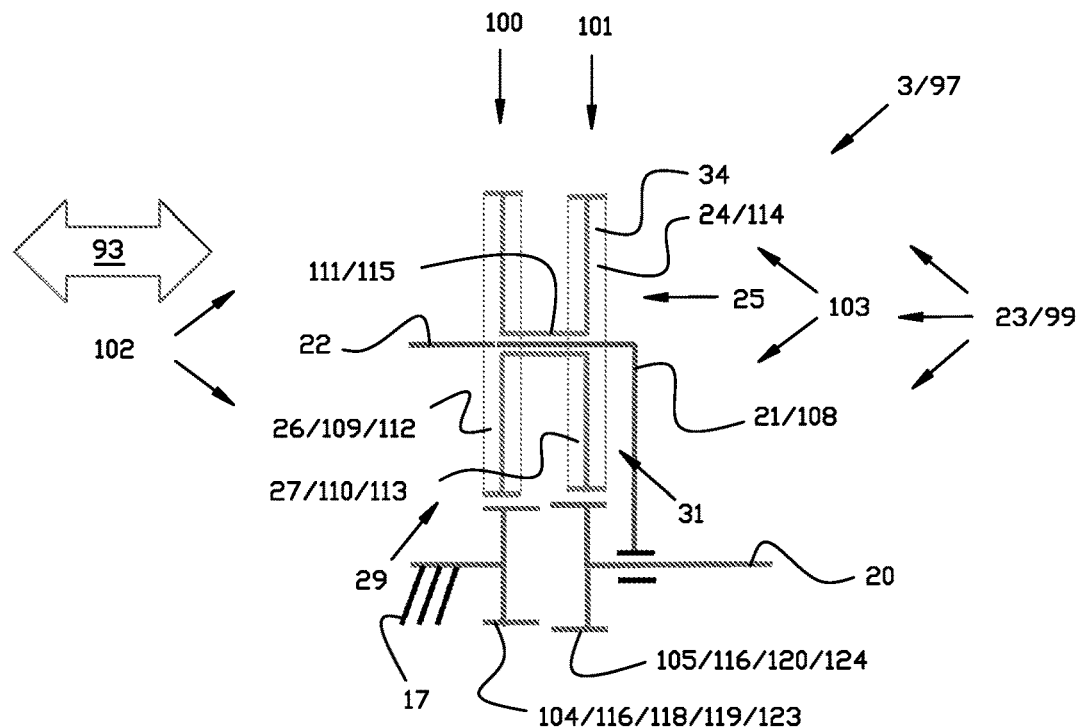
Figure 29:
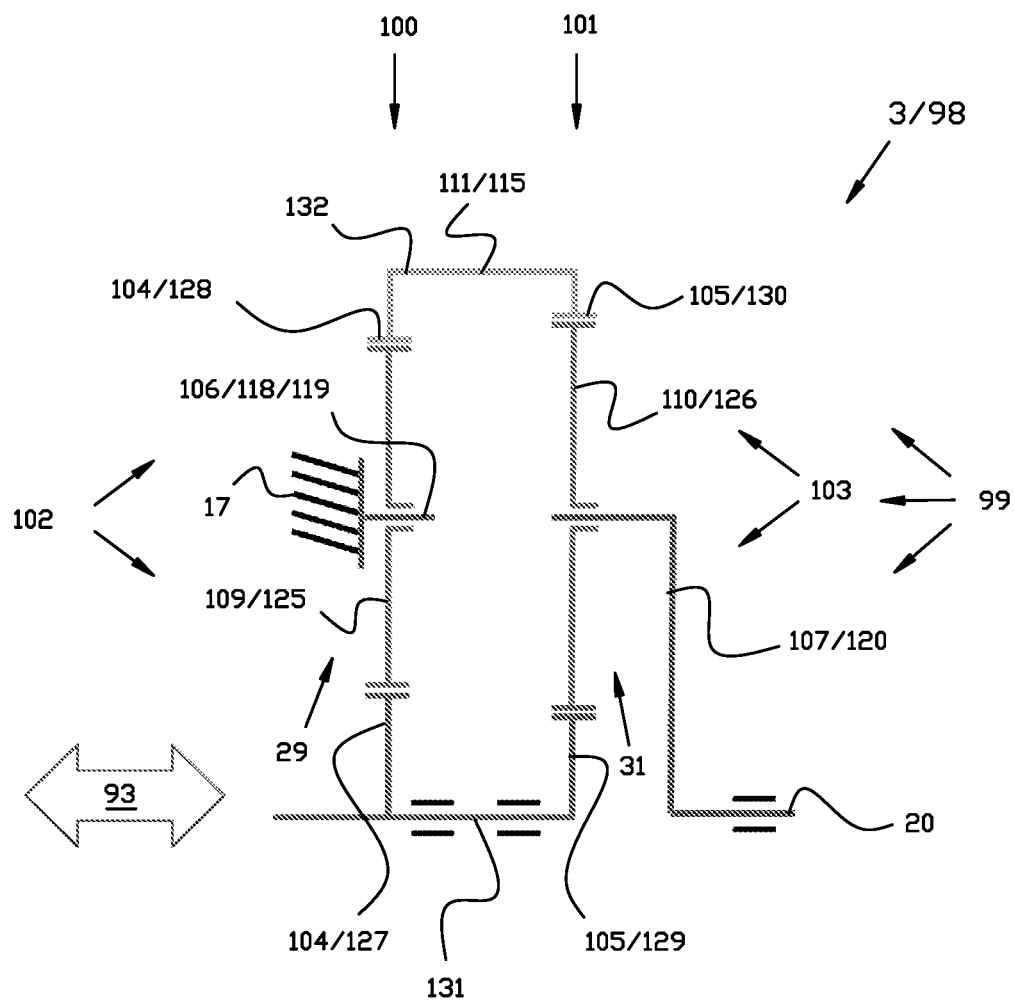
Figure 30:
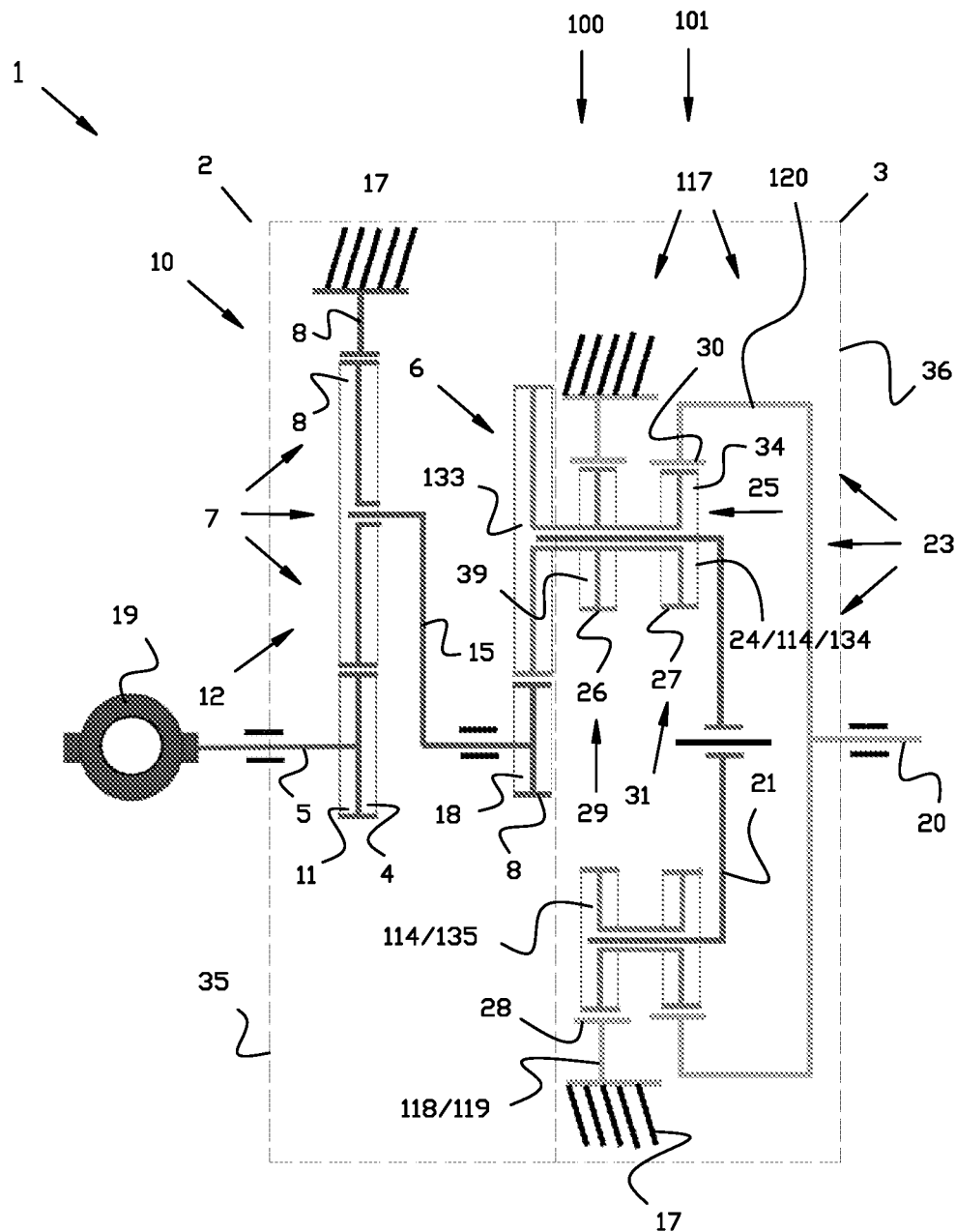
Figure 31:
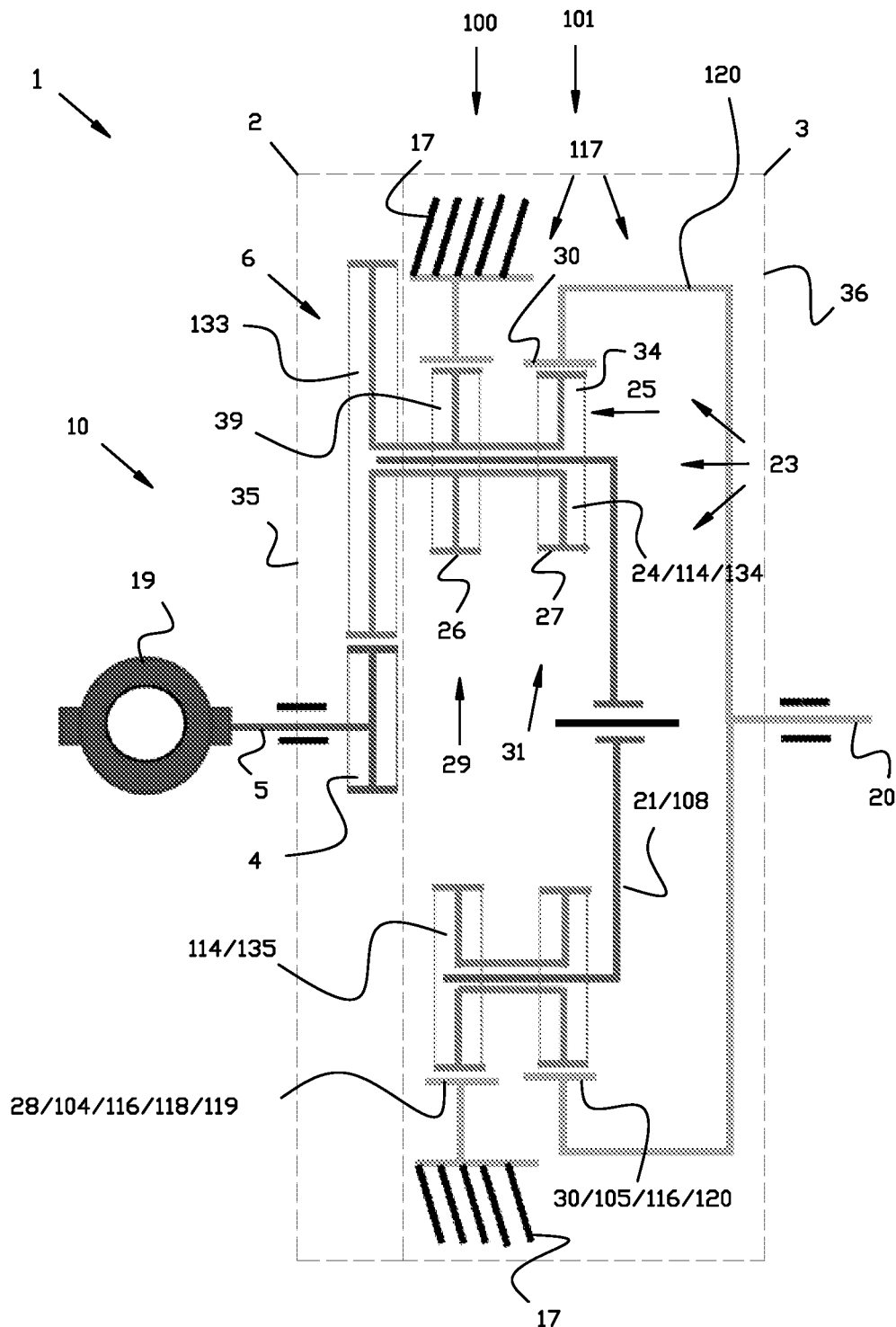
Figure 32:
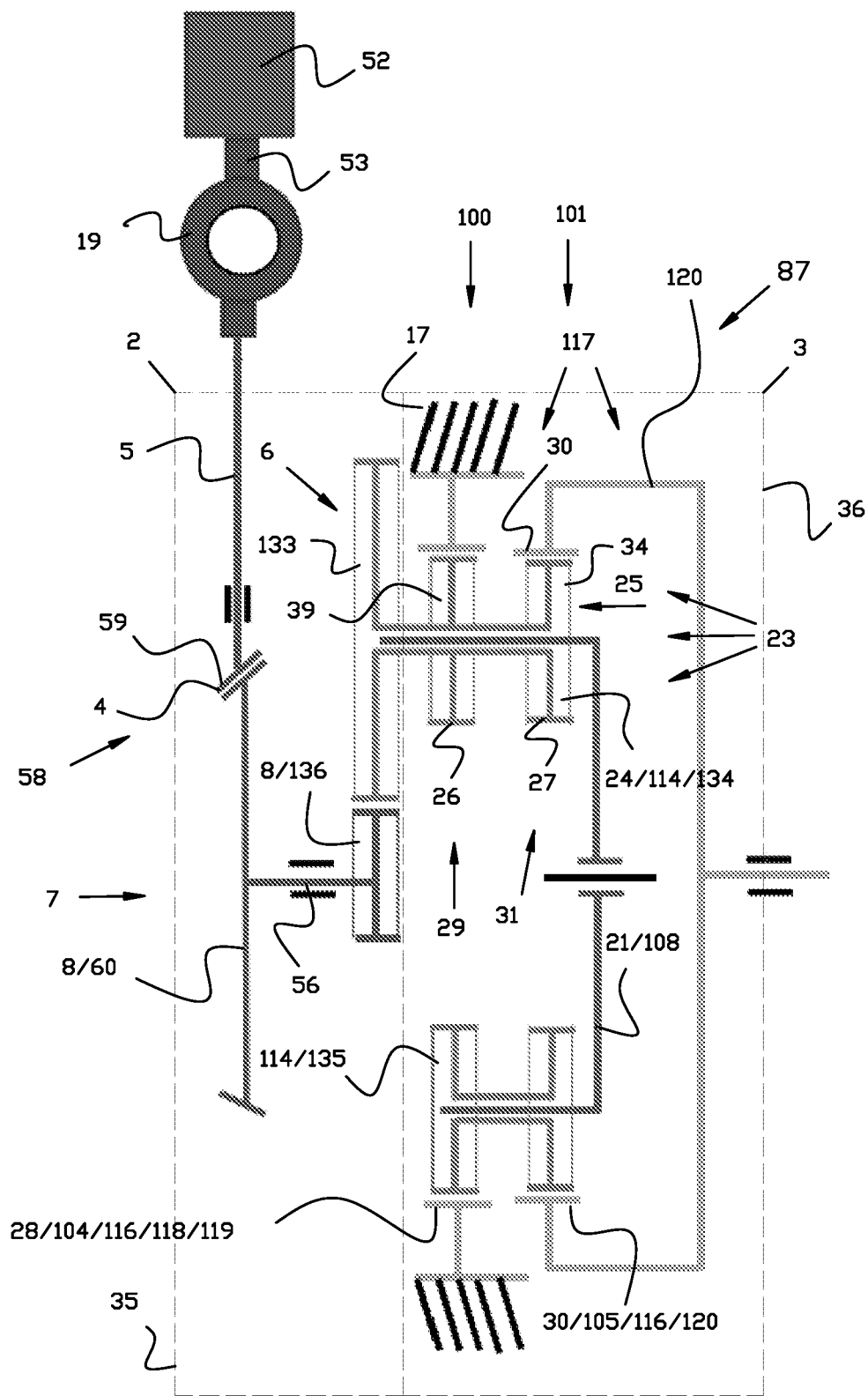

FIGS. 6 to 12 each represent still other embodiments of a gearwheel transmission in accordance with the invention;

FIG. 13 is a perspective view along arrow F13 of the embodiment represented in FIG. 12;

FIG. 14 is still another perspective view along arrow P14 of the embodiment represented in FIGS. 12 and 13;

FIG. 15 is a schematic view of a kind of generic embodiment of a gearwheel transmission in accordance with the invention;

FIG. 16 is a schematic view of still another embodiment of a gearwheel transmission in accordance with the invention;

FIG. 17 is a cross-sectional perspective view through a 3D model of still another embodiment of a gearwheel transmission in accordance with the invention;

FIG. 18 represents a perspective view on the embodiment of FIG. 17 along arrow F18, some parts being shown this time in full, while other parts are taken away for the sake of clarity;

FIG. 19 is a top view on the same embodiment of FIGS. 17 and 18;

FIG. 20 is another perspective view on the embodiment of FIG. 18 along arrow P20;

FIGS. 21 and 22 are schematic representations of still other embodiments of a gearwheel transmission in accordance with the invention;

FIG. 23 is a schematic block diagram giving a very general representation of a gearwheel transmission in accordance with the invention;

FIGS. 24 and 25 are two possible schematic representations of what a first stage of a gearwheel transmission in accordance with the invention in very general terms can be;

FIG. 26 is a schematic diagram representing a second stage of a gearwheel transmission in accordance with invention, again in a very general way;

FIGS. 27 to 29 are schematic illustrations of different more practically elaborated second stages of a gearwheel transmission in accordance with the invention; and, FIGS. 30 to 32 illustrate still other embodiments of a gearwheel transmission of the invention.

Figure 1:
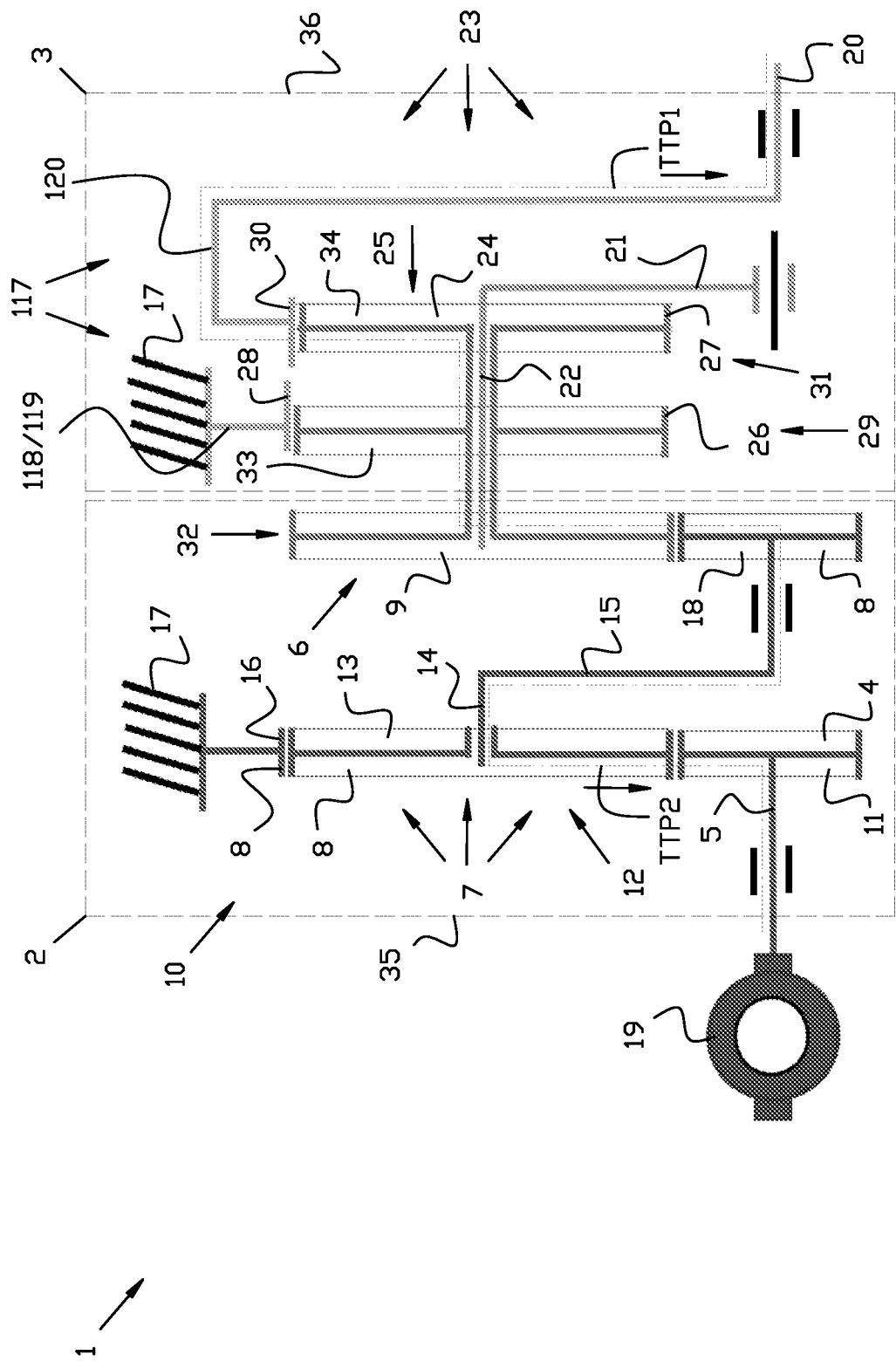
FIGS. 1 to 3 are schematic views of three different embodiments of a gearwheel transmission in accordance with the invention.

FIG. 1 represents a gearwheel transmission 1 according to the invention which has a high transmission ratio R, an improved efficiency W and increased capacity U for transmitting torque.

According to the invention such a gearwheel transmission 1 comprises a first stage 2 and a second stage 3 and in the examples that follow it will be described how these first stage 2 and second stage 3 can look alike.

The first stage 2 and the second stage 3 are in the drawings delimited by a dash-lined rectangle.

In general terms it can be said that the first stage 2 comprises in any case at least a first stage entry gearwheel 4 which is mounted fixedly on a first stage input shaft 5 of the gearwheel transmission 1 and this first stare entry gearwheel 4 is interacting for the transmission of rotational speed and torque with one or more first stage output elements 6, in a direct manner, indirectly through an interconnection mechanism 1 comprising one or more interconnection gearwheels 8.

In the example of FIG. 1, there are multiple first stage output elements 6 which are formed by a group of circumferentially spaced apart first stage output planetary gearwheels 9.

In this case, the first stage entry gearwheel 4 is clearly not interacting in a direct manner with these multiple first stage output elements 6, but through an interconnection mechanism 7.

In particular, in the embodiment of FIG. 1, the first stage 2 comprises a first stage planetary type gearwheel assembly 10, wherein the first stage entry gearwheel 4 is a first stage entry sun wheel 11 of the first stage planetary type gearwheel assembly 10.

The first stage planetary type gearwheel assembly 10 furthermore comprises a group 12 of circumferentially spaced apart first stage planetary gearwheels 13 provided concentrically around the first stage input shaft 5.

Each first stage planetary gearwheel 13 of this group 12 of first stage planetary gearwheels 13 interacts or intermeshes with the first stage entry sun wheel 11.

Furthermore, the first stage planetary gearwheels 13 are each supported by a first stage planetary gear shaft 14 in a rotatable manner, for example by means of roller bearings, or by being fixedly connected to the concerned first stage planetary gear shaft 14.

Moreover, the first stage planetary gear shafts 14 are fixedly mounted on a first stage planetary carrier 15 circumferentially spaced apart and concentrically with the first stage input shaft 5, i.e. in the case of a rotatable support of the first stage planetary gearwheels 13 on their respective first stage planetary gear shaft 14.

In the case the first stage planetary gearwheels 13 are fixedly connected to their respective first stage planetary gear shaft 14 the first stage planetary gear shafts 14 should be mounted in a rotatable manner on the first stage planetary carrier 15, for example by means of bearings suitable for this purpose.

The first stage planetary gearwheels 13 are each also intermeshing with a first stage fixed ring wheel 16 which is concentric with the first stage input shaft 5 and which is fixedly connected to a housing 17 of the gearwheel transmission 1.

The afore-mentioned first stage planetary carrier 15 is furthermore fixedly interconnected with an additional first stage outlet sun wheel 18, which is axially aligned with the first stage input shaft 5.

This first stage outlet sun wheel 18 is intermeshing with every one of the first stage output elements 6, which are in the represented case first stage output planetary gearwheels 9.

In the case of FIG. 1 the interconnection mechanism 7 comprises the housing 17, the first stage planetary carrier 15, as well as the interconnection gearwheels 8 represented by the first stage fixed ring wheel 16, the group 12 of first stage planetary gearwheels 13 and the first stage outlet sun wheel 18.

The gearwheel transmission 1 also comprises an actuator 19 which is mounted at the first sage input shaft 5 for driving the first stage input shaft 5 in a rotatable manner.

The gearwheel transmission 1 is intended for transmission of torque and rotational speed between the first stage input shaft 5 and a second stage output shaft 20 of the second stage 3.

It is therefore provided with an intermediate planet carrier 21, which is mounted in a rotatable manner in the housing 17 and which is separated from the first stage input shaft 5 as well as from the second stage output shaft 20.

This intermediate planet carrier 21 is concentric with the second stage output shaft 20 and is mounted in this case in a rotatable manner for a rotating movement around this second stage output shaft 20.

Furthermore, a number N of circumferentially spaced apart intermediate carrier planetary gearwheel shafts 22 are provided on said intermediate planet carrier 21, which are mounted fixedly or in a rotatable manner on the intermediate planet carrier 21.

In the example of FIG. 1 the intermediate planet carrier 21 and the intermediate carrier planetary gearwheel shafts 22 extend mainly in the section of the gearwheel transmission 1 corresponding to the section which comprises the second stage 3, but in other embodiments the intermediate planet carrier 21 and the intermediate carrier planetary gearwheel shafts 22 could as well extend with important parts into the section of the gearwheel transmission 1 which comprises mainly the first stage 2.

The second stage 3 of the gearwheel transmission 1 in accordance with the invention comprises a second stage compound planetary type gearwheel assembly 23.

First of all, this second stage compound planetary type gearwheel assembly 23 comprises second stage compound planetary gearwheels 24 which are each supported on a corresponding primary, intermediate carrier planetary gearwheel shaft 22 of the intermediate planet carrier 21.

Each such second stage compound planetary gearwheel 24 comprises a series 25 of, in the represented example, only two, fixedly interconnected, stepped second stage planetary gearwheels 26 and 27.

Hereby, each primary, intermediate carrier planetary gearwheel shaft 22 is providing support for a corresponding second stage compound planetary gearwheel 24.

This support is realized either in a rotatable manner, for example by means of roller bearings or in a fixed manner, in which case each primary, intermediate carrier planetary gearwheel, shaft 22 is fixedly interconnected with the concerned series 25 of second stage planetary gearwheels 26 and 27.

The second stage compound planetary type gearwheel assembly 23 furthermore comprises a second stage fixed ring wheel 28 which is concentric with the second stage output shaft 20 and which is fixedly connected to the housing 17 of the gearwheel transmission 1.

This second stage fixed ring wheel 28 is intermeshing with a first group 29 of circumferentially spaced apart second stage planetary gearwheels 26 composed by the first planetary gearwheel 26 of each afore-mentioned series 25 of second stage planetary gearwheels 26 and 27.

The second stage compound planetary type gearwheel assembly 23 also comprises a second stage rotatable ring wheel 30 which is concentric with the second stage output shaft 20, which is mounted in a rotatable manner in the housing 17, and which is fixedly connected to the second stage output shaft 20.

This second stage rotatable ring wheel 30 is intermeshing with a second group 31 of circumferentially spaced apart second stage planetary gearwheels 27 composed by the second planetary gearwheel 27 of each afore-mentioned series 25 of second stage planetary gearwheels 26 and 27.

Of course, the first stage 2 and the second stage 3 of the gearwheel transmission 1 are interconnected and/or are interacting with one another for transmission of torque and rotational speed between the first stage input shaft 5 and the second stage output shaft 20.

In this case of FIG. 1, the first stage 2 and the second stage 3 are interconnected to one another and are axially positioned adjacent to one another.

Indeed, the first stage output elements 6 are formed by a group 32 of circumferentially spaced apart first stage output planetary gearwheels 9 which are each interconnected with or form a monolithic part with a corresponding planetary gearwheel 26 of a group 29 of circumferentially spaced apart second stage planetary gearwheels 26 of the second stage compound planetary type gearwheel assembly 20.

These second stage planetary gearwheels 26 represent in this e ample second stage input elements 33.

This situation corresponds to the third interconnection configuration for interconnection between the first stage 2 and second stage 3, mentioned above and in claim 1.

This situation can also be considered in another way, namely that from a structural point of view actually each compound planetary gearwheel 24 comprises a series 25 of three planetary gearwheels, composed of a pair of second stage planetary gearwheels 25 and 26 and a first stage planetary gearwheel 9.

In that way, actually a group of hybrid, compound planetary gearwheels 34 is formed, each comprising a series 25 of three planetary gearwheels, composed of a pair of second stage planetary gearwheels 26 and 27 and, a first stage output planetary gearwheel 9.

The hybrid character of the compound planetary gearwheels 34 is first of all a consequence of the definition of the first stage 2 and the second stage 3 used in this text.

Therefore, the second stage planetary gearwheels 26 and 27 as well as the first stage output planetary gearwheels 9 can in principle be executed in the same manner, their execution parameters set to the same values.

Nevertheless, typically this will not be the case and as is also the case in the embodiment represented in FIG. 1, the first stage output planetary gearwheels 9 are executed with some execution parameters set to different parameter values than the second stage planetary gearwheels 26 and 27.

The gearwheels of the first stage 2 and the second stage 3 are both executed according to a set of execution parameters, and the first stage 2 and the second stage 3 are in this example, apart from different in structure, also different in nature in that one or more execution parameters of this set have parameter values which are different in the first stage 2 compared to the corresponding parameters values in the second stage 3 and this in such a way that the difference is towards increased efficiency in the first stage 2 and towards increased capacity for transmitting torque in the second stage 3, compared relatively to one another.

In short, in this example the components of the first stage 2 are all executed in a certain way which is different from the way the components of the second stage 3 are executed.

As a matter of fact, the gearwheel transmission 1 represented in figure is a particular application of the more general principle that there should by a difference in execution so that the first stage 2 has a higher overall efficiency than the second stage 3 and/or the second stage 3 has a higher overall capacity for transmitting torque than the first stage 2.

This principle can also be obtained by having different components in each stage being executed in a different manner.

According to another principle in accordance with the invention, there could be certain gearwheels of the gearwheel transmission 1, regardless what their position is in the gearwheel transmission 1, which are executed with execution parameters set to different parameter values in such a way that transmission efficiency is increasing towards the first stage input shaft 5 and/or capacity for transmitting torque is increasing towards the second stage output shaft 20, compared relatively to one another.

In particular at least the gearwheels, but possibly also other elements such as planetary carriers, of the first stage 2 and the second stage 3 are executed according to a set of execution parameters which influence transmission efficiency and/or capacity for transmitting torque.

Hereby, some gearwheels of the gearwheel transmission 1 can be executed with their execution parameters set to different parameter values, in such a way that following a torque transmission path TTP1 through the gearwheel transmission 1 from the first stage input shaft 5 towards the second stage output shaft 20 the difference in execution is such that the capacity for transmitting torque of the concerned gearwheels is increasing, while when following a torque transmission path TTP2 through the gearwheel transmission 1 from the second stage output shaft 20 towards the first stage input shaft 5 the difference in execution is such that the efficiency of transmission realized by the concerned gearwheels is increasing.

In the example of FIG. 1, the totality of gearwheels of the first stage 2 are executed in a certain way and the totality of gearwheels of the second stage 3 are executed in a certain other way by setting some execution parameters to parameter values which are different from parameter values used in the first stage 2.

The reason why in the case of FIG. 1 the parameter values are chosen to make the first stage 2 more efficient or what is the same, optimized for reducing energy losses such as due to friction losses and rolling work, and the second stage is optimized for having a higher torque transmission capacity, is that according to preferred characteristics of the invention the first stage 2 is a high speed-low torque stage 35 and the second stage 3 is a low speed-high torque stage 36, compared relatively to one another.

Hereby, the first stage 2 comprises first stage gearwheels 4, 9, 13 and 18 interacting with one another for transmitting rotational speed of and torque delivered at the first stage input shaft 5 into a decreased rotational speed of and an increased torque at one or more first stage output elements 6, represented in FIG. 1 by the first stage output planetary gearwheels 9.

The second stage 3 comprises second stage gearwheels 26, 27, 28 and 30 interacting with one another for transmitting rotational speed of and torque at one or more second stage input elements 33, represented in the case of FIG. 1 by the group 29 of second stage planetary gearwheels 26, into rational speed of and torque at the second stage output shaft 20.

In this second stage 3 the rotational speed at the second stage input elements 33, which is already relatively low compared to the rotational speed provided by the actuator 19 at the first stage input shaft 5, is still more decreased towards the second stage output shaft 20 and the torques get higher and higher in the same time.

The first stage output elements 6 or 3 are in this case each interconnected with a corresponding element 26 of the second stage input elements 33 for the transmission of torque and rotational speed, but other interactions between the first stage output elements 6 and the second stage input elements 33 are not excluded from the invention.

In such a configuration it makes a lot of sense to choose first parameter values of certain execution parameters for the first stage 2 and second parameter values of the corresponding execution parameters for the second stage 3 which differ from one another in such a way that the first parameter values increase efficiency in a high speed-low torque mechanical rearing 35, while the second parameter values increase robustness, strength and/or capacity to transmit torque in a low speed-high torque mechanical gearing 36, compared relatively to one another.

Indeed, in the first stage 2 it is not so important that the concerned elements are very strong since torques are relatively low.

On the other hand, the rotational speeds are relatively high in the first stage 2, so that gearwheels are traveling rather long distances over one another in a short time, which is an important factor in the rolling work and which is causing a lot of friction losses, so that it is important in this first stage 2 to increase the efficiency, for example by using smooth materials for reducing friction losses, by using light materials for reducing dynamic or inertia losses, by applying relatively smaller interaction forces between gearwheels for reducing the implied rolling work, by adapting the profile shift of the concerned gearwheels accordingly, and so on.

In the second stage 3 the opposite is true so that in this stage 3 it is more important to increase the capacity to transmit torque, for example by using gearwheels with more rough surfaces, using stronger and heavier materials, adapting the profile shifts of gearwheels so to increase the contact force between the concerned gearwheels, and so on.

In the case represented in FIG. 1, the first stage 2 and the second stage 3 differ in nature in that their gearwheels are executed in different ways, so that the gearwheel transmission 1 comprises only two blocks of differently executed gearwheels, which in this example, correspond respectively to the block of gearwheels which form the first stage 2 and the block of gearwheels which form the second stage 3.

In this example, there is an increase in efficiency in a direction towards the first stage input shaft 5 which consists of a single step increase which takes place at the separation between the second stage 3 and the first stage 2 and/or there is an increase in capacity for transmitting torque in a direction towards the second stage output shaft 20 which consists of a single step increase which takes place at the separation between the first stage 2 and the second stage 3.

Of course, in other embodiments of a gearwheel transmission in accordance with the invention gearwheels can be differently executed with their parameter values set to different values, the concerned gearwheels being positioned within a single stage 2 or 3 or overlapping these stages 2 and 3, and a trend of increasing capacity for transmitting torque or of increasing efficiency can consist of a single step or multiple steps.

These trends are usually respectively in a direction towards the second stage output shaft and in a direction towards the first stage input shaft, but inside each stage exceptions to this general rule are also possible as long as the overall efficiency is higher in the first stage 2 compared to the overall efficiency in the second stage 3, and/or the overall capacity for transmitting torque is higher in the second stage 3 compared to this overall capacity for transmitting torque in the first stage 2.

Elements of the first stage 2 and elements of the second stage 3 can for example both be executed by taking a set of execution parameters into account, which comprises for example the following execution parameters (MOD; QL; ACC; PS; CR; TS; FP; MA; RG; SH):
 a module MOD of a gearwheel or pair of gearwheels;
 a quality level of a gearwheel or pair of gearwheels;
 an accuracy of a gearwheel or pair of gearwheels;
 a profile-shift PS of a gearwheel or pair of gearwheels;
 a contact ratio CR of a gearwheel or pair of gearwheels;
 a tooth geometry TG applied in a gearwheel or pair of gearwheels;
 a filet profile FP applied in a gearwheel or pair of gearwheels;
 a material MA used for making a gearwheel or pair of gearwheels;
 a roughness RG applied in a gearwheel or pair of gearwheels; and,
 a surface hardness al applied in a gearwheel or pair of gearwheels.

According to the invention it is however not excluded to take more or less of such kind of execution parameters into account, when developing the gearwheel transmission 1.

For example, first elements can be executed with their execution parameters (MOD; QL; ACC; PS; CR; TG; FP; MA; RG; SH) set to certain first parameter values (MOD_PV1; QL_PV1; ACC_PV1; PS_PV1; CR_PV1; TG_PV1; FP_PV1; MA_PV1; RG_PV1; SH_PV1).

Similarly, second elements can for example be executed with their execution parameters (MOD; QL; ACC; PS; CR; TG; FP; MA; RG; SH) set to second parameter values (MOD_PV2; QL_PV2; ACC_PV2; PS_PV2; CR_PV2; TG_PV2; FP_PV2; MA_PV2; RG_PV2; SH_PV2).

Each of the first parameter values and the second parameter values can be different, but this is not necessarily the case, but when a first parameter value PV1 and the corresponding second parameter value PV2 are different, they should be different such that the overall efficiency in the first stage 2 is increased with respect to the overall efficiency in the second stage 3 and/or the overall capacity of transmitting torque is increased in the second stage 3 with respect to the first stage 2.

According to another possible principle efficiency is increased in a direction towards the first stage input shaft 5 and/or capacity of transmitting torque is increased in a direction towards the second stage output shaft 20.

Let us take as first elements, elements which, on a torque transmission path TTP1 through the gearwheel transmission 1 from the first stage input shaft 5 towards the second stage output shaft 20 are positioned closer to the first stage input shaft 5 than the second elements.

First elements could for example all be elements of the first stage 2, such as the gearwheels 5, 9, 13, 16 and 18.

Second elements could for example all be elements of the second stage 3, such as the gearwheels 26, 27, 28 and 30. If, in such a case, the first elements are executed with a first module MOD_PV1 and the second elements are executed with a second module MOD_PV2, and the first module MOD_PV1 is different from the second module MOD_PV2, then the first module MOD_PV1 should typically be smaller than the second module MOD_PV2, i.e. MOD_PV1<MOD_PV2.

Indeed, normally such a difference would increase the overall efficiency in the first stage 2 compared to the overall efficiency of the second stage 3.

In other cases, according to another principle of the invention however first elements could also be part of the second stage 3 and second elements could also be part of the first stage 2.

According to this other principle of the invention, if the first elements are executed with a first module MOD_PV1 and the second elements are executed with a second module MOD_PV2, and the first module MOD_PV1 is different from the second module MOD_PV2, then the first module MOD_PV1 should be smaller than the second module MOD_PV2, i.e. MOD_PV1<MOD_PV2.

In that case, the efficiency is indeed increased in a direction towards the first stage input shaft 5 compared to the case wherein the first elements would have been executed with a higher module MOD_PV2, which is the same as the second module MOD_PV2 by which the second elements are executed.

In a similar way, certain other of the afore-mentioned execution parameters or all other afore-mentioned execution parameters or still other execution parameters can differ from one another in the entire gearwheel transmission 1.

Hereby, in general the following principles should be taken into account:

the level and distribution of a first profile shift PS_PV1 applied on first elements (which are closer on the torque transmission path TTP1 to the first stage input shaft 5 or which are simply part of the first stage 2) should be optimized for efficiency and the level and distribution of a second profile shift PS_PV2 applied on second elements (which are closer on the torque transmission path TTP1 to the second stage output shaft 20 or which are simply part of the second stage 3) should be optimized for robustness;

a first quality level QL_PV1 applied on said first elements should be higher than a second quality level QL_PV2 applied on said second elements;

a first accuracy ACC_PV1 applied on said first elements should be higher than a second accuracy ACC_PV2 applied on said second elements;

a first contact ratio CR_PV1 applied on said first elements should be smaller than a second contact ratio CR_PV2 applied on said second elements;

a contact roughness CR_PV1 applied on said first elements should be smaller than a contact roughness CR_PV2 applied on said second elements;

a first tooth geometry TG_PV1 used to configure said first elements should be optimized for efficiency and a second tooth geometry TG_PV2 used to configure said second elements should be optimized for increasing capacity for transmitting torque;

a first material MA_PV1 used for fabricating said first elements should be lighter and/or have a lower strength than a second material MA_PV2 used for fabricating said second elements; and, a first surface hardness SH_PV1 applied on said first elements should be smaller than a second surface hardness SH_PV2 applied on said second elements.

In other embodiments of a gearwheel transmission 1 in accordance with the invention more groups of elements or gearwheels which are executed differently by having their execution parameters set to different values can be applied, in order to create an overall efficiency in the first stage 2 which is higher than the efficiency in the second stage 3 and/or to create an overall capacity of transmitting torque in the second stage 3 which is higher than the capacity to transmit torque in the first stage 2.

According to another principle of the invention the above-mentioned general principles should be taken into account for each pair of consecutive groups of such elements in function of their position along the considered torque transmission path.

Some execution parameters cannot just be set independent from one another.

For example, for a certain chosen material its roughness and surface hardening cannot be set to whatever value, so that these execution parameters are—in a rather complicated way—related to one another other.

According to the invention, in low torque engagements such as is typically the case in the first stage 2 of the gearwheel transmission 1, the material should be selected to reduce contact roughness, to reduce weight and to provide good lubrication so to improve the efficiency of that stage 2.

In high torque engagements such as is typically the case in the second stage 3 of the gearwheel transmission 1, materials with high strength combined with surface hardening should be used, leading to higher contact roughness and higher capacity of transmitting torque, with however a relatively lower efficiency.

In some applications the load characteristics are not symmetrical, wherein for example in one sense of rotation higher teeth robustness (higher forces present) may be needed, whereas in the opposite sense of rotation on the contrary lower robustness is required, but higher contact velocities are present.

By using asymmetric teeth flanks, each flank of these teeth can be optimized in function of the load applied on it and in function of its rotational speed, which is dependent in these application on the sense of rotation.

This means actually that in these applications the role of the first stage 2 and the second stage 3 are interchanged, when the sense of rotation in the gearwheel transmission 1 is reversed.

In the embodiment represented in FIG. 1 each gearwheel of the gearwheel transmission 1 intermeshes with one or more intermeshing gearwheels, whereby the intermeshing gearwheels of the concerned gearwheel all operate at the same or essentially the same rotational speed.

For example, the first stage outlet sun wheel 18 intermeshes with the group 32 of first stage output planetary gearwheels 9 and with no other gearwheels of the gearwheel transmission 1.

The first stage output planetary gearwheels 9 are all supported on the same intermediate planet carrier 21 and as a consequence their rotational speed is essentially the same.

This is the case with all the gearwheels of the gearwheel transmission 1 and it allows for a design wherein the execution parameters are set such that each pair of intermeshing gearwheels is optimized in function of its operational conditions of torque and rotational speed.

It is clear that in this way a very good performance of a gearwheel transmission 1 in accordance with the invention can be obtained.

Figure 2:
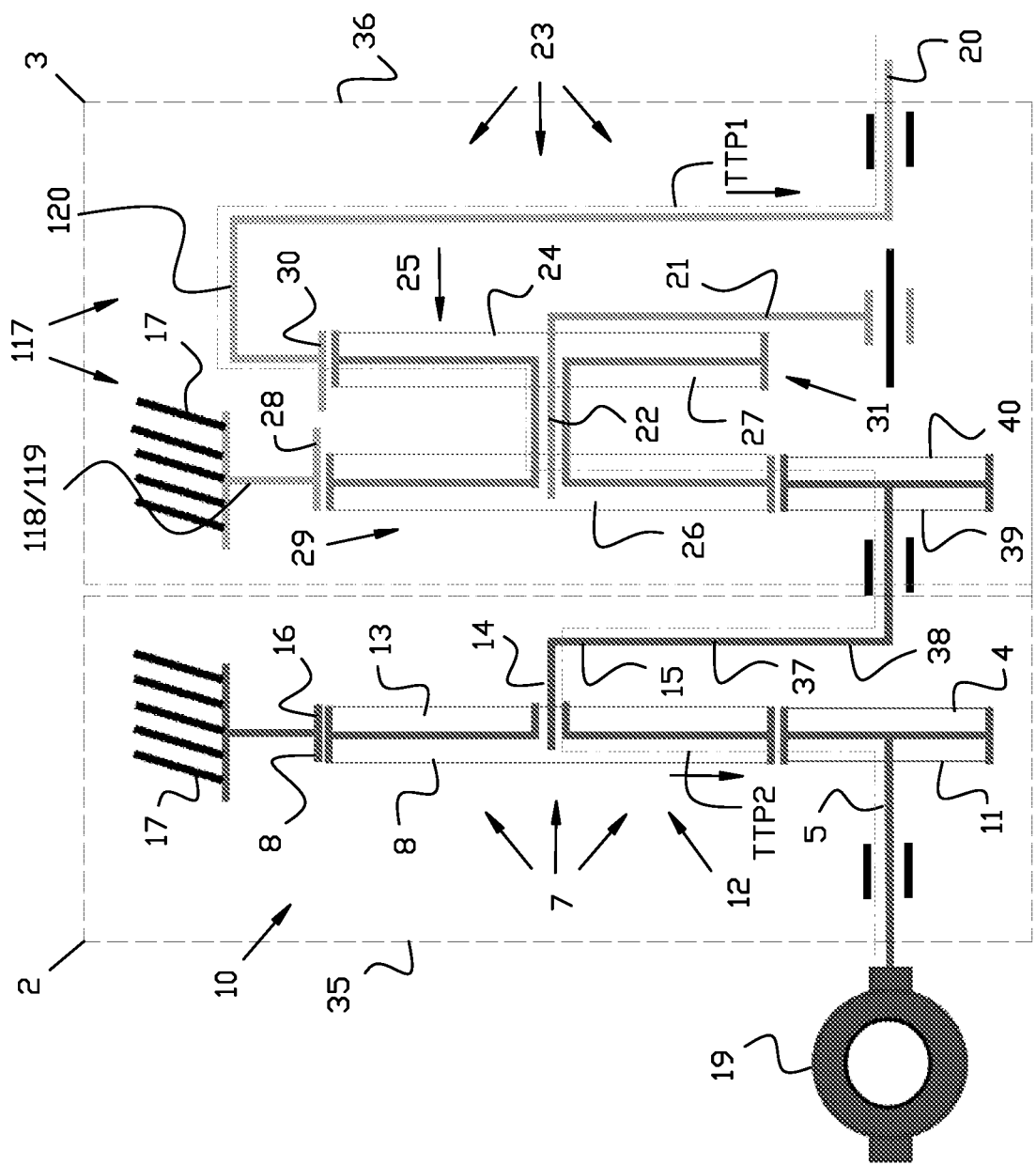

In FIG. 2 another embodiment of a gearwheel transmission 1 in accordance with the invention is represented, which is different compared to the former embodiment in that the first stage 1 does not comprise first stage output planetary gearwheels 9 and in that the second stage compound planetary type gearwheel assembly 23 is structured differently.

This time, the second stage compound planetary type gearwheel assembly 23 comprises second stage compound planetary gearwheel 24 which are each exclusively composed of second stage planetary gearwheels, in particular the second stage planetary gearwheels 26 and 27.

Furthermore, the first stage output element is in the example of FIG. 1 a single first stage output element 37, which is formed by a first stage output planet carrier 38 and which is interconnected with a second stage input element, which is a single second stage input element 39.

The single second stage input element 39 is a second stage input sun wheel 40 of the second stage compound planetary type gearwheel assembly 23.

This second stage input sun wheel 40 is intermeshing with each planetary gearwheel of the group 29 of circumferentially spaced apart second stage planetary gearwheels 26 composed by a planetary gearwheel 26 of each second stage compound planetary gearwheel 24.

This type of interconnection between the first stage 2 and the second stage 3 is in line with the first interconnection configuration mentioned above as well as in claim 1.

Since in the embodiment of FIG. 2 there is no third group 32 of first stage output planetary gearwheels 9 anymore, as was the case in the embodiment of FIG. 1, a more compact configuration is obtained.

On the other hand, as can be clearly seen in FIG. 2, the group 29 of second stage planetary gearwheels 26 is in this embodiment intermeshing with the second stage input sun wheel 40 as well as with the second stage fixed ring wheel 28.

The second stage fixed ring wheel 28 is fixedly arranged in the housing 17 and is therefore not moving at all, while the second stage input sun wheel 40 is during operation of the gearwheel transmission 1 driven by the first stage 2 for a rotational movement.

This means that in the example of FIG. 2, each second stage planetary gearwheels 26 of the group 29 of second stage planetary gearwheels 26 is interacting with two gearwheels, in particular second stage fixed ring wheel 28 and the second stage input sun wheel 40, which operate at completely different operational conditions.

As a consequence, it is impossible to choose execution parameters for this group 29 of second stage planetary gearwheels 26 which are optimal for both interactions, i.e. the interaction with the second stage fixed ring wheel 28 and the interaction with the second stage input sun wheel 40.

As a result, not a same level of the overall efficiency can be obtained in an embodiment of a gearwheel transmission 1 as represented in FIG. 2 compared to the case of FIG. 1, wherein all the pairs of mutually interacting gearwheels can be separately and freely designed and their execution be optimized in function of the operational conditions.

If one looks superficially to the embodiments of FIG. 1 and FIG. 2, it could seem that the embodiment of FIG. 2 is simply obtained by eliminating the first stage output planetary gearwheels 9 and let the first stage outlet sun wheel 18 directly intermesh with the group 29 of second stage planetary gearwheels 26.

This is however not the case, since in the embodiment of FIG. 2 just as much as in the embodiment of FIG. 1, the elements of the first stage 2 and the elements of the second stage 3 are executed according to a set of execution parameters which are set to different values in both stages 2 and 3 and this in such a way that the overall capacity of transmitting torque is higher in the second stage 3 than in the first stage 2 and/or the overall efficiency is higher in first stage 2 than in the second stage 3.

According to another principle the difference in execution can also be such that the capacity of transmitting torque is increased along a torque transmission path TTP1 from the first stage input shaft 5 towards the second stage output shaft 20 and transmission efficiency is increased along a torque transmission path TTP2 from the second stage output shaft 20 towards the first stage input shaft 5.

This means that in the embodiment of FIG. 2 the sun wheel 40 is executed and optimized together with the group 29 of second stage planetary gearwheels 26 for obtaining a higher capacity for transmitting torque, for example by using a material such as a certain metal with a certain strength for these concerned elements, while the first stage entry gearwheel 4, the first stage planetary gearwheels 13 and the first stage fixed ring wheel 16 are all executed with certain execution parameters set to other values, so to optimize for efficiency, for example by executing these concerned gearwheels 4, 13 and in another material such as plastic, which has a lighter weight but is less strong.

In this embodiment of FIG. 2 the first stage 2 and the second stage 3 are again different in nature in that their respective gearwheels are differently executed, their execution parameters being set to different parameter values in each stage 2 and 3.

This is of course again a particular case wherein the fact that a certain gearwheel belongs to the first stage 2 or the second stage 3 coincides with the way it has been executed, but in general this is not a requirement according to the invention.

In the embodiment of FIG. 2 the interconnection mechanism 7 comprises the housing 17, as well as the interconnection gearwheels 8 represented by the first stage fixed ring wheel 16 and the group 12 of first stage planetary gearwheels 13.

The first stage planet carrier 15 fulfills of course the role of first stage output planet carrier 38.

By combining the characteristics of the embodiments of FIGS. 1 and 2 it is easily imagined that another embodiment of a gearwheel transmission 1 in accordance with the invention can be obtained (not represented in the figures), wherein the second stage compound planetary gearwheels 24 are again not of the hybrid type (as in FIG. 2), but contain three groups of planetary gearwheels (as in FIG. 1) which this time however are all second stage planetary gearwheels, and which are for example all executed with their execution parameters set to the same parameter values adapted and optimized for transmission of torque and which parameter values are for example different from parameter values given to corresponding execution parameters of elements of the first stage 2.

It is clear that in such an embodiment again the execution of all the elements can be optimized in function of their operational conditions, while a little bit less compact configuration is obtained.

Figure 3:
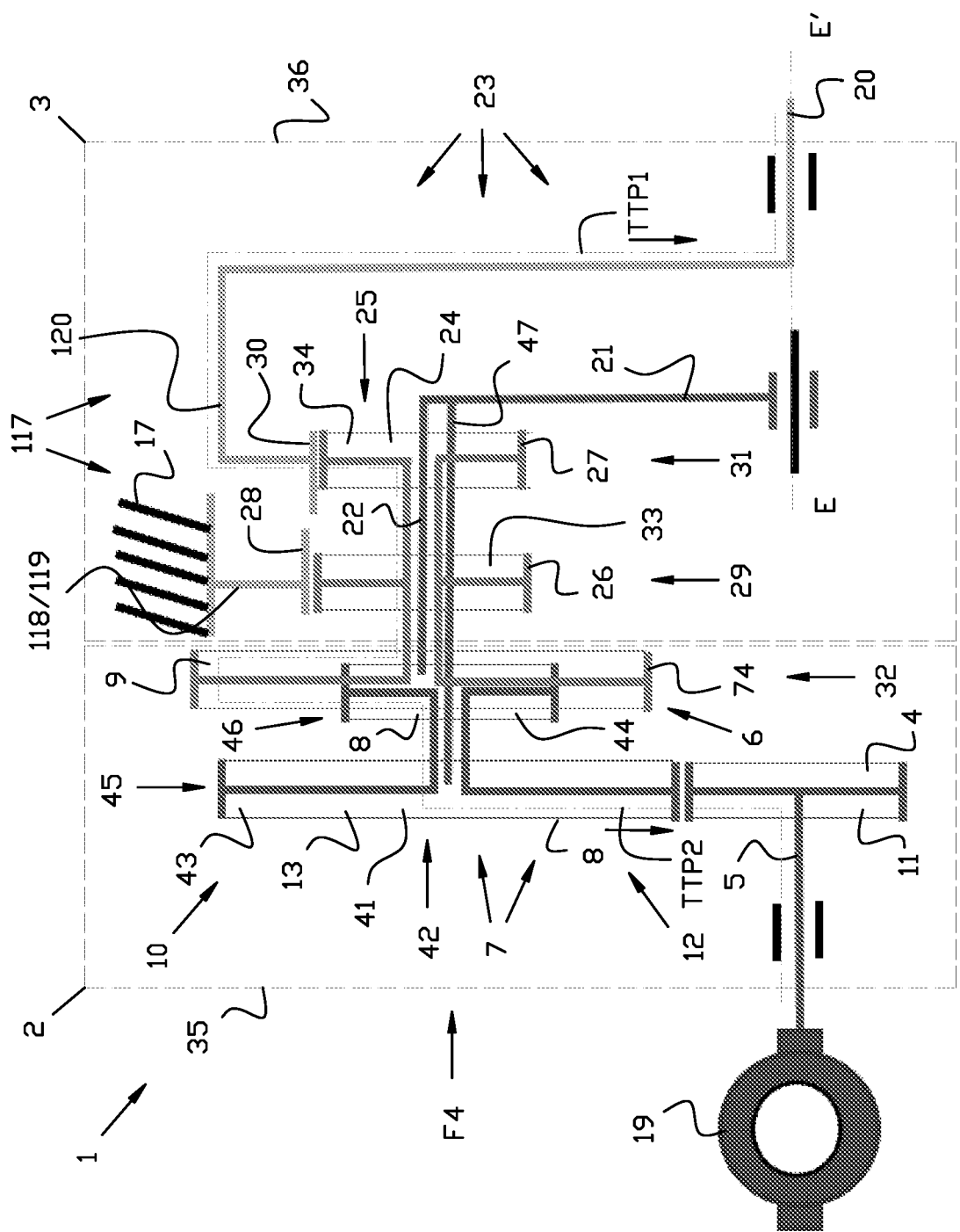
Figure 4:
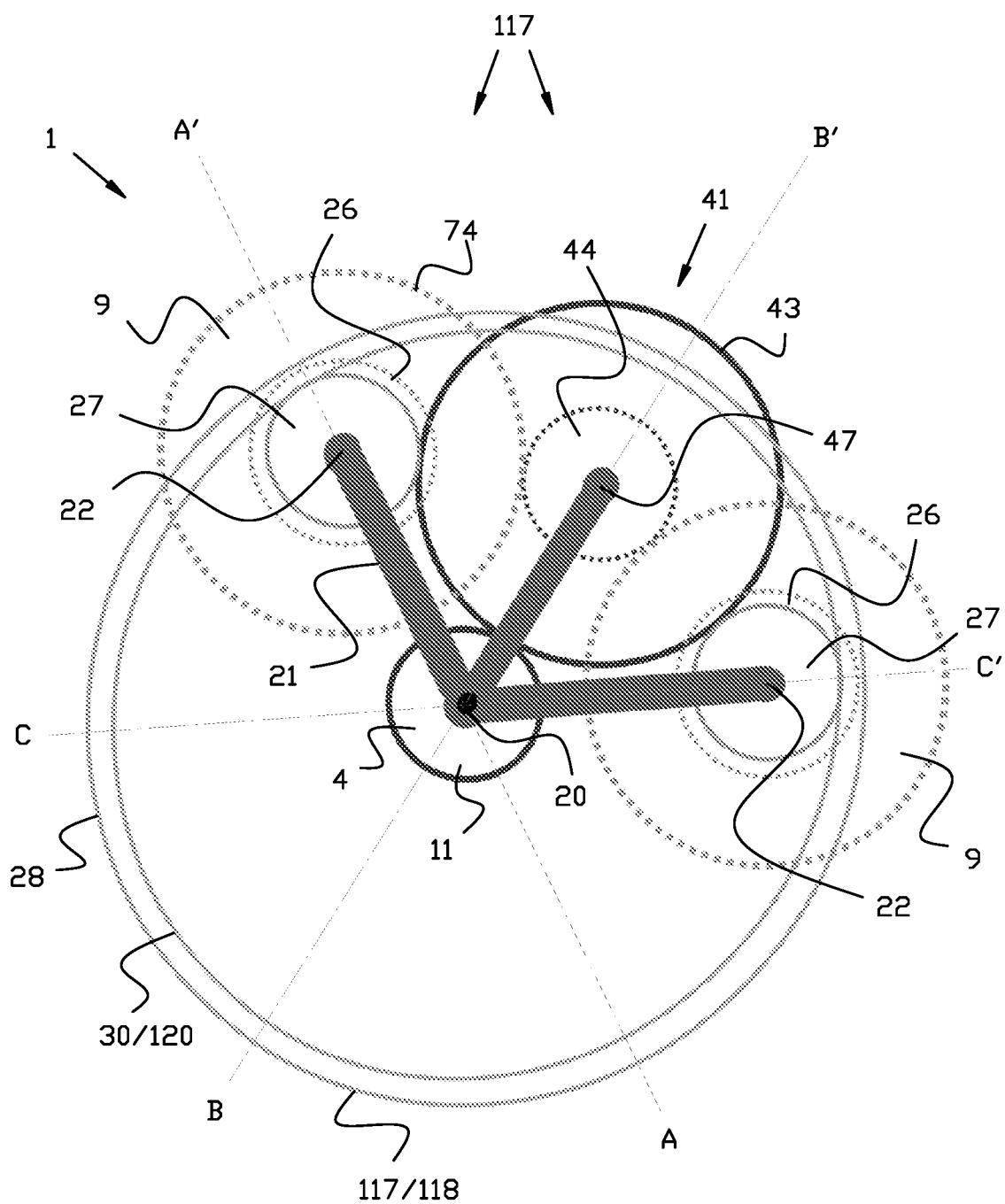
FIG. 4 is a side view in a direction indicated by arrow F4 on the embodiment of a gearwheel transmission in accordance with the invention of FIG. 3.
Figure 5:
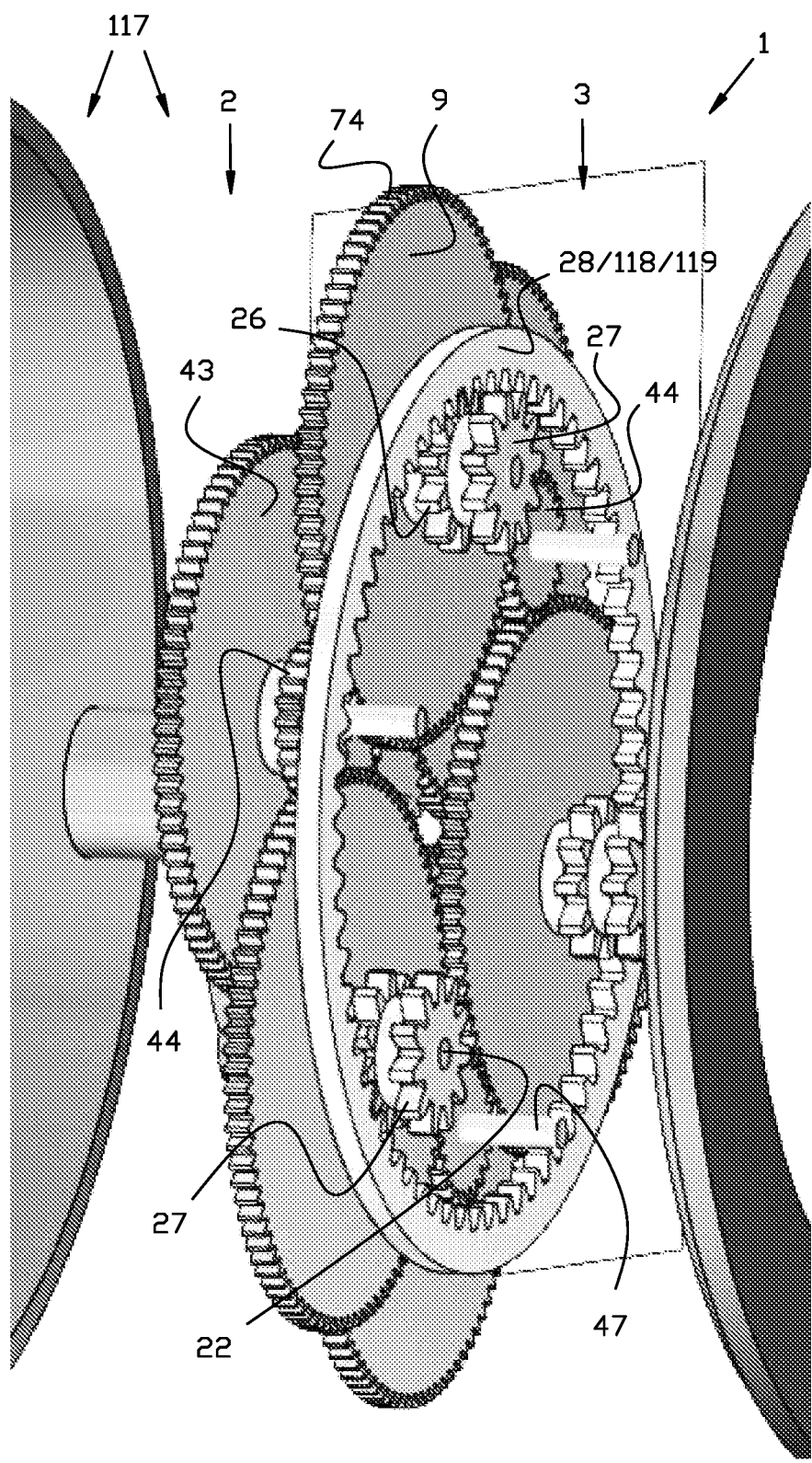
FIG. 5 is a more realistic perspective view of the same gearwheel transmission in accordance with the invention represented in FIG. 3.

FIGS. 3 to 5 illustrate still another embodiment of a gearwheel transmission in accordance with the invention which is in many ways similar to the embodiment of FIG. 1.

In the embodiment of FIGS. 3 to 5 however the first stage 2 does not comprise anymore a first stage fixed ring wheel 16, nor a first stage planet carrier 15, and instead the first stage planetary gearwheels 13 this time are each first stage compound planetary gearwheels 41 forming a pair 42 of fixedly interconnected, stepped first stage planetary gearwheels 43 and 44.

These first stage compound planetary gearwheels 41 more specifically form a first group 45 of circumferentially spaced apart first stage planetary gearwheels 43 composed by the first planetary gearwheel 43 of each afore-mentioned pair 42 of first stage planetary gearwheels 43 and 44, as well as a second group 46 of circumferentially spaced apart first stage planetary gearwheels 44 composed by the second planetary gearwheel 44 of each afore-mentioned pair 42 of first stage planetary gearwheels 43 and 44.

The first planetary gearwheels 43 and 44 are provided concentrically around the first stage input shaft 5.

Furthermore, each afore-mentioned second planetary gearwheel 44 of the circumferentially spaced apart first stage compound planetary gearwheels 41 is intermeshing with a corresponding first stage output element 6, formed by the group 32 of first stage output planetary gearwheels 9.

Another characteristic of the embodiment represented in FIGS. 3 to 5 is that the intermediate planet carrier 21 is provided with a number of circumferentially spaced apart secondary, intermediate carrier planetary gearwheel shafts mounted fixedly or in a rotatable manner on the intermediate planet carrier 21.

These secondary, intermediate carrier planetary gearwheel shafts 47 each support an afore-mentioned first stage compound planetary gearwheel 41.

Hereby, each secondary, intermediate carrier planetary gearwheel shaft 47 is extending in a bisector plane BB' of a corresponding pair of planes AA' and CC'.

Each plane AA' and CC' of the pair extends through the central axis EE' of the second stage output shaft 20 and through one of two consecutive primary, intermediate carrier planetary gearwheel shafts 22.

This is clearly illustrated in FIG. 4.

It is noticed that in the embodiment of FIGS. 3 to 5 the first stage output elements 6 are again formed by the first stage output planetary gearwheels 9, which are interconnected with the second stage planetary gearwheels 26 forming the second stage input elements 33, as was the case in the embodiment of FIG. 1.

As a consequence, the interconnection between the first stage 2 and the second stage 3 is again in line with the third interconnection configuration mentioned above and in claim 1.

Furthermore the interconnection mechanism 7 comprises this time only the first stage compound planetary gearwheels 41.

Such an embodiment of a gearwheel transmission 1 as represented in FIGS. 3 to 5 has the advantage that no first stage fixed ring wheel 16 is needed, nor a first stage planet carrier 15, which makes the gearwheel transmission 1 much lighter and more compact.

The first stage 2 and second stage 3 are also again executed by assigning different parameter values to certain execution parameters in the respective stages 2 and 3, as was already explained extensively before, but which is not a necessary requirement according to the invention.

Figure 6:
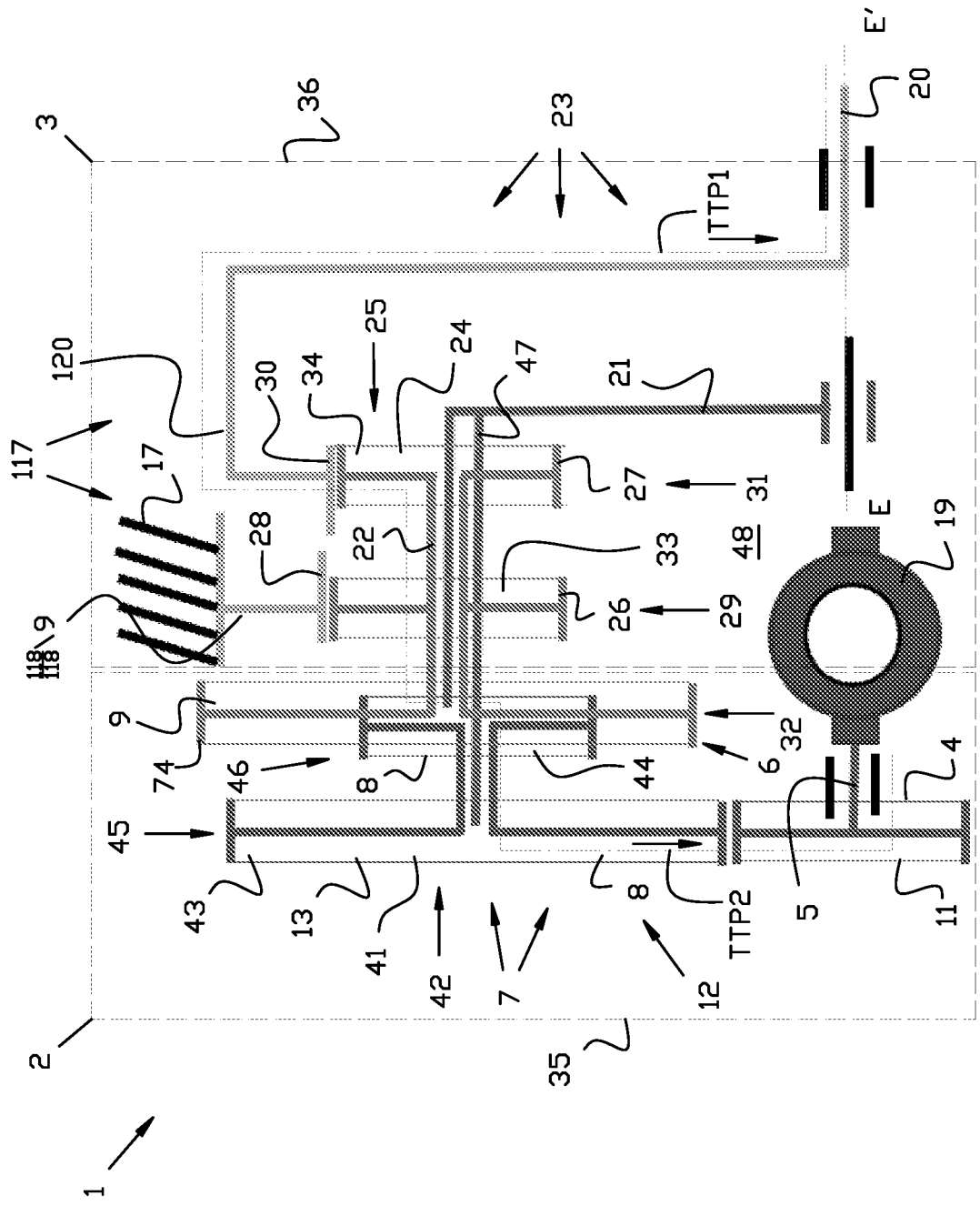

FIG. 6 illustrates a variant of the former embodiment of FIGS. 3 to 5, wherein the gearwheel transmission 1 is made still more compact.

In particular, in this embodiment of FIG. 6 the input shaft 5 is extending inwardly into a free space 48 in the second stage 3 at the centre of the intermediate planet carrier 21.

The actuator 19 is integrated in the same free space 48.

Such an embodiment as represented in FIG. 6 is extremely compact and can be easily mounted in narrow spaces, such as in joints of a prosthesis or a robotic machine.

Figure 7:
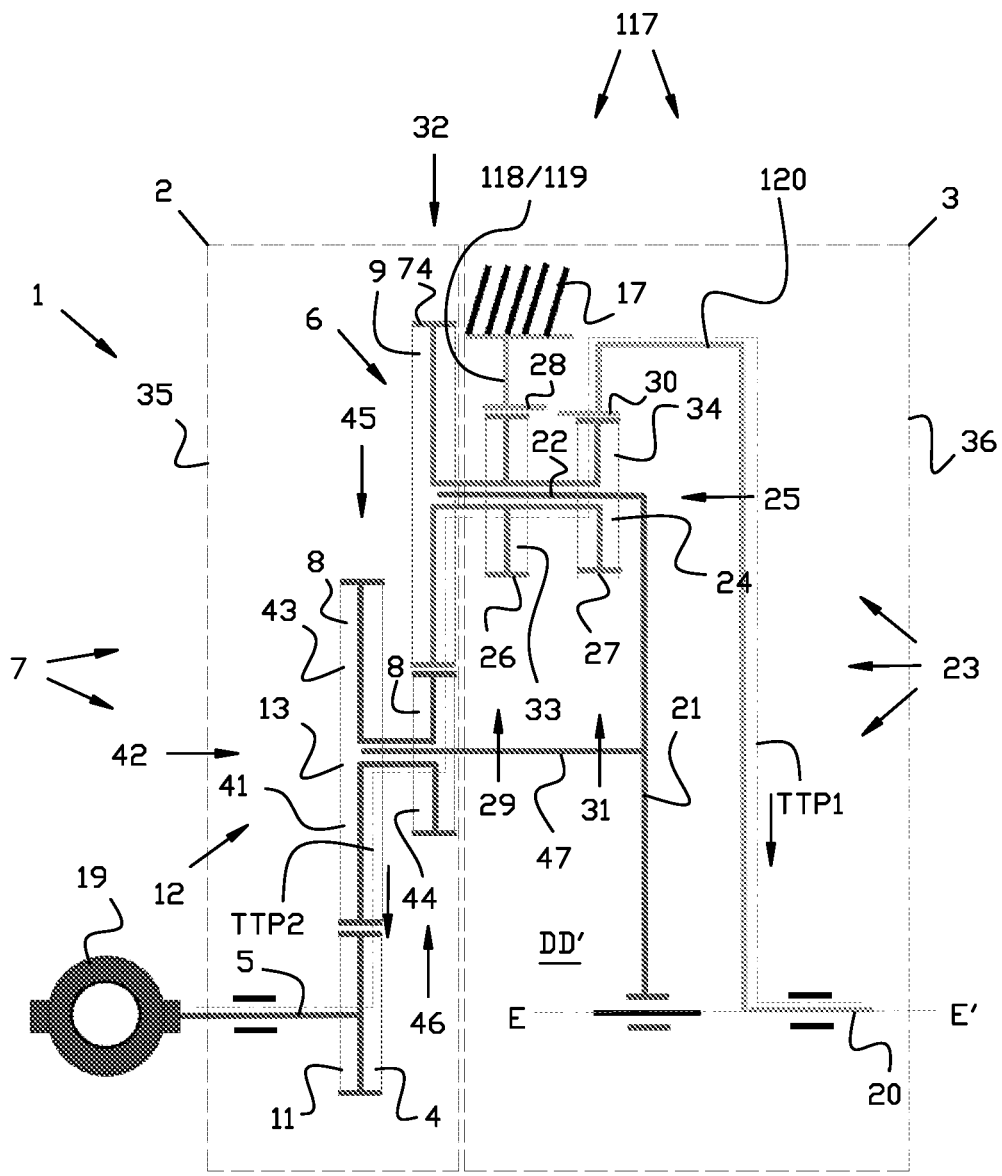

In FIG. 7 another embodiment of a gearwheel transmission 1 in accordance with the invention is represented, which comprises the same elements as the embodiment of FIGS. 3 to 5 and which has a structure which is almost identical.

The difference is however that in the embodiment of figure each primary, intermediate carrier planetary gearwheel shaft 22 and its corresponding secondary, intermediate carrier planetary gearwheel shaft 47 are provided in a single, radially extending plane DU' which comprises the central axis EE' of the second stage output shaft 20.

The gearwheels are also somewhat rearranged in that the first stage compound planetary gearwheels 41 are brought somewhat closer to the centre, more near to the central axis EE' of the second stage output shaft 20.

Figure 8:
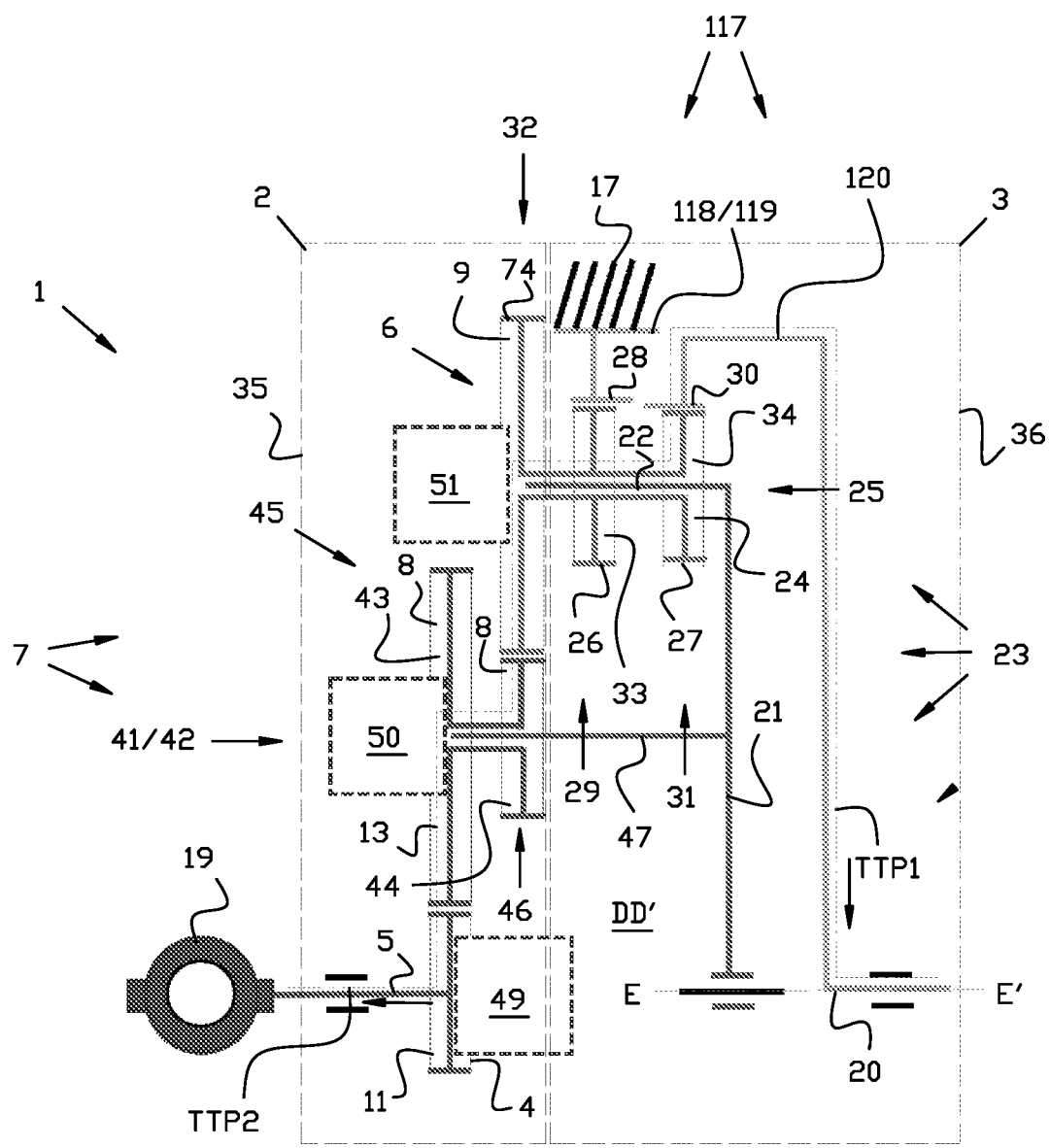
Figure 9:
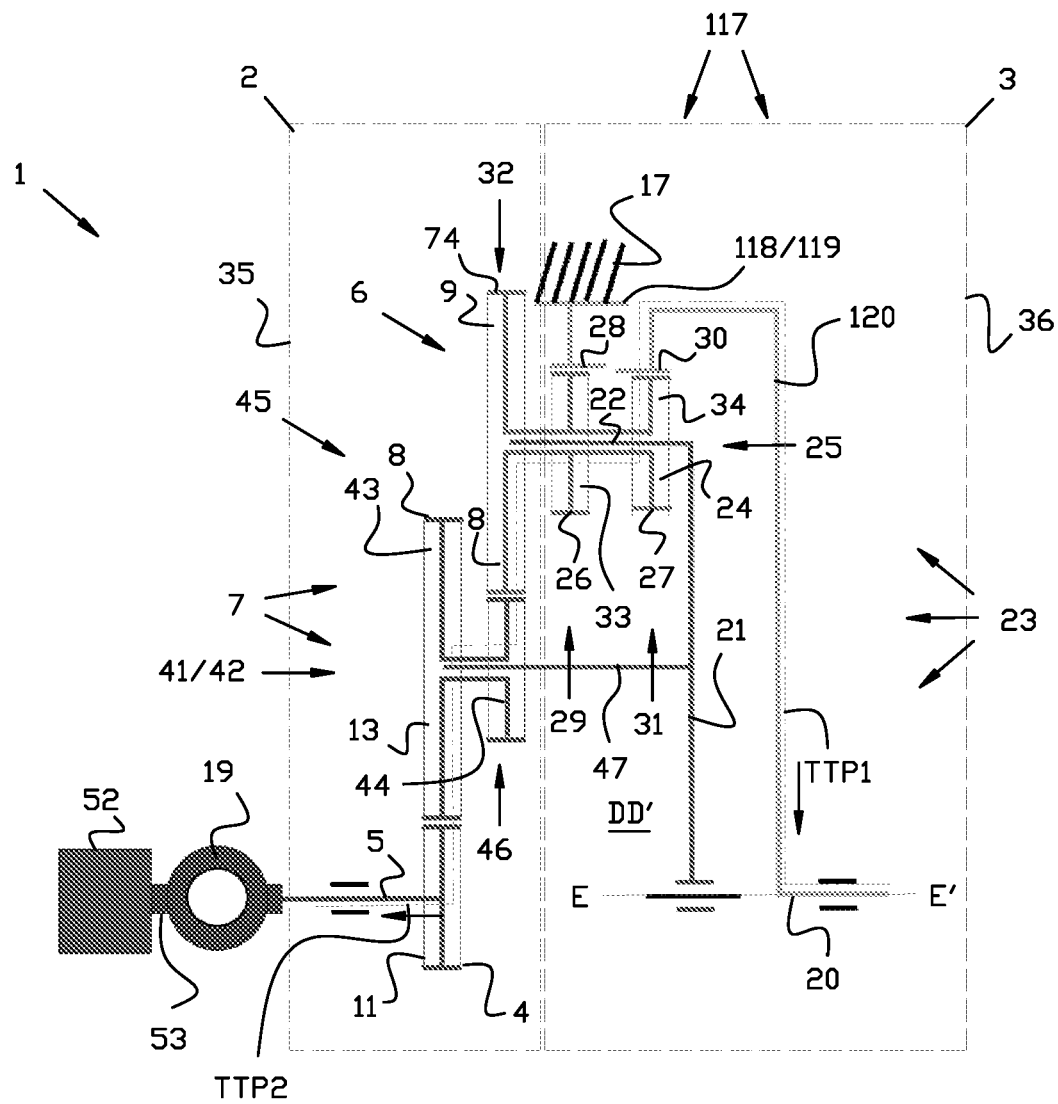

FIG. 8 illustrates an embodiment of a gearwheel transmission 1 which is almost identical to the embodiment of FIG. 7, but wherein this time clutches 49, 50 and 51 are included in the configuration.

These clutches 49, 50 and 51 are mounted between a pair of elements of the gearwheel transmission 1 and allow transmission of torque between the concerned elements in one sense and prevent transmission of torque between the concerned elements in the opposite sense.

In the embodiment of FIG. 8 it is illustrated in dashed line that for example a clutch 49 can be mounted between the first stage input shaft 5 and the first stage entry gearwheel 4 or first stage entry sun wheel 11.

Furthermore, it can be useful to mount such a clutch between any of the planetary gearwheel shafts 22, 47 and a planetary gearwheel which is mounted on that planetary gearwheel shaft 22 or 47.

In FIG. 8 there is another dashed line representing a group of clutches 50 which are mounted between each secondary, intermediate carrier planetary gearwheel shaft 47 and the corresponding first stage compound planetary gearwheel 41.

Similarly, it is illustrated in dashed line that a group of clutches 51 can be mounted between each primary, intermediate carrier planetary gearwheel shaft 22 and the corresponding hybrid, compound planetary gearwheel 34.

In a possible embodiment the clutches 49, 50 and 51 can be of a type in which controllable locking-unlocking means are provided for unlocking a situation wherein transmission of torque is prevented in said opposite sense.

Such kind of clutches 49, 50 and 51 help to control the movements in the gearwheel transmission 1 and as a consequence also of movements between the first stage input shaft 5 and the second stage output shaft 20.

By activating or not activating afore-mentioned locking-unlocking means the overall gearwheel transmission ratio R can be changed and energy stored in elements connected to the gearwheel transmission 1, such as springs, can be stored and released, which is a characteristic that is very interesting for use in prostheses and orthoses for example.

The embodiment of a gearwheel transmission 1 in accordance with the invention represented in FIG. 9 is again almost identical with the embodiment of FIG. 7.

In this case, the rotational driving movement of the actuator 19 is controlled by a brake 52 which is additionally provided at the actuator shaft 53.

In more general terms, a gearwheel transmission 1 in accordance with the invention can comprise one or more of such brakes 52, which is or are provided between an element or elements of the gearwheel transmission 1 and the housing for controlling the rotational speed of parts of the gearwheel, transmission 1, such as the rotational speed of the first stage input shaft 5, the second stare output shaft 20, planetary gearwheels, gearwheels in general, planet carriers 21 and 15 or rotatable ring wheels 30.

Figure 10:
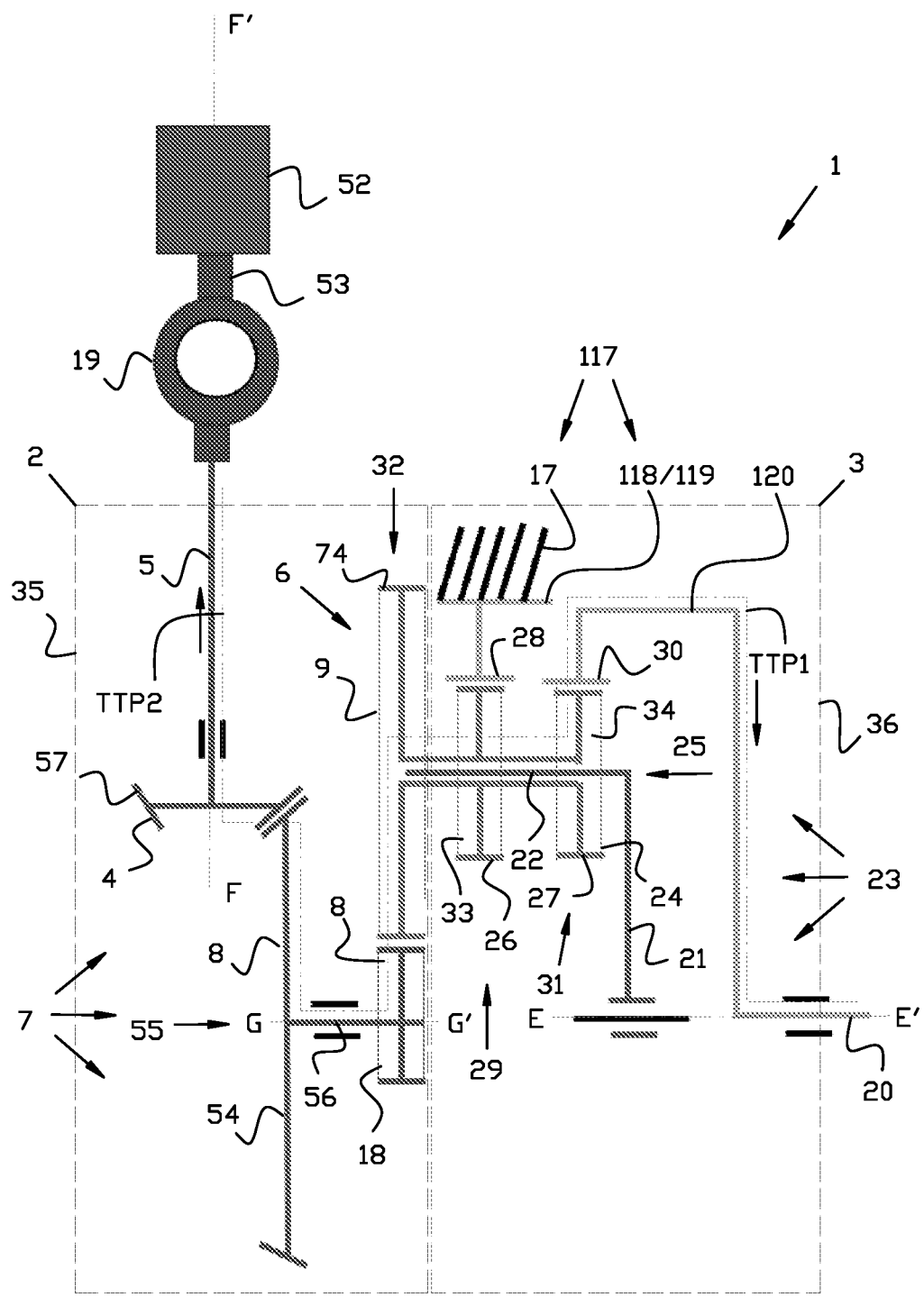

In FIG. 10 an embodiment of gearwheel transmission 1 in accordance with the invention is represented, which has a second stage 3 as well as a part of the first stage 1 that are identical with the corresponding stage 3 and part of stage 1 of the embodiment represented in FIG. 1.

In particular, in this embodiment of FIG. 10 the first stage output elements 6 are again first stare output planetary gearwheels 9, which each intermesh with a first stage outlet sun wheel 18.

However, this first stage outlet sun wheel 18 is in this case not interconnected with a first stage planet carrier 15, since the first stage 2 is not provided with a first stage planetary type gearwheel assembly 10 at all.

Instead, FIG. 10 illustrates an embodiment wherein the first stage input shaft 5 is aligned in a direction FF' which is perpendicular to the direction EE' of the second stage output shaft 20.

In order to transmit the rotational speed and torque at the first stage input shaft 5 towards the first stage output elements 6, the first stage 2 comprises in this embodiment an interconnection mechanism 7 comprising an interconnection gearwheel 8 which is a first stage bevel gearwheel 54.

More in particular, the first stage 2 is equipped with a first stage compound interconnection gearwheel 55, which is composed of, on the one hand, the afore-mentioned first stage bevel gearwheel 54 and, on the other hand, of the first stage outlet sun wheel 18.

This first stage compound interconnection gearwheel 55 is mounted in a rotatable manner on a shaft 56 which extends in a direction GG' which is aligned with the central axis EE' of the second stage output shaft 20.

The first stage bevel gearwheel 54 of this first stage compound interconnection gearwheel 55 is intermeshing with the first stage entry gearwheel 4, which is for that purpose also executed as a first stage entry bevel gearwheel 57.

The functioning of this embodiment of a gearwheel transmission 1 represented in FIG. 10 requires no further comment and is completely similar as in the former cases.

It is obvious that in all the embodiments represented in FIGS. 7 to 10 the first stage 2 and the second stage 3 are again interconnected in accordance with the third interconnection configuration described above and in claim 1.

Figure 11:
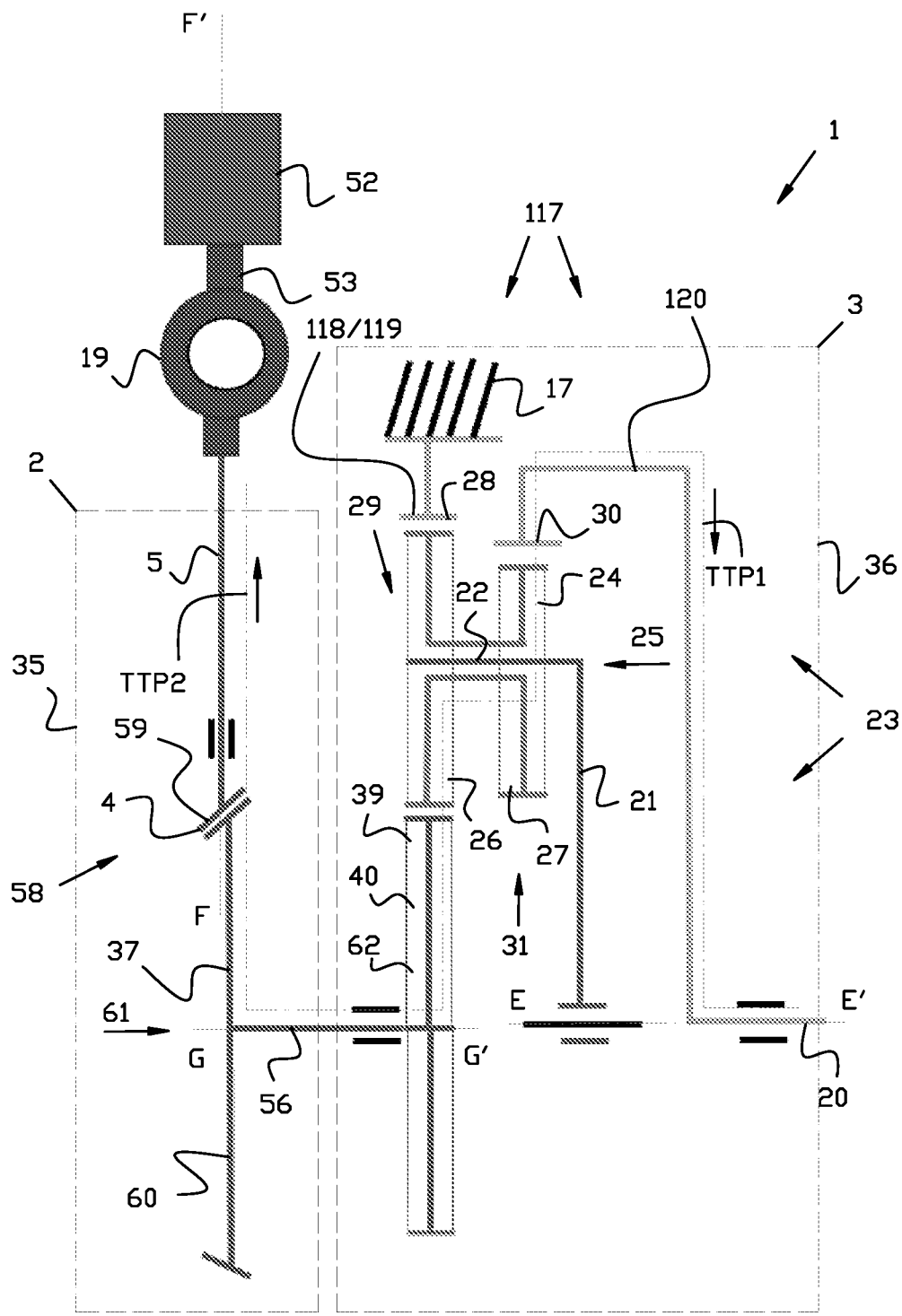

FIG. 11 illustrates an embodiment which is in many ways similar to the case of FIG. 10, but which is in many ways also different.

For example, in FIG. 11 a first stage hypoid gearing 58 is used in order to transmit torque over a right angle, instead of the pair of bevel gearwheels 54 and 57.

A hypoid gearing is a type of spiral bevel gearing whose axes do not intersect.

The first stage entry gearwheel 4 is executed as a first stage hypoid gearing pinion 59, while the first stage bevel gearwheel 54 is now replaced by a first stage hypoid gearing crown wheel 60.

Another difference with the embodiment represented in FIG. 10 is that the first stage hypoid gearing crown wheel 60 is fulfilling the role of a single first stage output element 37, as was the case with the first stage planet carrier 38 represented in the embodiment of FIG. 2.

The embodiment of FIG. 11 is therefore a case wherein there is no interconnection mechanism for indirectly interconnecting the first stage entry gearwheel 4 to a first stage output element 37, but instead this first stage entry gearwheel 4 is interacting in a direct manner with the single first stage output element 37, which is in this case represented by the first stage hypoid gearing crown wheel 60.

The first stage hypoid gearing crown wheel 60 is still a part of a compound gearwheel 61, but the other gearwheel 62 of this compound gearwheel 61 is now forming a part of the second stage 3.

The compound gearwheel 61 is in this case a hybrid, compound gearwheel 61, wherein the first stage hypoid gearing crown wheel 60 and the other gearwheel 62 are executed differently.

As explained before with respect to other embodiments, the reason why a gearwheel can be considered part of the first stage 2 rather than part of the second stage 3 and vice versa can be related to the used execution parameters, which are different in nature in the first stage 2 compared to the second stage 3, but this is not necessarily the case.

Another reason is just by definition.

In the introduction it was also explained that from another perspective a stage of the gearwheel transmission 1 can be considered as a part of the gearwheel transmission 1, which can be axially positioned near to a consecutive stage, whereby torque and speed is transmitted from one stage to another through interconnection of components of each stage which are axially spaced from one another.

Such a definition is clearly applicable to all the embodiments already described.

The other second stage gearwheel 62 of the hybrid, compound gearwheel 61 is again, as was also the case in the embodiment of FIG. 2, fulfilling the role of a single second stage input element 39 and more in particular of a single second stage input sun wheel 40.

This single second stage input sun wheel 40 formed by the other second stage gearwheel 62 is directly intermeshing with each second stage planetary gearwheel 26 of the second stage compound planetary gearwheels 24.

As a consequence, the interconnection between the first stage 2 and the second stage 3 is realized in accordance with the first interconnection configuration mentioned above and in claim 1.

Obviously, in other embodiments of a planetary gearwheel 1 in accordance with the invention other interconnection mechanisms 7 or whatever other mechanisms can be applied that enable the transmission of rotational speed and torque over an angle, such as an interconnection mechanism comprising a torsional cable.

The concerned angle can be an angle of 90°, but also any other angle.

The embodiment of FIG. 11 can also be described in still another way, when a larger definition is accepted for what a stage of the gearwheel transmission 1 can be.

In the embodiment of FIG. 11 the compound gearwheel 61 can be looked at, from still another perspective, as being entirely a part of the first stage 2, in which case the gearwheel 62 of it forms a single first stage output element 37 which is a sun wheel interacting with a croup 29 of second stage planetary gearwheels 26 which form the second stage input elements 33.

In that case the first stage 2 is partially surrounded in a radial direction by the second stage 3.

It is clear that other afore-mentioned embodiments can also be described in a similar, alternative way, when a somewhat larger definition of a stage of a gearwheel transmission is used.

The FIGS. 12 to 14 illustrate still another embodiment of a gearwheel transmission 1 in accordance with the invention which has similarities with the embodiment represented in the FIGS. 3 to 5, but is still more elaborated.

In particular, the first stage 2 and the second stage 3 are again interconnected according to the third proposed interconnection configuration mentioned above and in claim 1.

In this embodiment represented in the FIGS. 11 to 14 the first stage 2 comprises a primary step 63 and a secondary step 64.

As in the embodiment of FIGS. 3 to 5, the primary step 63 comprises first stage primary compound planetary gearwheels 41, forming a first group 45 and a second group 46 of circumferentially spaced apart primary step planetary gearwheels 65 and 66, respectively represented by first stage planetary gearwheels 43 and 44.

The secondary step 64 comprises first stare secondary compound planetary gearwheels 67 forming a first group 68 and a second group 69 of circumferentially spaced apart secondary step planetary gearwheels 70 and 71.

The first group 45 of primary step planetary gearwheels 65 are intermeshing with the first stage entry sun wheel 11 and the second group 46 of primary step planetary gearwheels 66 are each intermeshing with a corresponding secondary step planetary gearwheel 70 of the first group 68 of secondary step planetary gearwheels 70.

Finally, the second group 69 of secondary step planetary gearwheels 71 each intermesh with a corresponding first stage output element 6, still represented by first stage output planetary gearwheels 9.

The first stage primary compound planetary gearwheels 41 are still each supported by a secondary, intermediate carrier planetary gearwheel shaft 47, as was also the case in the embodiment of FIGS. 3 to 5.

In order to support each of the first stage secondary compound planetary gearwheels 67 the intermediate planet carrier 21 is provided with a number of circumferentially spaced apart tertiary, intermediate carrier planetary gearwheel shafts 72 mounted fixedly or in a rotatable manner on the intermediate planet carrier 21.

Furthermore, as can be deducted from FIG. 13, each tertiary, intermediate carrier planetary gearwheel shaft 72 is extending in a bisector plane HH' of a corresponding pair of planes II' and JJ', in particular a first plane II' and a second plane JJ', wherein the first plane II' and the second plane JJ' each extend through the central axis EE' of the second stage output shaft 20 and the first plane II' additionally extends through a primary, intermediate carrier planetary gearwheel shaft 22, while the second plane JJ' additionally extends through a nearby secondary, intermediate carrier planetary gearwheel shaft 47.

Each secondary, intermediate carrier planetary gearwheel shaft 47 is still extending in a bisector plane between two consecutive primary, intermediate carrier planetary gearwheel shafts 22, as was also the case in the embodiment of FIGS. 3 to 5.

Such an embodiment of a gearwheel transmission 1 in accordance with the invention is very suitable for being applied in prostheses or orthoses or in robotic applications.

In a typical example of a robotic application the following conditions apply:
the maximum torque at the first stage input shaft 5 is about 0.15 Nm;
the maximum torque at the second stage output shaft 20 is about 50 Nm;
the maximum rotational speed at the first stage input shaft 5 is about 15.000 rpm;
the maximum rotational speed at the second stage 20 output shaft is about 40 rpm;
the gear of the gearwheel transmission R (defined by the rotational speed at the second stage output shaft divided by the rotational speed at the first stage input shaft) is about 1:400.

The conditions at intermediate steps of the gearwheel transmission 1 are typically as follows:
the maximum torque after the primary step 63 of the first stage 2 is about 0.5 Nm;
the maximum rotational speed after the primary step 63 of the first stage 2 is about 4.000 rpm;
the maximum torque after the secondary step 64 of the first stage 2 is about 2 Nm;
the maximum rotational speed after the secondary step 64 of the first stage 2 is about 1.000 rpm;

The first stage entry gearwheel 4 as well as the first stage primary step planetary gearwheels 65 and 66 are typically made of plastic.

The first stage secondary step planetary gearwheels 70 and 71 are typically made of a plastic such as Nylon, Polyethylene, Poly-Ether-Ether-Ketone or the like, or of a lightweight metal, such as brass or aluminum or the like.

The second stage fixed ring wheel 28, the second stage rotatable ring wheel 30 as well as the second stage planetary gearwheels 26 and 27 and the first stage output planetary gearwheels 9 are typically made of gear steel, like heat-treatment, case-hardened or nitride steels.

It is clear that in this embodiment of the FIGS. 12 to 14 the way gearwheels are executed is not coinciding with the fact that they are part of the first sage 2 or the second stage 3, as was the case in many of the preceding embodiments.

Furthermore, it is easily understood that by executing the different steps 63 and 64 of the first stage 2 and the elements of the second stage 3 with increasingly stronger and heavier materials, the capacity for transmitting torque is increasing along a torque transmission path TTP1 in the direction of the second stage output shaft 20.

In the other sense, along a torque transmission path TTP2 staring from the second stage output shaft 2 towards the first stage input shaft 5, the materials become increasingly lighter, resulting in a lower energy losses and an increasing transmission efficiency.

It is not excluded from the invention to apply completely other executions parameters for fabricating a gearwheel transmission 1 in accordance with the invention, taking into account more or less execution parameters and or differentiating more or less the execution of the different components along the torque transmissions paths in order to obtain an overall high efficiency in the first stage 2 and/or an overall, high capacity or transmitting torque in the second stage 3, or to realize certain trends and an overall performance of the gearwheel transmission 1.

In FIG. 15 still another embodiment of a gearwheel transmission in accordance with the invention is represented which can be considered as a kind of generic embodiment.

The first stage 2 and the second stage 3 are again interconnected according to the third proposed interconnection configuration mentioned above and in claim 1.

In this embodiment the first stage 2 is reduced to a minimum of components.

Indeed the first stage entry gearwheel 4, which is still a first stage entry sun wheel 11 is directly intermeshing with the first stage output elements 6, which are formed by first stage output planetary gearwheels 9.

The second stage 3 is executed identical as in the embodiment of FIG. 1 with a second stage compound planetary type gearwheel assembly 23 which comprises hybrid, compound planetary gearwheels 34, each composed of a pair of second stage planetary gearwheels 26 and 27 interconnected with a first stage planetary gearwheel 9.

In the represented embodiment the first stage entry sun wheel 11 and the first stage output planetary gearwheels 9 are executed with execution parameters set to certain identical parameter values PV1, which is indicated in FIG. 15 by drawing these parts in white.

Furthermore, the second stage planetary gearwheels 25 and 26, as well as the second stage fixed ring wheel 28 and the second stage rotatable ring wheel 30 are executed with corresponding parameter values set to certain identical parameter values PV2.

The parameter values PV2 differ however from the parameter values PV1, which is indicated in FIG. 15 by drawing the corresponding parts in grey.

The difference is such that the overall transmission efficiency in the first stage 2 is higher than in the second stage 3 and/or the overall capacity of transmitting torque is higher in the second stage 3 than in the first stage 2.

According to another principle of the invention the difference can also be such that when a torque transmission path TTP1 is followed towards the second stage output shaft 20, there is an increase in capacity for transforming torque, and when a torque transmission path TTP2 is followed in the opposite direction towards the first stage input shaft 5 there is an increase in transmission efficiency.

In other embodiments however, the execution of components of the gearwheel transmission 1 can be still more fine-tuned, in accordance with the principles elaborated before.

A gearwheel transmission 1 in accordance with the invention is preferably back-drivable, i.e. torque exerted at the first stage input shaft 5 is transmitted to the second stage output shaft 20 and vice versa.

FIG. 16 illustrates schematically still another embodiment of a gearwheel transmission 1 according to the invention which is very similar to the embodiment represented in the FIGS. 3 to 5.

The first stage 2 and the second stage 3 are again interconnected according to the third proposed interconnection configuration mentioned above and in claim 1.

The difference is that in the embodiment of FIG. 16 the first stage output planetary gearwheels 9, which are supported on the primary, intermediate carrier planetary gearwheel shafts 22, are this time first stage output planetary gearwheels 9 with internal teeth 73, whereas in the former cases the first stage output planetary gearwheels 9 had external teeth 74.

The first stage planetary gearwheels 44 of the first stage compound planetary gearwheels 41, which are supported on the secondary, intermediate carrier planetary gearwheel shafts 47, are still intermeshing with these first stage output planetary gearwheels 9, but in the embodiment of FIG. 16 the intermeshing is internally, while in the embodiment of FIGS. 3 to 5 the intermeshing is externally.

Such an internal meshing of the concerned planetary gearwheels 44 and 9 has the advantage that in the same available space the first stage output planetary gearwheels can be executed with a much larger diameter, so that greater transmission ratios can be realized.

FIGS. 17 to 20 illustrate still another embodiment of a gearwheel transmission 1 in accordance with the invention, which has many similarities with the embodiment represented in FIGS. 12 to 14.

The first stage 2 and the second stage are again interconnected according to the third proposed interconnection configuration mentioned above and in claim 1.

Another similarity is for example that the intermediate planet carrier 21 of the gearwheel transmission of FIGS. 17 to 20 is again equipped with primary, intermediate carrier planetary gearwheel shafts 22, secondary, intermediate carrier planetary gearwheel shafts 47 and tertiary, intermediate carrier planetary gearwheel shafts 72.

Still another similarity is that each primary, intermediate carrier planetary gearwheel shafts 22 still supports a hybrid, compound planetary gearwheel 34, each composed of a pair of second stage planetary gearwheels 26 and 27 interconnected with a first stage planetary gearwheel 9.

On the one hand, the second stage 3 of the gearwheel transmission 1 is still essentially the same as in the embodiments of FIGS. 1, 3, 6, 9 and 12 for example, in that again the second stage planetary gearwheels 26 intermesh with a second stage fixed ring wheel 28 which is fixedly mounted in the housing 17 and the second stage planetary gearwheels 27 intermesh with a second stage rotatable ring wheel 30 which is interconnected with the second stage output shaft 20.

On the other hand, in the embodiment represented in FIGS. 17 to 20 there are this time three pairs 75 of primary, intermediate carrier planetary gearwheel shafts 22 instead of three single primary, intermediate carrier planetary gearwheel shafts 22, as was the case in the preceding examples.

The first stage 2 comprises again, as was also the case in the embodiment of FIGS. 12 to 14, a primary step 63 and a secondary step 64.

The primary step 63 comprises first stage primary compound planetary gearwheels 41, forming a first group 45 and a second group 46 of circumferentially spaced apart primary step planetary gearwheels 65 and 66.

These first stage primary compound planetary gearwheels 41 are again supported on the secondary, intermediate carrier planetary gearwheel shafts 47.

In this embodiment of FIGS. 17 to 20 there are also again three of these secondary, intermediate carrier planetary gearwheel shafts 47 disposed symmetrically around the first stage input shaft 5.

The secondary step 64 comprises first stage secondary compound planetary gearwheels 67 forming a first group 68 and a second group 69 of circumferentially spaced apart secondary step planetary gearwheels 70 and 71, which are supported on the tertiary, intermediate carrier planetary gearwheel shafts 72.

The first group 45 of primary step planetary gearwheels 65 are intermeshing with the first stage entry sun wheel 11 and the second group 46 of primary step planetary gearwheels 66 are each intermeshing with a corresponding secondary step planetary gearwheel 70 of the first group 68 of secondary step planetary gearwheels 70.

These secondary step planetary gearwheels 70 however are in the embodiment of FIGS. 17 to 20 provided with internal teeth 76 instead of with external teeth 77 as was the case in the preceding embodiment of FIGS. 12 to 14 for example, so that the meshing between the primary step planetary gearwheels 66 and the corresponding secondary step planetary gearwheels 70 is in this case an internal meshing, instead of an external meshing as was the case in the afore-mentioned embodiment.

The second group 69 of secondary step planetary gearwheels 71 each intermesh with first stage output elements 6, still represented by first stage output planetary gearwheels 9. Hereby, in the embodiment represented in FIGS. 17 to 20, each secondary step planetary gearwheel 71 intermeshes by means of its external teeth with a pair of first stage output planetary gearwheels 9, each forming a part of a hybrid, compound planetary gearwheel 34 supported on a corresponding pair 75 of primary, intermediate carrier planetary gearwheel shafts 22.

The advantage of using such pairs of hybrid, compound planetary gearwheels 34 and of doubling the planetary gear construction on the intermediate planet carrier 21, mainly in the second stage 3, is that a more robust configuration is obtained having a still higher capacity for transmitting torque in the second stage 3 of the gearwheel transmission 1.

This clearly requires a rearrangement of the disposition of certain elements in the gearwheel transmission 1, which is illustrated in more detail in FIG. 19.

First of all, the secondary, intermediate carrier planetary gearwheel shafts 47 are disposed around the first stage input shaft 5 in a symmetrical manner at an equal distance X from this shaft 5.

The secondary, intermediate carrier planetary gearwheel shafts 47 each define together with the central axis of the first stage input shaft 5 a plane KK', LL', MM'.

Since there are three secondary, intermediate carrier planetary gearwheel shafts 47, each such plane KK', LL' and MM' is rotated over 120° with respect to another of the planes KK', LL' and MM'.

Each plane KK', LL' and MM' also contains a first primary, intermediate carrier planetary gearwheel shaft 78 of each pair 75 of primary, intermediate carrier planetary gearwheel shafts 22, in particular at a side of the plane which is with respect to the first stage input shaft 5 opposite to the side which contains the corresponding secondary, intermediate carrier planetary gearwheel shaft 47 of that plane KK', LL', of MM'.

The primary, intermediate carrier planetary gearwheel shafts 22 are disposed at an equal distance Y from the first stage input shaft 5 which is substantially bigger than the afore-mentioned distance X.

The situation described up to now is somewhat similar to what is explained with respect to FIG. 4, in that each secondary, intermediate carrier planetary gearwheel shaft 47 is still extending in a bisector plane between two consecutive first primary, intermediate carrier planetary gearwheel shafts 78.

Indeed, the plane KK' for example containing an intermediate carrier planetary gearwheel shaft 47 is a bisector plane between the planes LL' and MM', which each contain their respective first primary, intermediate carrier planetary gearwheel shaft 78.

However, in the embodiment represented in FIGS. 17 to 20, for each secondary, intermediate carrier planetary gearwheel shaft 47 and a nearby first primary, intermediate carrier planetary gearwheel shaft 78 a cylindrical sector 79 can be defined, indicated by hatch lines in FIG. 19, which is delimited by the corresponding planes KK', Li' or MM' containing said shafts 47 and 78 and which cylindrical sector 79 also contains the second primary, intermediate carrier planetary gearwheel shaft 80 of the corresponding pair 75 as well as the corresponding tertiary, intermediate carrier planetary gearwheel shaft 72.

The first and second, primary, intermediate carrier planetary gearwheel shafts 78 and 80 of such a cylindrical sector 79 support the hybrid, compound planetary gearwheels 34 for interaction with the first stage secondary compound planetary gearwheel 67 supported by the tertiary, intermediate carrier planetary gearwheel shaft 72 of that cylindrical sector 79.

Similarly, said first stage secondary compound planetary gearwheel 67 is interacting with the corresponding first stage compound planetary gearwheel 41 which is supported on the secondary, intermediate carrier planetary gearwheel shaft 47 of the same cylindrical sector 79.

In that way the interaction between all the elements of the embodiment represented in FIGS. 17 to 20 is defined.

The second, primary, intermediate carrier planetary gearwheel shafts 80 are all placed at a the same distance Y from the first stage input shaft 5 as was the case with the first, primary, intermediate carrier planetary gearwheel shafts 78, while the tertiary, intermediate carrier planetary gearwheel shafts 72 are all disposed at an intermediate distance Z from the first stage input shaft 5, between the afore-mentioned distances X and Y.

Each cylindrical sector 79 can also be divided in three equal subsectors 81, 82 and 83, delimited by planes extending radially outward from the central axis of the first stage input shaft 5.

In particular, the first subsector 81 is delimited by the plane KK', LL' or MM' containing the secondary, intermediate carrier planetary gearwheel shafts 47 of the corresponding cylindrical sector 79 and by an intermediate plane OO'.

The second subsector 82 is delimited by consecutive intermediate planes OO' and PP', while the third subsector 83 is delimited by that last intermediate plane PP' and by the plane KK', LL' or MM' that contains the first, primary, intermediate carrier planetary gearwheel shafts 78 of the concerned cylindrical sector 79.

The afore-mentioned intermediate plane PP' forms a symmetrical plane around which the pair 75 of primary, intermediate carrier planetary gearwheel shafts 78 and 80 are disposed with their respective hybrid, compound planetary gearwheels 34.

That same intermediate plane PP' also comprises the corresponding tertiary, intermediate carrier planetary gearwheel shaft 72 of that cylindrical sector 79.

The corresponding second, primary, intermediate carrier planetary gearwheel shaft 80 is lying in the other intermediate plane OO'.

Apart from the here-described structure of this embodiment of a gearwheel transmission 1 in accordance with the present invention, it has also features as far as the execution of certain of its components is concerned which are similar to those described with respect to the embodiment represented in the FIGS. 12 to 14.

Corresponding components of the different stages 2 and 3 and the steps 63 and 64 can be executed in a similar way resulting in the same overall features regarding increasing capacity for transmitting torque towards the second stage output shaft 20 or increased overall capacity for transmitting torque in the second stage 3 and increasing transmission efficiency in a direction towards the first stage input shaft 5 or increased overall transmission efficiency in the first stage 2.

The use of secondary step planetary gearwheels 71 with internal teeth 76 allows for a greater difference in gearwheel diameter of the intermeshing gearwheels 71 and 9, resulting in a higher transmission ratio.

According to the invention it is of course not excluded to apply internal teeth on still other gearwheels of the gearwheel transmission 1.

FIG. 21 illustrates schematically still another embodiment of a gearwheel transmission 1 in accordance with the invention, which has in some ways certain similarities with the embodiments represented in FIGS. 2 and 12, but which is in many ways also quite different.

The first stage 2 comprises two steps 63 and 64 with first stage compound planetary gearwheels 41 and 67, which interact with one another and with the first stage entry wheel 4 in a similar manner as in the embodiment of FIG. 12.

The first stage compound planetary gearwheels 41 and 67 are this time however mounted in a rotatable manner on a first stage planet carrier 15 which is for that purpose provided with primary, first stage carrier planetary gearwheel shafts 81 and secondary, first stage carrier planetary gearwheel shafts 82 respectively.

Each primary, intermediate carrier planetary gearwheel shaft and its corresponding secondary, intermediate carrier planetary gearwheel shaft 82 are provided in a single radially extending plane DD' which comprises the central axis of the first stage input shaft 5, in a similar way as explained with respect to the embodiments represented in FIGS. 7 and 8 for example.

The first stage planet carrier 15 is mounted in a rotatable manner around the central axis of the first stage input shaft 5.

The second stage 3 of the gearwheel transmission 1 represented in FIG. 21 is somewhat similar to the second stage 3 of the embodiment represented in FIG. 2, in that it comprises a second stage compound planetary type gearwheel assembly 23 which comprises second stage compound planetary gearwheels 24 composed of solely a pair of fixedly interconnected, stepped second stage planetary gearwheels 26 and 27, which interact with a second stage fixed ring wheel 28 and a second stage rotatable ring wheel 30.

The second stage planetary gearwheels 26 form second stage input elements 33.

However, the secondary step planetary gearwheels 71 are in the embodiment represented of FIG. 21 not directly interconnected with the second stage planetary gearwheels 26 which form the second stage input elements 33, but they interact with one another through intermediation of the intermediate planetary carrier 21 in a somewhat sophisticated manner.

Indeed, in the example of FIG. 21 the intermediate planet carrier 21 is executed with an intermediate planet carrier ring wheel 83 with internal teeth 84.

These internal teeth 84 of the intermediate planet carrier ring wheel 83 intermesh with the external teeth 85 of the secondary step planetary gearwheels 71 forming an internal meshing between the corresponding gearwheels 71 and 83.

In that way, rotational movement of the secondary step planetary gearwheels 71 drives the intermediate planet carrier ring wheel 83 causing a rotating movement of the intermediate planet carrier 21 around its axis, which coincides with the central axis of the first stage input shaft or with the central axis EE' of the second stage output shaft 20, which is the same in the represented embodiments.

The rotating movement of the intermediate planet carrier 21 results in rotation of the second stage planetary gearwheels 26 and 27 and through further interaction with the second fixed ring wheel 28 and the second stage rotatable ring wheel 30, the second stage output shaft 20 is driven.

Of course, as explained before, driving sides can be reversed.

In this embodiment represented in FIG. 21, the intermediate planet carrier ring wheel 83 should be considered as a first stage output element 6, which is fixedly interconnected with the intermediate planet carrier 21, since it is through this intermediate planet carrier ring wheel 83 that the interconnection with the second stage 3 is made.

So, in this embodiment the interconnection between the first stage 2 and the second stage 3 is realized in accordance with the fourth interconnection configuration described above and claimed in claim 1.

Again the first stage 2 is preferably a high speed-low torque stage 35 and the second stage 3 a low speed-high torque stage 36 and gearwheels and possible other elements of the gearwheel transmission 1 are preferably executed with certain execution parameters set to suitable parameter values in such a way that the overall efficiency is higher in the first stage 2 compared to the overall efficiency in the second stage 3 and/or the overall capacity for transmitting torque is higher in second stage 3 than in the first stage 2, or, according to another principle of the invention, the execution is such that the capacity for transmitting torque increases along a torque transmission path TTP1 towards the second stage output shaft 20 and transmission efficiency increased along a torque transmission path TTP2 in the opposite sense.

FIG. 22 finally illustrates still another embodiment of a gearwheel transmission 1 in accordance with the invention, which can be considered as a variant on the former embodiment wherein features of the embodiment represented in FIG. 1 are introduced.

The first stage 2 and the second stage 3 are again interconnected according to the third proposed interconnection configuration mentioned above and in claim 1.

Indeed, the second stage 3 in the embodiment represented in FIG. 22 is exactly the same as in the embodiment represented in FIG. 21.

This time however, at the output of the first stage 2 first stage planetary gearwheels 9 are interconnected with the second stage planetary gearwheels 26, which still fulfill the role of second stage input elements 33, so to form hybrid, compound planetary gearwheels 34.

The first stage 3 comprises in the embodiment of FIG. 22 a tertiary step 86 which comprises a tertiary step ring wheel 87 with internal teeth 88 and which is comparable to the intermediate planet carrier ring wheel 83 in the former embodiment.

This tertiary step ring wheel 87 is mounted in a rotatable manner in the housing 17 around a central axis which coincides with the central axis EE' of the first stage input shaft 5 and the second stage output shaft 20.

A first stage outlet sun wheel 18 is mounted fixedly on or is fabricated as a monolithic piece with the tertiary step ring wheel 87, so to form a first stage tertiary compound planetary gearwheel 89.

This first stage outlet sun wheel 18 is intermeshing with the first stage output planetary gearwheel 9, as was also the case in the embodiment of FIG. 1.

The embodiments of a gearwheel transmission 1 of the invention represented in the FIGS. 1 to 22 are all of the type wherein the second stage 3 forms a so-called ring differential gearing 117, wherein a second stage fixed ring wheel 28 is fixedly connected to a housing 17, forming a first component 118 of the gearwheel transmission 1 that is functioning as a torque resisting or torque controlling means 119.

In these examples the second stage 3 also always comprises a second stage rotatable ring wheel 30 which is fixedly connected to the second stage output shaft 20 and which forms in the terminology of this invention a second component 120 of the gearwheel transmission 1.

As a possible alternative, the fixed connection between the concerned ring wheel 28 and the housing 17 can be replaced by a connection wherein rotation of the ring wheel 28 can be impeded or blocked by means of a brake or wherein a controlling means is applied in order to set the torque applied on the ring wheel 28.

Such a controlling means can for example comprise a combination of an actuator and a brake, but any other device or system which is suitable for this purpose can be used.

In what follows a gear transmission 1 in accordance with the invention will be described in a more general way.

FIG. 23 is for example a very simple schematic view 90 of such a gearwheel transmission 1 of the invention with high transmission ratio R and improved efficiency W and/or increased capacity for transmitting torque U.

The gearwheel transmission 1 can be described as essentially consisting of a first stage 2 and a second stage 3, both represented by a block or rectangle 91 and 92, and which are interconnected and/or are interacting with one another, indicated by an arrow 93 in FIG. 23, for transmission of torque and rotational speed from a first stage input shaft to a second stage output shaft 20 and/or vice versa.

The rectangles or boxes 91 and 92 correspond to the dashed rectangles representing the first and second stages 2 and 3 in the preceding figures.

FIGS. 24 and 25 depict in a very general way how the first stage 2 can be composed, while FIG. 26 does the same for the second stage 3.

In particular, the first stage 2 should at least comprise a first stage entry gearwheel 4 which is mounted fixedly on the first stage input shaft 5 and which is interacting for the transmission of rotational speed and torque with a single first stage output element 37 or with multiple first stage output elements 6.

The interaction between the first stage entry gearwheel 4 with the one or more first stage output elements 6 or 37 can be in a direct manner, as is represented in FIG. 24 and indicated by an arrow 94, or indirectly through an interconnection mechanism 7 comprising one or more interconnection gearwheels 8, which case is illustrated in FIG. 25, the interactions being symbolized by arrows 95 and 96.

It is clear that this description of the first stage 2 is completely equivalent to what was already described before and in real situations this first stage 2 can be executed in completely the same way as in the examples described with respect to the FIGS. 1 to 22 and still other forms of execution of this first stage 2 are of course not excluded from the invention.

FIG. 26 depicts also in a very general way how a second stage 3 can be composed.

Examples of second stages 3 described with respect to FIGS. 1 to 22 fit within this general description, but are only regarding second stages 3 which are executed in the form of a ring differential gearing 117, while FIG. 26 describes a larger concept of a second stage 3 which includes other types of second stages 3, such as second stages 3 which are executed as a sun differential gearing 97 or a carrier differential gearing 98 or as still other differential gearings.

As represented in FIG. 26, a second stage 3 is according to the invention a differential gearing comprising a planetary gear train system 99 which is executed in a quasi duplicated form composed of an input side 100 and an output side 101.

The input side 100 comprises a first set of planetary gearing 102 and the output side 101 comprises a second set of planetary gearing 103, which are mutually quasi identical but slightly different from one another.

The first set of planetary gearing 102 and the second set of planetary gearing 103 interact respectively with first and second interacting gearing 104 and 105 of respectively the input side 100 and the output side 101.

The sets of planetary gearing 102 and 103 are supported in a rotatable manner either each on their own separated planet carrier 106 and 107 or together on a common planet carrier 108.

Each set of planetary gearing 102 and 103 is furthermore composed of a number of planetary gearing elements 109 and 110 which are disposed circumferentially and preferably, but not necessarily, equally spaced from one another on their supporting planet carrier 106, 107 or 108.

The first set of planetary gearing 102 and the second set of planetary gearing 103 are linked to form a linking mechanism 111 for transmission of torque and/or speed between the input side 100 and the output side 101 of the second stage 3.

Another important characteristic of a second stage 3 of a gearwheel transmission 1 in accordance with the invention is that a first component 118, i.e. a sun wheel, or a ring wheel of the second stage 3 or a separate planet carrier 106 of the gearwheel transmission 1, is forming a torque resisting or torque controlling means 119 in that it is permanently blocked or impeded in a controllable way.

Furthermore, dependent on the type of component the first component 118 is, there is always a kind of complementary second component 120, i.e. respectively a rotatable sun wheel or a rotatable ring wheel of the second stage 3 or a rotatable planet carrier 7 of the gearwheel transmission 1 which is interconnected or interacting with the second stage output shaft 20.

In FIG. 26 this is illustrated by having a dashed line 121 which symbolizes the interaction of the concerned torque resisting means 119 with a housing 17 or ground and a dashed line 122 which symbolizes the interconnection of the corresponding second component 120 with the second stage output shaft 20.

The benefit of such a configuration has been discussed in long in the introduction.

It is clear that according to the invention, apart from the particular mechanical structure of each stage 2 or 3, the stage 2 and 3 also still differ as far as their execution is concerned, the first stage being optimized so to obtain an increased overall efficiency, while the second stage is optimized in order to realize a higher capacity for transmitting torque, which has been explained in detail above.

Different more practically elaborated embodiments of second stages 3 are now described in more detail by means of FIGS. 27 to 29.

In FIG. 27 a second stage 3 is represented which is a second stage 3 as applied in all the examples of the FIGS. 1 to 22, being a second stage 3 which forms a ring differential gearing 117.

In order to demonstrate that this particular example fits perfectly within a broader scope of second stages 3, which have been described with respect to FIG. 26 using some more abstract categories, the more abstract categories will now be linked to the more practical former descriptions.

It is obvious that the elements of a second stage represented in FIG. 27 are completely equivalent with the already described examples of second stages 3 in the FIGS. 1 to 22.

At least the elements displayed in FIG. 27 are comprised in the former examples and it is of course not excluded from the invention to execute the second stare 3 with additional elements, similar to those represented in the earlier examples or with still other additional elements.

In the case of the second stage 3 of a gearwheel transmission 1 in accordance with the invention as represented in FIG. 27 the second stage 3 comprises clearly a planetary gear train system 99 with an input side 100 and an output side 101, which has a quasi duplicated form, which was earlier described as being a second stage compound planetary type gearwheel assembly 23.

The first set of planetary gearing 102 of the input side 100 and the second set of planetary gearing 103 of the output side 101 are quasi identical but slightly different from one another and each comprise a number of planetary gearing elements 109 and 110 which are of a certain set type and which were earlier described as being a first group 29 and a second group 31 of planetary gearwheels.

This set type is such that the concerned set comprises a number of planetary gearwheel components 112 and 113 of a set of compound planetary gearwheels 114, earlier indicated as being second stage compound planetary gearwheels 24, which are formed by fixedly interconnected, stepped second stage planetary gearwheels 26 and 27.

The sets of planetary gearing 102 and 103 are supported in a rotatable on a common planet carrier 108, which was earlier described as being an intermediate planet carrier 21 which is separated from the first stage input shaft 5 as well as from the second stage output shaft 20.

As explained in the introduction, this planet carrier 108 can be considered as being a part of the second stage 3 or the first stage 2 or of neither of them, dependent on which elements are mounted in the planet carrier 108.

A linking mechanism 111 for transmission of torque and/or speed between the input side 100 and the output side 101 of the second stage 3 links the first set of planetary gearing 102 and the second set of planetary gearing 103.

This linking mechanism 111 is in this case realized by a fixed interconnection 115 of corresponding, constitutive components 112 or 113 of the first and second sets of planetary gearing 102 and 103 forming compound planetary linkage gearwheels 114 which are supported on a single common planet carrier 108.

The first set of planetary gearing 102 and the second set of planetary gearing 103 interact respectively with first and second interacting gearing 104 and 105 of respectively the input side 100 and the output side 101 which are of a certain interacting gearing type, which interacting gearing type in the case of FIG. 27 consists each time of a single, separate gearwheel 116, respectively ring wheel 28 and ring wheel 30.

The first and the second interacting gearing 104 and 105 taken together are therefore in this case a pair of ring wheels 28 and 30, which are quasi identical, hut slightly different elements.

The gearwheel transmission 1 represented in FIG. 27 is a ring differential gearing 117 and therefore one of the ring wheels, i.e. ring wheel 28 of the second stage 3 of the gearwheel transmission 1, is forming a first component 118 which serves as a torque resisting or torque controlling means 119 in that it is permanently blocked by being fixedly connected to the housing 17.

The other ring wheel 30 is mounted in a rotatable manner in the housing 17 and is forming a second component 120 of the gearwheel transmission 1 which is interconnected to the second stage output shaft 20.

As already mentioned, the first stage 2 can be executed in all kinds of ways, examples of which have been shown and discussed with respect to FIGS. 1 to 22.

Dependent on the type of first stage 2, elements can be added to the second stage 3 in order to realize the interconnection or interaction with the first stage 2, symbolized by the arrow 93 in FIG. 27.

For example, a single second stage input sun wheel 40 can be added to the second stage 3, which meshes with the first set of planetary gearing 102 so to serve as a second stage input element 39, as represented in FIG. 2.

In general, the interaction 93 between the first stage 2 and the second stage 3 can be realized in 4 different manners, one or more first stage output elements 6 or 37 being fixedly interconnected with one or more second stage input elements 33 or 39, as discussed for example in the introduction.

The second stage 3 illustrated in FIG. 28 has a lot of similarities with the second stage 3 of FIG. 27, but is slightly different in that this time the first and second interacting gearing 104 and 105, are each formed by a single, separated gearwheel 116, which is this time a sun wheel 123 or 124, instead of a ring wheel 28 or 30.

The first and the second interacting gearing 10 and 105 taken together are therefore in this case a pair of sun wheels 123 and 124, which are quasi identical, but slightly different elements.

This second stage 3 therefore constitutes a so-called sun differential gearing 97, since it comprises a pair of separated sun wheels 123 and 124 forming the first and second interacting gearing 104 and 105, while a linking mechanism 111 is realized between the input side 100 and the output side 101 of the second stage in the same manner as in FIG. 27, corresponding components 112 and 113 of the first and second set of planetary gearing 109 and 110 being fixedly interconnected by a fixed interconnection 115 to form a set of compound planetary gearwheels 114 and supported on a single, common planet carrier 108.

Sun wheel 123 plays the role of first component 118 which is fixedly connected to the housing 17 and forms the torque resisting or torque controlling means 119, while the other sun wheel 124 is the second component 120 that is fixedly connected to the second stage output shaft 20.

First stages 2 of types similar to those described with respect to FIGS. 1 to 22 or of still other types can be connected to this second stage 3 in the form of a sun differential gearing 97 in the same manners as described before.

FIG. 29 illustrates still another type of second stage 3, the first set and the second set of planetary gearing 102 and 103 each comprising a number of planetary gearing elements 109 and 110 which are of a certain other set type, than in the preceding cases.

This time the set type is such that a set comprises a number of separate, simple planetary gearwheels 125 and 126.

The separate, simple planetary gearwheels 125 and 126 of each set 102 or 103 are furthermore supported in a rotatable manner on their own separated planet carrier 106 or 107.

Also the first and the second interacting gearing 104 and 105 are of a certain different interacting gearing type, which interacting gearing type is such that each concerned interacting gearing 104 or 105 is composed of a pair of gearwheel components 127 and 128 or 129 and 130 of a pair of compound interacting gearwheels, respectively compound interacting gearwheel 131 and compound interacting gearwheel 132.

In particular, the gearwheel components 127 and 129 are sun wheel components 127 and 129 of a compound interacting sun wheel 131, while the gearwheel components 128 and 130 are ring wheel components 128 and 130 of a compound interacting ring wheel 131.

As a consequence, in this example the first and the second interacting gearing 104 and 105 of the second stage 3 taken together form a pair of compound gearwheels 131 and 132 which is composed by a compound sun wheel 131 and a compound ring wheel 132.

The linking mechanism 111 which links the input side 100 to the output side 101 of the second stage 3 is, in the example of FIG. 29, formed by the pair of compound gearwheels 131 and 132 which is composed by the compound sun wheel 131 and the compound ring wheel 132, so that actually a fixed interconnection 115 is obtained between the first interacting gearing 104 and the second interacting gearing 105 and not between the first set of planetary gearing 102 and the second set of planetary gearing 103, as was the case in the preceding examples.

It is clear that also in the example of FIG. 29 the planetary gear train system 99 has an input side 100 and an output side 101 which are executed in a quasi duplicated form.

In particular, the input side 100 and output side 101 of the second stage 3 of the gearwheel transmission 1 each comprise an element, which is represented in this case by a planet carrier 106 or 107, forming together a pair of separated, quasi identical, but slightly different elements 106 and 107, so to form a second stage 3 which is a so-called carrier differential gearing 98.

In this case the pair of separated elements is a pair of separated planet carriers 106 and 107, each planet carrier 106 or 107 of the pair supporting one of the first and second set of planetary gearing 102 and 103, which are each composed of a number of separate, simple planetary gearwheels 125 and 126, while these first and second set of planetary gearing 102 and 103 are linked by a fixed interconnection 115 of the first and second interacting gearing 104 and 105.

These separate planet carriers 106 and 107 respectively form the first component 118 and the second component 120 of the gearwheel transmission 1, since the planet carrier 106 is fixedly connected to the housing 17 or ground so to function as a torque resisting or torque controlling means 119, while the planet carrier 107 is fixedly connected with the second stage output shaft 20.

FIGS. 30 to 32 illustrate some embodiments of a gearwheel transmission 1 in accordance with the invention wherein a certain technique has been applied.

In particular, FIG. 30 is an embodiment which is completely equivalent with the embodiment illustrated in FIG. 1.

A great difference with the example of FIG. 1 however, is that in the example of FIG. 30 at the output of the first stage 2 there is only one single first stage output planetary gearwheel 133 instead of a number of first stage output planetary gearwheels 9, this number corresponding to the number of planetary gearwheels 26 and 27 in the second stage 3 as was the case in FIG. 1.

This time the second stage 3 has still a first set 102 and a second set 103 of planetary gearing consisting of multiple planetary gearing elements 109 and 110 which form compound planetary gearwheels 114, but only one compound planetary gearwheel 134 of these compound planetary gearwheels 114 is fixedly connected to the single first stage output planetary gearwheel 133 and this one compound planetary gearwheel 114 or 24 therefore forms a single second stage input element 39.

The other compound planetary gearwheels 135 which are not directly connected to the first stage 2 still help to share the torque between the two ring wheels 28 and 30 of the ring differential gearing 117 of which the second stage 3 is composed.

This example is the most extreme example, wherein there is only one single first stage output planetary gearwheel 133 instead of a number of first stage output planetary gearwheels 9, but it is of course not excluded from the invention to compose a gearwheel transmission 1 wherein the first stage 2 has a certain number N1 of first stage output planetary gearwheels 9 and wherein this number N1 does not correspond to the number N2 of planetary gearwheels 26 and 27 in the second stage 3, N1 being smaller than N2.

Such an embodiment can be considered as an embodiment wherein the first stage 2 is realized in a somewhat less heavy execution compared to the case wherein all the planetary gearwheels 26 and 27 in the second stage 3 have their complement in the first stage 2, but on the other hand in such an embodiment the first stage 2 comprises still more first stage output planetary gearwheels 9 than in the extremely light execution with only one single first stage output planetary gearwheel 133.

The embodiment illustrated in FIG. 31 is a somewhat simplified version of the former embodiment of FIG. 30.

Indeed, the first stage 2 is reduced to a gearwheel transmission composed of a first stage entry gearwheel 114 which meshes with the single first stage output planetary gearwheel 133, while the interconnection mechanism 7 of the former example has been taken away.

FIG. 32 illustrates still another embodiment of a gearwheel transmission 1 in accordance with the invention, which is executed more or less in the same way as the embodiment of FIG. 31, but this time a first stage hypoid gearing 58 is added at the entry of the first stage 2, completely similar to what was the case in FIG. 11.

Hereby, an intermediate gearwheel 136 has been used to connect this first stage hypoid gearing 58 to the single first stage output planetary gearwheel 133.

It is clear that also the examples represented in FIGS. 31 and 32 can be executed with a first stage 2 which has a certain number N1 of first stage output planetary gearwheels 9 and wherein this number N1 does not correspond to the number N2 of planetary gearwheels 26 and 27 in the second stage 3, N1 being smaller than N2.

It is clear that many other possible embodiments are not excluded from the invention.

The present invention is in no way limited to the embodiments of a gearwheel transmission an infinitely variable transmission IVT, a prosthesis or orthosis or a robotic machine described above and represented in the drawings, but such a gearwheel transmission 1, infinitely variable transmission IVT, prosthesis or orthosis or robotic machine may be realised in different shapes and dimensions, without departure from the scope of the invention.

The invention claimed is:

1. A gearwheel transmission with high transmission ratio and improved efficiency and/or increased capacity for transmitting torque, comprising a first stage and a second stage, which are interconnected and/or are interacting with one another for transmission of torque and rotational speed from a first stage input shaft to a second stage output shaft and/or vice versa, the gearwheel transmission provided in a housing, wherein the first stage comprises at least a first stage entry gearwheel which is mounted fixedly on the first stage input shaft and which is interacting for the transmission of rotational speed and torque with one or more first stage output elements, in a direct manner, or indirectly through an interconnection mechanism comprising one or more interconnection gearwheels; and wherein the second stage comprises a second stage planetary type gearwheel assembly, wherein the second stage is a differential gearing comprising a planetary gear train system which is executed in a quasi duplicated form composed of an input side and an output side, comprising respectively a first set and a second set of planetary gearing, which are mutually quasi identical but slightly different from one another, which interact respectively with first and second interacting gearing of respectively the input side and the output side and which sets are supported in a rotatable manner either each on their own separated planet carrier or together on a common planet carrier, each set of planetary gearing being composed of a number of planetary gearing elements which are disposed circumferentially on their supporting planet carrier, the first set and the second set of planetary gearing being linked to form a linking mechanism for transmission of torque and/or speed between the input side and the output side;

wherein at least the gearwheels of the first stage and the second stage are executed according to a set of execution parameters which influence transmission efficiency and/or capacity for transmitting torque and wherein certain gearwheels of the gearwheel transmission are executed with at least some of their execution parameters set to different parameter values (PV), in such a way that the overall transmission efficiency considered in the first stage as a whole is higher than the overall transmission efficiency considered in the second stage as a whole and/or the overall capacity for transmitting torque considered in the second stage as a whole is higher than the overall capacity for transmitting torque considered in the first stage as a whole; and, wherein a first component, i.e. a sun wheel or a ring wheel of the second stage or a planet carrier of the gearwheel transmission, is forming a torque resisting or torque controlling means in that it is permanently blocked or impeded in a controllable way; and wherein a second component, i.e. respectively a rotatable sun wheel or a rotatable ring wheel of the second stage or a rotatable planet carrier of the gearwheel transmission is interconnected or interacting with the output shaft.

2. The gearwheel transmission according to claim 1, wherein the first and the second interacting gearing of the second stage taken together are one of the following:
  a) a pair of separate ring wheels,
  b) a pair of separate sun wheels, or
  c) a pair of compound gearwheels which is composed by a compound sun wheel and a compound ring wheel,
and/or in that the linking mechanism is realized in one of the following ways:
  a) the linking mechanism is formed by a fixed interconnection of corresponding, constitutive components of the first and second sets of planetary gearing forming compound planetary linkage gearwheels which are supported on a single common planet carrier, or
  b) the linking mechanism is formed by the pair of compound gearwheels which is composed by the compound sun wheel and the compound ring wheel, while the first and second set of planetary gearing are separate from one another and each respectively supported on their own, separated planet carriers,
and/or in that the second stage is one of the following:
  a) a so-called ring differential gearing in the case the ring wheels form the first component and second component of the second stage;
  b) a so-called sun differential gearing in the case the sun wheels form the first component and second component of the second stage; or,
  c) a so-called carrier differential gearing in the case the separate planet carriers form the first component and second component of the second stage.

3. The gearwheel transmission according to claim 1, further comprising an intermediate planet carrier, which is mounted in a rotatable manner in the housing and which is separated from the first stage input shaft as well as from the second stage output shaft and wherein intermediate carrier planetary gearwheel shafts are provided on said intermediate planet carrier, wherein the second stage comprises a second stage compound planetary type gearwheel assembly, comprising a second stage fixed ring wheel which is fixedly connected to the housing, a second stage rotatable ring wheel which is rotating simultaneously with the second stage output shaft, as well as second stage compound planetary gearwheels which each are supported on a corresponding primary, intermediate carrier planetary gearwheel shaft, each first planetary gearwheel of such a second stage compound planetary gearwheel meshing with the second stage fixed ring wheel and each second planetary gearwheel of such a second stage compound planetary gearwheel meshing with the second stage rotatable ring wheel, wherein the first planetary gearwheels of the second stage compound planetary gearwheel form the planetary gearing elements of a first set of planetary gearing of the second stage and wherein the second planetary gearwheels of the second stage compound planetary gearwheels form the planetary gearing elements of a second set of planetary gearing of the second stage.

4. The gearwheel transmission according to claim 1, wherein certain gearwheels of the gearwheel transmission are executed with at least some of their execution parameters set to different parameter values (PV), in such a way that following a torque transmission path (TTP1) through the gearwheel transmission from the first stage input shaft towards the second stage output shaft the difference in execution is such that the capacity for transmitting torque of consecutive gearwheels along the path (TTP1) is the same or increasing, and when following a torque transmission path (TTP2) through the gearwheel transmission from the second stage output shaft towards the first stage input shaft the difference in execution is such that the efficiency of transmission realized by consecutive gearwheels along the path (TTP2) is the same or increasing, wherein the first stage is a high speed-low torque stage and the second stage is a low speed-high torque stage, compared relatively to one another, the first stage comprising first stage gearwheels interacting with one another for transmitting rotational speed of and torque delivered at the first stage input shaft into a decreased rotational speed of and an increased torque at one or more first stage output elements, the second stage comprising second stage gearwheels interacting with one another for transmitting rotational speed of and torque at one or more second stage input elements into rotational speed of and torque at a second stage output shaft, wherein first stage gearwheels or other elements of the first stage and second stage gearwheels or other elements of the second stage are each executed in accordance with the set of execution parameters, wherein one or more of these first stage gearwheels or other elements of the first stage and one or more second stage gearwheels or other elements of the second stage are executed in such a way that one or more of their execution parameters have parameter values (PV) which are different in the first stage compared to the corresponding parameter values (PV) in the second stage, wherein in particular first parameter values (PV1) of certain mechanical design parameters of this set for the concerned gearwheels or elements of the first stage and second parameter values (PV2) of the corresponding mechanical design parameters of this set for the concerned gearwheels or elements of the second stage differ from one another in such a way that the first parameter values (PV1) increase efficiency in a high speed-low torque mechanical gearing, while the second parameter values (PV2) increase robustness, strength and/or capacity to transmit torque in a low speed-high torque mechanical gearing, compared relatively to one another.

5. The gearwheel transmission according to claim 1, wherein the gearwheels or other elements of the gearwheel transmission are each executed in accordance with the set of execution parameters which comprises one or more of the following execution parameters which influence the efficiency or the capacity for transmitting torque of the concerned components:
  a module (MOD);
  a quality level (QL);
  an accuracy (ACC);
  a profile-shift (PS);
  a contact ratio (CR);
  a tooth geometry (TG);
  a filet profile (FP);
  a roughness (RG);
  a material (MA); and, a surface hardness (SH)
wherein a first pair of gearwheels of the gearwheel transmission is executed with:
a first module (MOD_PV1);
a first quality level (QL_PV1);
a first accuracy (ACC_PV1);
a first profile-shift (PS_PV1);
a first contact ratio (CR_PV1);
a first tooth geometry (TG_PV1);
a first roughness (RG_PV1);
a first material (MA_PV1); and,
a first surface hardness (SH_PV1);
wherein a second pair of gearwheels of the gearwheel transmission, which on a torque transmission path (TTP1) through the gearwheel transmission from the first stage input shaft towards the second stage output shaft is positioned closer to the second stage output shaft than the first pair of gearwheels, is executed with:
a second module (MOD_PV2);
a second quality level (QL_PV2);
a second accuracy (ACC_PV2);
a second profile-shift (PS_PV2);
a second contact ratio (CR_PV2);
a second tooth geometry (TG_PV2);
a second roughness (RG_PV2);
a second material (MA_PV2); and,
a second surface hardness (SH_PV2); and
wherein one or more of the following conditions is or are fulfilled:
the first module (MOD_PV1) is smaller than the second module (MOD_PV2);
the first quality level (QL_PV1) is higher than the second quality level (QL_PV2);
the first accuracy (ACC_PV1) is higher than the second accuracy (ACC_PV2);
the level and distribution of the first profile shift (PS_PV1) are optimized for efficiency and the level and distribution of the second profile shift (PS_PV2) are optimized for robustness;
the first contact ratio (CR_PV1) is smaller than the second contact ratio (CR_PV2);
the first tooth geometry (TG_PV1) is optimized for efficiency and the second tooth geometry (TG_PV2) is optimized for increasing capacity for transmitting torque;
the roughness (CR_PV1) in the first stage is smaller than the roughness (CR_PV2) in the second stage;
the first material (MA_PV1) is lighter and/or has a lower strength than the second material (MA_PV2); and/or,
the first surface hardness (SH_PV1) is smaller than the second surface hardness (SH_PV2).

6. The gearwheel transmission according to claim 1, wherein the first stage output elements are formed by a group of circumferentially spaced apart first stage output planetary gearwheels which are each interconnected with or form a monolithic part with a corresponding planetary gearwheel of a group of circumferentially spaced apart second stage planetary gearwheels, which represent second stage input elements, so to form hybrid compound planetary gearwheels comprising a series of three planetary gearwheels, composed of a pair of second stage planetary gearwheels and a first stage planetary gearwheel.

7. The gearwheel transmission according to claim 6, wherein the first stage outlet sun wheel is meshing with every one of the first stage output elements.

8. The gearwheel transmission according to claim 6, wherein the first stage planetary gearwheels are each first stage compound planetary gearwheels forming a pair of fixedly interconnected, stepped first stage planetary gearwheels, these first stage compound planetary gearwheels forming:
a first group of circumferentially spaced apart first stage planetary gearwheels composed by the first planetary gearwheel of each afore-mentioned pair of first stage planetary gearwheels; as well as,
a second group of circumferentially spaced apart first stage planetary gearwheels composed by the second planetary gearwheel of each afore-mentioned pair of first stage planetary gearwheels; and
wherein the first planetary gearwheels are provided concentrically around the first stage input shaft.

9. The gearwheel transmission according to claim 8, wherein the gearwheel transmission comprises an actuator which is mounted at the first stage input shaft for driving the first stage input shaft in a rotatable manner and in that the input shaft is extending inwardly into a free space in the second stage at the center of the intermediate planet carrier and that the actuator is integrated in the same free space.

10. The gearwheel transmission according to claim 6, wherein the gearwheel transmission comprises an actuator which is mounted at the first stage input shaft for driving the first stage input shaft in a rotatable manner and in that the input shaft is extending inwardly into a free space in the second stage at the center of the intermediate planet carrier and that the actuator is integrated in the same free space.

11. The gearwheel transmission according to claim 1, wherein the first stage output element is a single first stage output element which is formed by a first stage output planet carrier and which is interconnected with a second stage input element, which is a single second stage input element.

12. The gearwheel transmission according to claim 11, wherein the single second stage input element is a second stage input sun wheel of the second stage compound planetary type gearwheel assembly, wherein this second stage input sun wheel is meshing with each planetary gearwheel of a group of circumferentially spaced apart second stage planetary gearwheels composed by a planetary gearwheel of each second stage compound planetary gearwheel.

13. The gearwheel transmission according to claim 1, wherein the first stage comprises a first stage planetary type gearwheel assembly, wherein the first stage entry gearwheel is a first stage entry sun wheel of the first stage planetary type gearwheel assembly, and wherein the first stage planetary type gearwheel assembly furthermore comprises a group of circumferentially spaced apart first stage planetary gearwheels provided concentrically around the first stage input shaft and each interacting with the first stage entry sun wheel,
wherein the first stage planetary gearwheels are each supported by a first stage planetary gear shaft in a rotatable manner and each first stage planetary gear shaft is mounted fixedly on a first stage planet carrier circumferentially spaced apart and concentrically with the first stage input shaft or the first stage planetary gearwheels are each supported by the first stage planetary gear shaft by being fixedly connected to the concerned first stage planetary gear shaft and each first stage planetary gear shaft is mounted in a rotatable manner on the first stage planet carrier circumferentially spaced apart and concentrically with the first stage input shaft, wherein the first stage planetary gearwheels are each meshing with a first stage fixed ring wheel which is concentric with the first stage input shaft and which is fixedly connected to the housing of the gearwheel transmission, wherein optionally the afore-mentioned first stage planet carrier is fixedly interconnected with an additional first stage outlet sun wheel, which is axially aligned with the first stage input shaft.

14. The gearwheel transmission according to claim 13, wherein the first stage outlet sun wheel is meshing with every one of the first stage output elements.

15. The gearwheel transmission according to claim 1, wherein the gearwheel transmission comprises one or more clutches which is or are mounted between a pair of elements of the gearwheel transmission, such as between the first stage input shaft and a first stage entry gearwheel or first stage entry sun wheel or between any of the planetary gearwheel shafts and a planetary gear wheel which is mounted on that planetary gearwheel shaft, allowing transmission of torque between the concerned elements in one sense and preventing transmission of torque between the concerned elements in the opposite sense and/or in that the gearwheel transmission comprises one or more brakes, which is or are provided between an element or elements of the gearwheel transmission and the housing for controlling the rotational speed of parts of the gearwheel transmission, such as the rotational speed of the first stage input shaft, the second stage output shaft, planetary gearwheels, gearwheels in general, planet carriers or rotatable ring wheels.

16. An infinitely variable transmission, comprising at least one gearwheel transmission in accordance with claim 1.

17. A prosthesis or orthosis or robotic machine, comprising at least one infinitely variable transmission according to claim 16.

18. A prosthesis or orthosis or robotic machine, comprising at least one gearwheel transmission in accordance with claim 1.

* * * * *